United States Patent
Fader et al.

(10) Patent No.: US 9,249,158 B2
(45) Date of Patent: Feb. 2, 2016

(54) CYTOMEGALOVIRUS INHIBITOR COMPOUNDS

(71) Applicants: Lee Fader, New Milford, CT (US); Pierre Louis Beaulieu, Rosemere (CA); Murray Bailey, Pierrefonds (CA); Francois Bilodeau, Laval (CA); Rebekah J. Carson, Mascouche (CA); André Giroux, Ste-Anne-de-Bellevue (CA); Cédrickx Godbout, Attenweiler (DE); Oliver Hucke, Montreal (CA); Marc-André Joly, Terrebonne (CA); Mélissa Leblanc, Laval (CA); Olivier Lepage, Laval (CA); Benoit Moreau, Newton, MA (US); Julie Naud, Blanville (CA); Martin Poirier, Blanville (CA); Elisia Villemure, San Francisco, CA (US)

(72) Inventors: Lee Fader, New Milford, CT (US); Pierre Louis Beaulieu, Rosemere (CA); Murray Bailey, Pierrefonds (CA); Francois Bilodeau, Laval (CA); Rebekah J. Carson, Mascouche (CA); André Giroux, Ste-Anne-de-Bellevue (CA); Cédrickx Godbout, Attenweiler (DE); Oliver Hucke, Montreal (CA); Marc-André Joly, Terrebonne (CA); Mélissa Leblanc, Laval (CA); Olivier Lepage, Laval (CA); Benoit Moreau, Newton, MA (US); Julie Naud, Blanville (CA); Martin Poirier, Blanville (CA); Elisia Villemure, San Francisco, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/390,246

(22) PCT Filed: Apr. 3, 2013

(86) PCT No.: PCT/US2013/035059
§ 371 (c)(1),
(2) Date: Oct. 2, 2014

(87) PCT Pub. No.: WO2013/152065
PCT Pub. Date: Oct. 10, 2013

(65) Prior Publication Data
US 2015/0080366 A1  Mar. 19, 2015

Related U.S. Application Data

(60) Provisional application No. 61/620,737, filed on Apr. 5, 2012.

(51) Int. Cl.
| | | |
|---|---|---|
| C07D 498/22 | (2006.01) | |
| C07D 471/14 | (2006.01) | |
| A61K 31/4375 | (2006.01) | |
| C07D 471/22 | (2006.01) | |
| C07D 491/147 | (2006.01) | |
| C07D 498/14 | (2006.01) | |
| C07D 519/00 | (2006.01) | |
| A61K 31/496 | (2006.01) | |
| A61K 31/506 | (2006.01) | |
| A61K 31/5377 | (2006.01) | |
| A61K 31/5383 | (2006.01) | |
| A61K 45/06 | (2006.01) | |
| C07D 491/107 | (2006.01) | |

(52) U.S. Cl.
CPC .......... *C07D 498/22* (2013.01); *A61K 31/4375* (2013.01); *A61K 31/496* (2013.01); *A61K 31/506* (2013.01); *A61K 31/5377* (2013.01); *A61K 31/5383* (2013.01); *A61K 45/06* (2013.01); *C07D 471/14* (2013.01); *C07D 471/22* (2013.01); *C07D 491/107* (2013.01); *C07D 491/147* (2013.01); *C07D 498/14* (2013.01); *C07D 519/00* (2013.01)

(58) Field of Classification Search
CPC ............. C07D 498/22; C07D 491/107; C07D 471/22; C07D 471/14; A61K 31/506
USPC .................. 546/15, 64, 82; 544/99
See application file for complete search history.

(56) References Cited

FOREIGN PATENT DOCUMENTS

| EP | 0452873 A1 | 10/1991 |
| WO | 0170742 A1 | 9/2001 |
| WO | 0174816 A1 | 10/2001 |

OTHER PUBLICATIONS

Prevention of Maternal and Congenital Cytomegalovirus Infection, Julie Johnson et al, 2013.*
International Search Report for PCT/US2013/035059 mailed Oct. 4, 2013.

\* cited by examiner

*Primary Examiner* — Rita Desai
(74) *Attorney, Agent, or Firm* — Michael P. Morris; Usha R. Patel

(57) ABSTRACT

Compounds of Formula (I) wherein n, A, $R^1$, $R^2$, $R^3$ and $R^5$ are defined herein, are useful for the treatment of cytomegalovirus disease and/or infection.

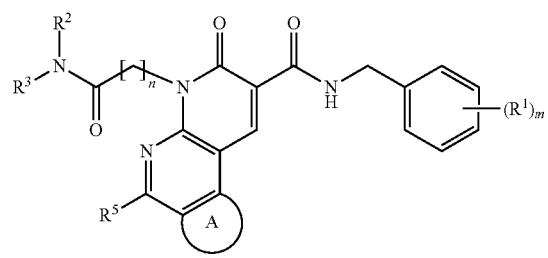

23 Claims, No Drawings

SEQUENCE LISTING

```
<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
agctcgttta gtgaacc                                                 17

<210> SEQ ID NO 2
<211> LENGTH: 58
<212> TYPE: DNA
<213> ORGANISM: Artificial Sequence
<220> FEATURE:
<221> NAME/KEY: source
```

<223> OTHER INFORMATION: /note="Description of Artificial Sequence: Synthetic oligonucleotide"

<400> SEQUENCE: 2
gaggtcaaaa cagcgtggat ggcgtctcca ggcgatctga cggttcacta aacgagct    58

CYTOMEGALOVIRUS INHIBITOR COMPOUNDS

RELATED APPLICATIONS

This application is the national phase entry under 35 U.S.C. §371 of International Application No. PCT/US2013/035059, filed Apr. 3, 2013, which claims priority to U.S. Provisional Application Ser. No. 61/620,737, filed Apr. 5, 2012, which are hereby incorporated by reference in their entireties.

SEQUENCE LISTING

The instant application contains a Sequence Listing which has been submitted in ASCII format via electronic filing and is hereby incorporated by reference in its entirety. Said ASCII copy, created on Aug. 7, 2013, is named 13-0176-PCT_SL.txt and is 797 bytes in size.

FIELD OF THE INVENTION

The present invention relates to 1,8-naphthyridin-2(1H)-one analogs and their use as inhibitors of human cytomegalovirus (CMV) DNA polymerase, pharmaceutical compositions containing such analogs, and methods of using these analogs in the treatment and prevention of CMV disease and/or infection.

BACKGROUND OF THE INVENTION

CMV, a β-herpes virus, is a frequent and ubiquitous virus that affects all populations, worldwide, including adults and children with normal or compromised immune systems. The current therapies approved for the treatment of CMV include Valganciclovir, Ganciclovir, Cidofovir and Foscarnet. Each of these therapies inhibit CMV DNA polymerase, a protein encoded by the UL54 gene, which is an enzyme essential for viral replication (*PNAS* 2003, 100(24), 14223-14228 and WO 2005012545).

SUMMARY OF THE INVENTION

The present invention provides a novel series of compounds having inhibitory activity against CMV DNA polymerase.

Further objects of this invention arise for the one skilled in the art from the following description and the examples.

Representative embodiments of the compound aspect of the invention are described below and throughout the specification.

In one embodiment the invention provides a compound of Formula (I):

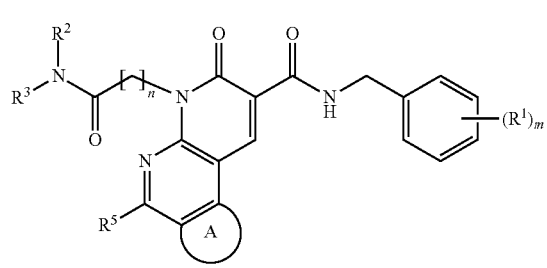

(I)

wherein
n is 1, 2 or 3;
m is 1, 2 or 3;
$R^1$ is halo, —CN, $(C_{1-6})$alkyl, OH, —O—$(C_{1-6})$alkyl, $(C_{1-6})$haloalkyl or nitro;
$R^2$ is H or $(C_{1-6})$alkyl optionally substituted with halo, —CN, —$(C_{3-7})$cycloalkyl, —O—$(C_{1-6})$alkyl, OH, —$NH_2$, —NH$(C_{1-6})$alkyl or —N($(C_{1-6})$alkyl)$_2$;
$R^3$ is H, $(C_{1-6})$alkyl, $(C_{3-7})$cycloalkyl, aryl, heterocyclyl, heteroaryl, —$(C_{1-6})$alkyl-$(C_{3-7})$cycloalkyl, —$(C_{1-6})$alkyl-aryl, —$(C_{1-6})$alkyl-heterocyclyl or —$(C_{1-6})$alkyl-heteroaryl, wherein each said alkyl, cycloalkyl, aryl, heterocyclyl and heteroaryl, either alone or in combination with another radical, is optionally mono-, di-, or tri-substituted with $R^{32}$;
or $R^2$ and $R^3$, together with the N to which they are attached, are linked to form a heterocyclyl or heteroaryl; wherein each said heterocyclyl and heteroaryl are optionally mono-, di-, or tri-substituted with $R^{32}$;
$R^{32}$ is each independently selected from the group consisting of $R^{33}$, halo, oxo, —CN, OH, SH, —COOH, —$(C_{1-6})$alkyl, —O—$(C_{1-6})$alkyl, —S—$(C_{1-6})$alkyl, $(C_{3-7})$cycloalkyl, $(C_{1-6})$haloalkyl, —C(=O)—O—$(C_{1-6})$alkyl, —$SO_2NH_2$, —$SO_2$—NH$(C_{1-6})$alkyl, —$SO_2$—N($(C_{1-6})$alkyl)$_2$, —SO$(C_{1-6})$alkyl, —$SO_2(C_{1-6})$alkyl, —C(=O)—$NH_2$, —C(=O)—NH$(C_{1-6})$alkyl, —C(=O)—N($(C_{1-6})$alkyl)$_2$, —C(=O)—NH—$SO_2(C_{1-6})$alkyl, —$SO_2$—NH—C(=O)—$(C_{1-6})$alkyl, —$NH_2$, —NH$(C_{1-6})$alkyl, —N($(C_{1-6})$alkyl)$_2$, —NH$(C_{3-7})$cycloalkyl, —N($(C_{1-6})$alkyl)$(C_{3-7})$cycloalkyl, —NH—C(=O)$(C_{1-6})$alkyl, —NH—C(=O)O$(C_{1-6})$alkyl, heterocyclyl (optionally substituted with $(C_{1-6})$alkyl) and heteroaryl (optionally substituted with $(C_{1-6})$alkyl);
$R^{33}$ is $(C_{1-6})$alkyl optionally mono- or di-substituted with OH, —O—$(C_{1-6})$alkyl, —$NH_2$, —NH$(C_{1-6})$alkyl or —N($(C_{1-6})$alkyl)$_2$;
Ring A is heterocyclyl or heteroaryl, wherein Ring A is optionally mono-, di-, or tri-substituted with $R^4$;
$R^4$ is each independently selected from the group consisting of halo, oxo, cyano, nitro, $(C_{1-6})$alkylidene, $R^{42}$, —C(=O)—$R^{42}$, —C(=O)O$R^{42}$, —O$R^{42}$, —S$R^{42}$, —SO$R^{42}$, —$SO_2R^{42}$, —N($R^{43}$)$R^{42}$, —$(C_{1-6})$alkyl-N($R^{43}$)$R^{42}$, —C(=O)—N($R^{43}$)$R^{42}$, —N($R^{43}$)—C(=O)$R^{42}$, —N($R^{43}$)—C(=O)O—$R^{42}$, —C(=O)—N(H)—$SO_2R^{42}$, —$SO_2$—N(H)—C(=O)$R^{42}$, —O—C(=O)—N($R^{43}$)$R^{42}$ and —$SO_2$—N($R^{43}$)$R^{42}$;
$R^{42}$ is each independently selected from the group consisting of H, $(C_{1-6})$alkyl, $(C_{2-6})$alkenyl, $(C_{2-6})$alkynyl, —$(C_{1-6})$alkyl-$(C_{3-7})$cycloalkyl, —$(C_{1-6})$alkyl-aryl, —$(C_{1-6})$alkyl-heterocyclyl, —$(C_{1-6})$alkyl-heteroaryl, $(C_{3-7})$cycloalkyl, aryl, heterocyclyl and heteroaryl, wherein each said alkyl, alkenyl, alkynyl, cycloalkyl, aryl, heterocyclyl and heteroaryl, either alone or in combination with another radical, is optionally substituted with 1 to 3 substituents each independently selected from the group consisting of: halo, cyano, OH, —COOH, —O—$(C_{1-6})$alkyl, —S—$(C_{1-6})$alkyl, $(C_{3-7})$cycloalkyl, —O—$(C_{3-7})$cycloalkyl, $(C_{1-6})$haloalkyl, —C(=O)—$(C_{1-6})$alkyl, —C(=O)—O—$(C_{1-6})$alkyl, —$SO_2NH_2$, —$SO_2$—NH$(C_{1-6})$alkyl, —$SO_2$—N($(C_{1-6})$alkyl)$_2$, —SO$(C_{1-6})$alkyl, —$SO_2(C_{1-6})$alkyl, —C(=O)—$NH_2$, —C(=O)—NH$(C_{1-6})$alkyl, —C(=O)—N($(C_{1-6})$alkyl)$_2$, —C(=O)—N(H)—$SO_2(C_{1-6})$alkyl, —$SO_2$—N(H)—C(=O)$(C_{1-6})$alkyl, —$NH_2$, —NH$(C_{1-6})$alkyl, —N($(C_{1-6})$alkyl)$_2$, —NH—C(=O)$(C_{1-6})$alkyl, —NH—C(=O)—O$(C_{1-6})$alkyl and $(C_{1-6})$alkyl optionally mono- or di-substituted with OH, —O—$(C_{1-6})$alkyl, —S—$(C_{1-6})$alkyl, —SO$(C_{1-6})$alkyl, —$SO_2(C_{1-6})$alkyl, heterocyclyl or heteroaryl;
$R^{43}$ is H, $(C_{1-6})$haloalkyl or $(C_{1-6})$alkyl optionally mono- or di-substituted with OH, —O—$(C_{1-6})$alkyl or —O—$(C_{3-7})$cycloalkyl;

$R^5$ is H, halo, —CN, $(C_{1-6})$alkyl, $(C_{1-6})$haloalkyl, —O—$(C_{1-6})$alkyl, $(C_{3-7})$cycloalkyl, —NH$_2$, —NH$(C_{1-6})$alkyl or —N$((C_{1-6})$alkyl$)_2$;
or a salt thereof.

In a further embodiment, the invention provides a compound of Formula (I) as defined above, or a pharmaceutically acceptable salt thereof, wherein n is 1 or 2.

In a further embodiment, the invention provides a compound of Formula (I) as defined above, or a pharmaceutically acceptable salt thereof, wherein n is 1.

In a further embodiment, the invention provides a compound of Formula (I) as defined above, or a pharmaceutically acceptable salt thereof, wherein m is 1 or 2.

In a further embodiment, the invention provides a compound of Formula (I) as defined above, or a pharmaceutically acceptable salt thereof, wherein m is 1.

In a further embodiment, the invention provides a compound of Formula (I) as defined above, or a pharmaceutically acceptable salt thereof, wherein $R^1$ is F, Cl, Br, —CN, OH, O—$(C_{1-3})$alkyl, $(C_{1-3})$alkyl, $(C_{1-3})$haloalkyl or nitro.

In a further embodiment, the invention provides a compound of Formula (I) as defined above, or a pharmaceutically acceptable salt thereof, wherein $R^1$ is F, Cl, Br, —CN, OH or O—$(C_{1-3})$alkyl.

In a further embodiment, the invention provides a compound of Formula (I) as defined above, or a pharmaceutically acceptable salt thereof, wherein $R^2$ is H or $(C_{1-6})$alkyl;
$R^3$ is $(C_{1-6})$alkyl, —$(C_{1-6})$alkyl-$(C_{3-7})$cycloalkyl, —$(C_{1-6})$alkyl-aryl, —$(C_{1-6})$alkyl-heterocyclyl or —$(C_{1-6})$alkyl-heteroaryl, wherein each said alkyl, cycloalkyl, aryl, heterocyclyl and heteroaryl, either alone or in combination with another radical, is optionally mono-, di-, or tri-substituted with $R^{32}$; or
$R^2$ and $R^3$, together with the N to which they are attached, are linked to form a heterocyclyl; wherein said heterocyclyl is optionally mono-, di-, or tri-substituted with $R^{32}$; and
$R^{32}$ is each independently selected from the group consisting of $R^{33}$, halo, oxo, —CN, OH, —COOH, —$(C_{1-6})$alkyl, —O—$(C_{1-6})$alkyl, $(C_{3-7})$cycloalkyl, $(C_{1-6})$haloalkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl$)_2$, —C(=O)—NH—SO$_2(C_{1-6})$alkyl, —SO$_2$—NH—C(=O)—$(C_{1-6})$alkyl, heterocyclyl (optionally substituted with $(C_{1-6})$alkyl) and heteroaryl (optionally substituted with $(C_{1-6})$alkyl);
$R^{33}$ is $(C_{1-6})$alkyl optionally mono- or di-substituted with OH, —O—$(C_{1-6})$alkyl, —NH$_2$, —NH$(C_{1-6})$alkyl or —N$((C_{1-6})$alkyl$)_2$.

In a further embodiment, the invention provides a compound of Formula (I) as defined above, or a pharmaceutically acceptable salt thereof, wherein $R^2$ and $R^3$, together with the N to which they are attached, are linked to form a heterocyclyl; wherein each said heterocyclyl is optionally mono- or di-substituted with $R^{32}$;
$R^{32}$ is each independently selected from the group consisting of $R^{33}$, halo, oxo, —CN, OH, —COOH, —$(C_{1-6})$alkyl, —O—$(C_{1-6})$alkyl, $(C_{3-7})$cycloalkyl, $(C_{1-6})$haloalkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl$)_2$, —C(=O)—NH—SO$_2(C_{1-6})$alkyl, —SO$_2$—NH—C(=O)—$(C_{1-6})$alkyl, heterocyclyl (optionally substituted with $(C_{1-6})$alkyl) and heteroaryl (optionally substituted with $(C_{1-6})$alkyl);
$R^{33}$ is —$(C_{1-6})$alkyl optionally mono- or di-substituted with OH, —O—$(C_{1-6})$alkyl, —NH$_2$, —NH$(C_{1-6})$alkyl or —N$((C_{1-6})$alkyl$)_2$.

In a further embodiment, the invention provides a compound of Formula (I) as defined above, or a pharmaceutically acceptable salt thereof, wherein $R^2$ and $R^3$, together with the N to which they are attached, are linked to form a heterocyclyl, wherein said heterocyclyl is optionally mono- or di-substituted with $R^{32}$;
$R^{32}$ is each independently selected from the group consisting of $R^{33}$, —CN, $(C_{1-6})$haloalkyl, halo and —O$(C_{1-6})$alkyl;
$R^{33}$ is $(C_{1-6})$alkyl optionally mono- or di-substituted with OH.

In a further embodiment, the invention provides a compound of Formula (I) as defined above, or a pharmaceutically acceptable salt thereof, wherein Ring A is a nitrogen containing heterocyclyl or heteroaryl, wherein Ring A is optionally mono-, di-, or tri-substituted with $R^4$;
$R^4$ is each independently selected from the group consisting of halo, oxo, cyano, $R^{42}$, —C(=O)O$R^{42}$, —O$R^{42}$, —N$(R^{43})R^{42}$ and —$(C_{1-6})$alkyl-N$(R^{43})R^{42}$;
$R^{42}$ is each independently selected from the group consisting of H, $C_{1-6}$alkyl, —$(C_{1-6})$alkyl-$(C_{3-7})$cycloalkyl, —$(C_{1-6})$alkyl-aryl, —$(C_{1-6})$alkyl-heterocyclyl, —$(C_{1-6})$alkyl-heteroaryl, $(C_{3-7})$cycloalkyl, aryl, heterocyclyl and heteroaryl, wherein each said alkyl, cycloalkyl, aryl, heterocyclyl and heteroaryl, either alone or in combination with another radical, is optionally substituted with 1 to 2 substituents each independently selected from the group consisting of: halo, oxo, cyano, OH, —COOH, —O—$(C_{1-6})$alkyl, —S—$(C_{1-6})$alkyl, $(C_{3-7})$cycloalkyl, $(C_{1-6})$haloalkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl$)_2$, —NH$_2$, —NH$(C_{1-6})$alkyl, —N$((C_{1-6})$alkyl$)_2$, —NH—C(=O)$(C_{1-6})$alkyl and $(C_{1-6})$alkyl optionally mono- or di-substituted with OH or —O—$(C_{1-6})$alkyl;
$R^{43}$ is H, $(C_{1-3})$haloalkyl or $(C_{1-3})$alkyl optionally mono- or di-substituted with OH, —O—$(C_{1-3})$alkyl or —O—$(C_{3-5})$cycloalkyl.

In a further embodiment, the invention provides a compound of Formula (I) as defined above, or a pharmaceutically acceptable salt thereof, wherein Ring A is a nitrogen containing heterocyclyl or heteroaryl, wherein Ring A is optionally mono- or di-substituted with $R^4$;
$R^4$ is each independently selected from the group consisting of $R^{42}$, O$R^{42}$ and N$(R^{43})R^{42}$;
$R^{42}$ is each independently selected from the group consisting of $(C_{1-6})$alkyl, —$(C_{1-6})$alkyl-$(C_{3-7})$cycloalkyl, $(C_{3-7})$cycloalkyl, heterocyclyl and heteroaryl, wherein each said alkyl, cycloalkyl, heterocyclyl and heteroaryl, either alone or in combination with another radical, is optionally substituted with 1 to 2 substituents each independently selected from the group consisting of: halo, oxo, cyano, OH, —COOH, —O—$(C_{1-4})$alkyl, $(C_{3-7})$cycloalkyl, $(C_{1-4})$haloalkyl, —SO$_2$NH$_2$, —SO$_2$—NH$(C_{1-4})$alkyl, —SO$_2$—N$((C_{1-4})$alkyl$)_2$, —SO$(C_{1-4})$alkyl, —SO$_2(C_{1-4})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$, —NH—C(=O)$(C_{1-4})$alkyl and $(C_{1-4})$alkyl optionally mono- or di-substituted with OH or —O—$(C_{1-4})$alkyl;
$R^{43}$ is H, $(C_{1-3})$haloalkyl or $(C_{1-3})$alkyl optionally mono-substituted with OH, —O—$(C_{1-3})$alkyl or —O—$(C_{3-5})$cycloalkyl.

In a further embodiment, the invention provides a compound of Formula (I) as defined above, or a pharmaceutically acceptable salt thereof, wherein Ring A is a 5- or 6-membered nitrogen containing heterocyclyl or heteroaryl, wherein Ring A is optionally mono- or di-substituted with $R^4$;

$R^4$ is each independently selected from the group consisting of $R^{42}$, $OR^{42}$ and $N(R^{43})R^{42}$;

$R^{42}$ is each independently selected from the group consisting of $(C_{1-6})$alkyl, —$(C_{1-6})$alkyl-$(C_{3-7})$cycloalkyl, $(C_{3-7})$cycloalkyl, heterocyclyl and heteroaryl, wherein each said alkyl, cycloalkyl, heterocyclyl and heteroaryl, either alone or in combination with another radical, is optionally substituted with 1 to 2 substituents each independently selected from the group consisting of: halo, oxo, cyano, OH, —COOH, —O—$(C_{1-4})$alkyl, $(C_{3-7})$cycloalkyl, $(C_{1-4})$haloalkyl, —$SO_2NH_2$, —$SO_2$—$NH(C_{1-4})$alkyl, —$SO_2$—$N((C_{1-4})$alkyl$)_2$, —$SO(C_{1-4})$alkyl, —$SO_2(C_{1-4})$alkyl, —$C(=O)$—$NH_2$, —$C(=O)$—$NH(C_{1-4})$alkyl, —$C(=O)$—$N((C_{1-4})$alkyl$)_2$, —$NH_2$, —$NH(C_{1-4})$alkyl, —$N((C_{1-4})$alkyl$)_2$, —NH—C$(=O)(C_{1-4})$alkyl and $(C_{1-4})$alkyl optionally mono- or di-substituted with OH or —O—$(C_{1-4})$alkyl;

$R^{43}$ is H or $(C_{1-3})$alkyl.

In a further embodiment, the invention provides a compound of Formula (I) as defined above, or a pharmaceutically acceptable salt thereof, wherein $R^5$ is H, —O—$(C_{1-4})$alkyl, —$NH_2$ or —$NH(C_{1-4})$alkyl.

In a further embodiment, the invention provides a compound of Formula (I) as defined above, or a pharmaceutically acceptable salt thereof, wherein $R^5$ is H or —O—$(C_{1-4})$alkyl.

In a further embodiment, the invention provides a compound of Formula (I) as defined above, or a pharmaceutically acceptable salt thereof, wherein $R^5$ is H.

Another aspect of this invention provides a compound as defined above, or a pharmaceutically acceptable salt thereof, as a medicament.

Also within the scope of this invention is the use of a compound of Formula (I), or a pharmaceutically acceptable salt thereof, for the manufacture of a medicament for the treatment or prevention of CMV disease and/or infection in a human being.

Included within the scope of this invention is a pharmaceutical composition comprising a compound of Formula (I), or a pharmaceutically acceptable salt thereof, and a pharmaceutically acceptable carrier.

According to a further aspect of this embodiment the pharmaceutical composition according to this invention further comprises a therapeutically effective amount of at least one other antiviral agent.

The invention also provides the use of a pharmaceutical composition as described hereinabove for the treatment of a CMV infection in a human being having or at risk of having the infection.

The invention also provides the use of a pharmaceutical composition as described hereinabove for the treatment of CMV disease in a human being having or at risk of having the disease.

Another aspect of the invention involves a method of treating or preventing CMV disease and/or infection in a human being by administering to the human being an anti-CMV virally effective amount of a compound of the invention, a pharmaceutically acceptable salt thereof, or a composition as described above, alone or in combination with at least one other antiviral agent, administered together or separately.

An additional aspect of this invention refers to an article of manufacture comprising a composition effective to treat CMV disease and/or infection; and packaging material comprising a label which indicates that the composition can be used to treat disease and/or infection by CMV; wherein the composition comprises a compound of formula (I) according to this invention or a pharmaceutically acceptable salt thereof.

Still another aspect of this invention relates to a method of inhibiting the replication of CMV comprising exposing the virus to an effective amount of the compound of formula (I), or a salt thereof, under conditions where replication of CMV is inhibited.

Further included in the scope of the invention is the use of a compound of formula (I), or a salt thereof, to inhibit the replication of CMV.

DETAILED DESCRIPTION OF PREFERRED EMBODIMENTS

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the first named subgroup is the radical attachment point, for example, the substituent "—$C_{1-3}$-alkyl-aryl" means an aryl group which is bound to a $C_{1-3}$-alkyl-group, with the $C_{1-3}$-alkyl group bound to the core. Unless specifically stated otherwise, for groups comprising two or more subgroups, the substituent may be attached to either subgroup. Substituents contemplated in the context of a specific molecule or fragment thereof are those which give rise to chemically stable compounds, such as are recognized by those skilled in the art.

In case a compound of the present invention is depicted in the form of a chemical name and as a formula in case of any discrepancy the formula shall prevail. An asterisk or the designation, ----, may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers, atropisomers) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

One skilled in the art would know how to separate, enrich, or selectively prepare the enantiomers of the compounds of the present invention. Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include but not limited to chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, including but not limited to GC, HPLC, CE, or NMR, and assignment of absolute configuration and conformation, including but not limited to CD, ORD, X-ray crystallography, or NMR.

The term "halo" generally denotes fluorine, chlorine, bromine and iodine. The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-3}$-alkyl embraces the radicals $H_3C$—, $H_3C$—$CH_2$—, $H_3C$—$CH_2$—$CH_2$— and $H_3C$—$CH(CH_3)$—.

The term "$C_{1-n}$-alkylidene", is used for a group as defined in the definition for "$C_{1-n}$-alkyl" wherein divalent group is formed by removal of two hydrogen atoms from the same carbon atom, the free valencies of which are part of a double bond.

The term "$C_{2-n}$-alkenyl", is used for a group as defined in the definition for "$C_{1-n}$-alkyl" with at least two carbon atoms, if at least two of those carbon atoms of said group are bonded to each other by a double bond.

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

The term "carbocyclyl" or "carbocycle" as used herein, either alone or in combination with another radical, means a mono-, bi- or tricyclic ring structure consisting of 3 to 14 carbon atoms. The term "carbocyclyl" or "carbocycle" refers to fully saturated and aromatic ring systems and partially saturated ring systems. The term "carbocyclyl" or "carbocycle" encompasses fused, bridged and spirocyclic systems.

The term "$C_{3-n}$-cycloalkyl", wherein n is an integer 4 to n, either alone or in combination with another radical, denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to at least one other 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring system including aromatic ring systems containing one or more heteroatoms selected from N, O or S(O)$_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms and all spiro, bridged and fused systems. Thus, the term "heterocyclyl" or "heterocyclyl" includes the following exemplary structures which are not depicted as radicals as each form may be attached through a covalent bond to any atom so long as appropriate valences are maintained:

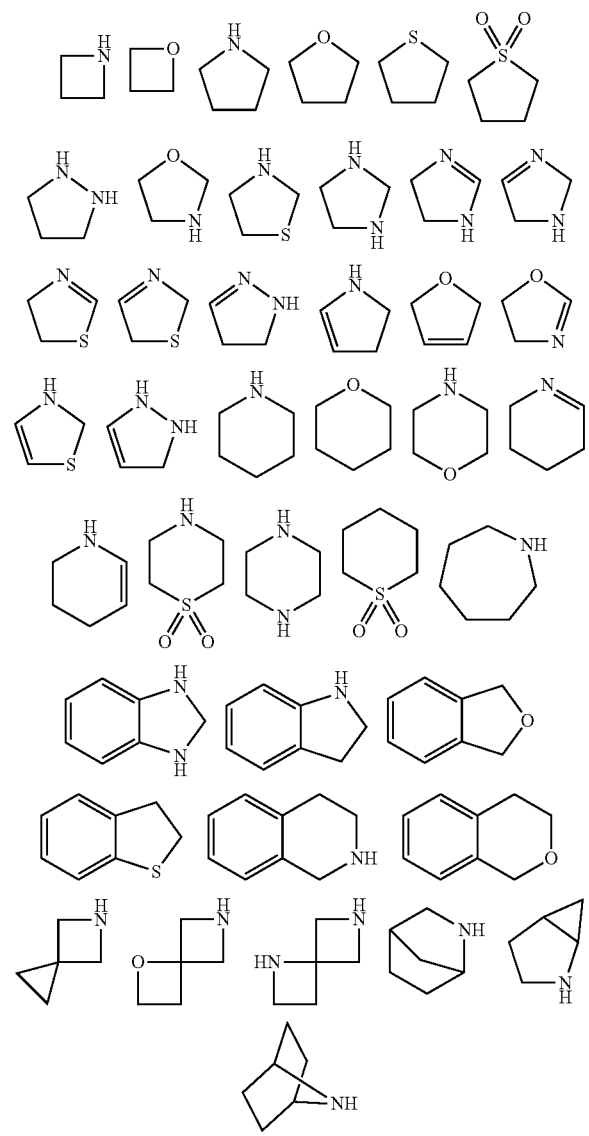

The term "heteroaryl" means a mono- or polycyclic-ring system containing one or more heteroatoms selected from N, O or S(O)$_r$, wherein r=0, 1 or 2, consisting of 5 to 14 ring atoms wherein at least one of the heteroatoms is part of an aromatic ring. The term "heteroaryl" is intended to include all the possible isomeric forms and all spiro, bridged and fused systems. Thus, the term "heteroaryl" includes the following exemplary structures which are not depicted as radicals as each form may be attached through a covalent bond to any atom so long as appropriate valences are maintained:

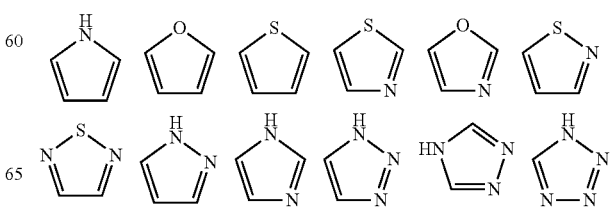

-continued

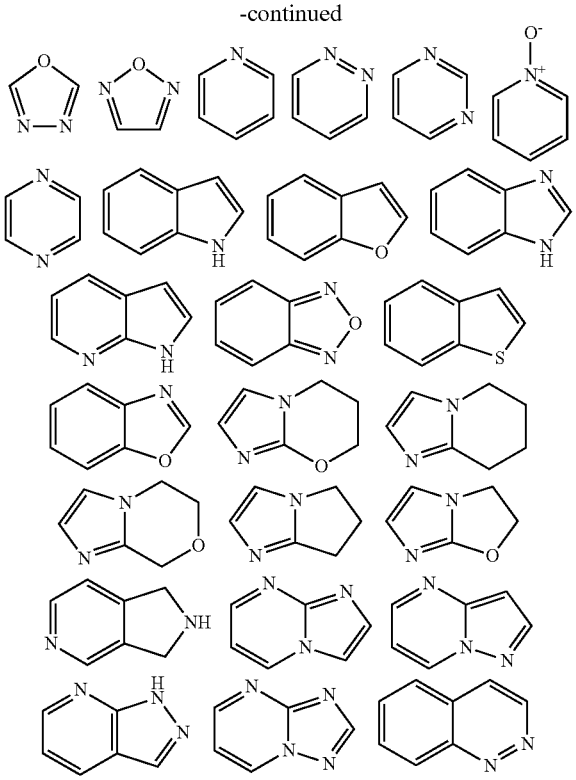

Many of the terms given above may be used repeatedly in the definition of a formula or group and in each case have one of the meanings given above, independently of one another.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromideshydrobromides, Ca-edetatesedetates, camsylates, carbonates, chlorideshydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

As used herein, the term "treatment" means the administration of a compound or composition according to the present invention to alleviate or eliminate symptoms of CMV disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, to prevent the appearance of symptoms of the disease.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Further Embodiments

In the following embodiments, groups and substituents of the compounds of Formula (I) according to this invention are described in detail.

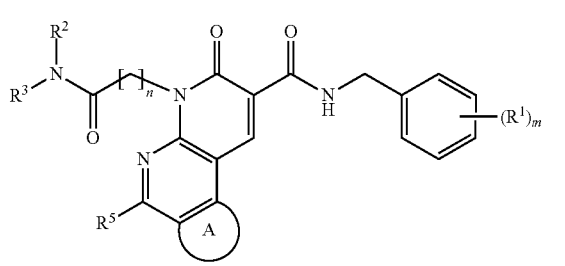

Any and each of the definitions below may be combined with each other.

n:
n-A: n is 1, 2 or 3.
n-B: n is 1 or 2.
n-C: n is 1.
m:
m-A: m is 1, 2 or 3.
m-B: m is 1 or 2.
m-C: m is 1.
$R^1$:
$R^1$-A: $R^1$ is halo, —CN, $(C_{1-6})$alkyl, OH, —O—$(C_{1-6})$alkyl, $(C_{1-6})$haloalkyl or nitro.
$R^1$-B: $R^1$ is F, Cl, Br, —CN, OH, O—$(C_{1-3})$alkyl, $(C_{1-3})$alkyl, $(C_{1-3})$haloalkyl or nitro.
$R^1$-C: $R^1$ is F, Cl, Br, —CN, OH or O—$(C_{1-3})$alkyl.
$R^2R^3$:
$R^2/R^3$-A: $R^2$ is H or $(C_{1-6})$alkyl optionally substituted with halo, —CN, —$(C_{3-7})$cycloalkyl, —O—$(C_{1-6})$alkyl, OH, —$NH_2$, —$NH(C_{1-6})$alkyl or —$N((C_{1-6})$alkyl$)_2$;
$R^3$ is H, $(C_{1-6})$alkyl, $(C_{3-7})$cycloalkyl, aryl, heterocyclyl, heteroaryl, —$(C_{1-6})$alkyl-$(C_{3-7})$cycloalkyl, —$(C_{1-6})$alkyl-aryl, —$(C_{1-6})$alkyl-heterocyclyl or —$(C_{1-6})$alkyl-heteroaryl, wherein each said alkyl, cycloalkyl, aryl, heterocyclyl and heteroaryl, either alone or in combination with another radical, is optionally mono-, di-, or tri-substituted with $R^{32}$;
or $R^2$ and $R^3$, together with the N to which they are attached, are linked to form a heterocyclyl or heteroaryl; wherein said heterocyclyl and heteroaryl are optionally mono-, di-, or tri-substituted with $R^{32}$;
$R^{32}$ is each independently selected from the group consisting of $R^{33}$, halo, oxo, —CN, OH, SH, —COOH, —$(C_{1-6})$alkyl; —O—$(C_{1-6})$alkyl, —S—$(C_{1-6})$alkyl, $(C_{3-7})$cycloalkyl, $(C_{1-6})$haloalkyl, —C(=O)—O—$(C_{1-6})$alkyl, —$SO_2NH_2$, —$SO_2$—$NH(C_{1-6})$alkyl, —$SO_2$—$N((C_{1-6})$alkyl$)_2$, —$SO(C_{1-6})$alkyl, —$SO_2(C_{1-6})$alkyl, —C(=O)—$NH_2$, —C(=O)—$NH(C_{1-6})$alkyl, —C(=O)—$N((C_{1-6})$alkyl$)_2$, —C(=O)—NH—$SO_2(C_{1-6})$alkyl, —$SO_2$—NH—C(=O)—$(C_{1-6})$alkyl, —$NH_2$, —$NH(C_{1-6})$alkyl, —$N((C_{1-6})$alkyl$)_2$, —$NH(C_{3-7})$cycloalkyl, —$N((C_{1-6})$alkyl$)(C_{3-7})$cycloalkyl, —NH—C(=O)$(C_{1-6})$alkyl, —NH—C(=O)O$(C_{1-6})$alkyl, heterocyclyl (optionally substituted with $(C_{1-6})$alkyl) and heteroaryl (optionally substituted with $(C_{1-6})$alkyl);
$R^{33}$ is $(C_{1-6})$alkyl optionally mono- or di-substituted with OH, —O—$(C_{1-6})$alkyl, —$NH_2$, —$NH(C_{1-6})$alkyl or —$N((C_{1-6})$alkyl$)_2$.
$R^2/R^3$-B: $R^2$ is H or $(C_{1-6})$alkyl;
$R^3$ is $(C_{1-6})$alkyl, —$(C_{1-6})$alkyl-$(C_{3-7})$cycloalkyl, —$(C_{1-6})$alkyl-aryl, —$(C_{1-6})$alkyl-heterocyclyl or —$(C_{1-6})$alkyl-heteroaryl, wherein each said alkyl, cycloalkyl, aryl, heterocyclyl and heteroaryl, either alone or in combination with another radical, is optionally mono-, di-, or tri-substituted with $R^{32}$; or
$R^2$ and $R^3$, together with the N to which they are attached, are linked to form a heterocyclyl; wherein said heterocyclyl is optionally mono-, di-, or tri-substituted with $R^{32}$;
$R^{32}$ is each independently selected from the group consisting of $R^{33}$, halo, oxo, —CN, OH, —COOH, —$(C_{1-6})$alkyl, —O—$(C_{1-6})$alkyl, $(C_{3-7})$cycloalkyl, $(C_{1-6})$haloalkyl, —C(=O)—O—$(C_{1-6})$alkyl, —$SO_2NH_2$, —$SO_2$—$NH(C_{1-6})$alkyl, —$SO_2$—$N((C_{1-6})$alkyl$)_2$, —$SO(C_{1-6})$alkyl, —$SO_2(C_{1-6})$alkyl, —C(=O)—$NH_2$, —C(=O)—$NH(C_{1-6})$alkyl, —C(=O)—$N((C_{1-6})$alkyl$)_2$, —C(=O)—NH—$SO_2(C_{1-6})$alkyl, —$SO_2$—NH—C(=O)—$(C_{1-6})$alkyl, heterocyclyl (optionally substituted with $(C_{1-6})$alkyl) and heteroaryl (optionally substituted with $(C_{1-6})$alkyl);

$R^{33}$ is $(C_{1-6})$alkyl optionally mono- or di-substituted with OH, —O—$(C_{1-6})$alkyl, —$NH_2$, —$NH(C_{1-6})$alkyl or —$N((C_{1-6})$alkyl$)_2$.
$R^2/R^3$-C: $R^2$ and $R^3$, together with the N to which they are attached, are linked to form a heterocyclyl; wherein said heterocyclyl is optionally mono- or di-substituted with $R^{32}$;
$R^{32}$ is each independently selected from the group consisting of $R^{33}$, halo, oxo, —CN, OH, —COOH, —$(C_{1-6})$alkyl, —O—$(C_{1-6})$alkyl, $(C_{3-7})$cycloalkyl, $(C_{1-6})$haloalkyl, —C(=O)—O—$(C_{1-6})$alkyl, —$SO_2NH_2$, —$SO_2$—$NH(C_{1-6})$alkyl, —$SO_2$—$N((C_{1-6})$alkyl$)_2$, —$SO(C_{1-6})$alkyl, —$SO_2(C_{1-6})$alkyl, —C(=O)—$NH_2$, —C(=O)—$NH(C_{1-6})$alkyl, —C(=O)—$N((C_{1-6})$alkyl$)_2$, —C(=O)—NH—$SO_2(C_{1-6})$alkyl, —$SO_2$—NH—C(=O)—$(C_{1-6})$alkyl, heterocyclyl (optionally substituted with $(C_{1-6})$alkyl) and heteroaryl (optionally substituted with $(C_{1-6})$alkyl);
$R^{33}$ is —$(C_{1-6})$alkyl optionally mono- or di-substituted with OH, —O—$(C_{1-6})$alkyl, —$NH_2$, —$NH(C_{1-6})$alkyl or —$N((C_{1-6})$alkyl$)_2$.
$R^2/R^3$-D: $R^2$ and $R^3$, together with the N to which they are attached, are linked to form a heterocyclyl, wherein said heterocyclyl is optionally mono- or di-substituted with $R^{32}$;
$R^{32}$ is each independently selected from the group consisting of $R^{33}$, —CN, $(C_{1-6})$haloalkyl, halo and —$O(C_{1-6})$alkyl;
$R^{33}$ is $(C_{1-6})$alkyl optionally mono- or di-substituted with OH.
Ring A:
Ring A-A: Ring A is heterocyclyl or heteroaryl, wherein Ring A is optionally mono-, di-, or tri-substituted with $R^4$;
$R^4$ is each independently selected from the group consisting of halo, oxo, cyano, nitro, $(C_{1-6})$alkylidene, $R^{42}$, —C(=O)—$R^{42}$, —C(=O)$OR^{42}$, —$OR^{42}$, —$SR^{42}$, —$SOR^{42}$, —$SO_2R^{42}$, —$N(R^{43})R^{42}$, —$(C_{1-6})$alkyl-$N(R^{43})R^{42}$, —C(=O)—$N(R^{43})R^{42}$, —$N(R^{43})$—C(=O)$R^{42}$, —$N(R^{43})$—C(=O)O—$R^{42}$, —C(=O)—N(H)—$SO_2R^{42}$, —$SO_2$—N(H)—C(=O)$R^{42}$, —O—C(=O)—$N(R^{43})R^{42}$ and —$SO_2$—$N(R^{43})R^{42}$;
$R^{42}$ is each independently selected from the group consisting of H, $(C_{1-6})$alkyl, $(C_{2-6})$alkenyl, $(C_{2-6})$alkynyl, —$(C_{1-6})$alkyl-$(C_{3-7})$cycloalkyl, —$(C_{1-6})$alkyl-aryl, —$(C_{1-6})$alkyl-heterocyclyl, —$(C_{1-6})$alkyl-heteroaryl, $(C_{3-7})$cycloalkyl, aryl, heterocyclyl and heteroaryl, wherein each said alkyl, alkenyl, alkynyl, cycloalkyl, aryl, heterocyclyl and heteroaryl, either alone or in combination with another radical, is optionally substituted with 1 to 3 substituents each independently selected from the group consisting of: halo, cyano, OH, —COOH, —O—$(C_{1-6})$alkyl, —S—$(C_{1-6})$alkyl, $(C_{3-7})$cycloalkyl, —O—$(C_{3-7})$cycloalkyl, $(C_{1-6})$haloalkyl, —C(=O)—$(C_{1-6})$alkyl, —C(=O)—O—$(C_{1-6})$alkyl, —$SO_2NH_2$, —$SO_2$—$NH(C_{1-6})$alkyl, —$SO_2$—$N((C_{1-6})$alkyl$)_2$, —$SO(C_{1-6})$alkyl, —$SO_2(C_{1-6})$alkyl, —C(=O)—$NH_2$, —C(=O)—$NH(C_{1-6})$alkyl, —C(=O)—$N((C_{1-6})$alkyl$)_2$, —C(=O)—N(H)—$SO_2(C_{1-6})$alkyl, —$SO_2$—N(H)—C(=O)$(C_{1-6})$alkyl, —$NH_2$, —$NH(C_{1-6})$alkyl, —$N((C_{1-6})$alkyl$)_2$, —NH—C(=O)$(C_{1-6})$alkyl, —NH—C(=O)—O$(C_{1-6})$alkyl and $(C_{1-6})$alkyl optionally mono- or di-substituted with OH, —O—$(C_{1-6})$alkyl, —S—$(C_{1-6})$alkyl, —$SO(C_{1-6})$alkyl, —$SO_2(C_{1-6})$alkyl, heterocyclyl or heteroaryl;
$R^{43}$ is H, $(C_{1-6})$haloalkyl or $(C_{1-6})$alkyl optionally mono- or di-substituted with OH, —O—$(C_{1-6})$alkyl or —O—$(C_{3-7})$cycloalkyl.
Ring A-B: Ring A is a nitrogen containing heterocyclyl or heteroaryl, wherein Ring A is optionally mono-, di-, or tri-substituted with $R^4$;
$R^4$ is each independently selected from the group consisting of halo, oxo, cyano, $R^{42}$, —C(=O)$OR^{42}$, —$OR^{42}$, —$N(R^{43})R^{42}$ and —$(C_{1-6})$alkyl-$N(R^{43})R^{42}$;

$R^{42}$ is each independently selected from the group consisting of H, $C_{1-6}$alkyl, —$(C_{1-6})$alkyl-$(C_{3-7})$cycloalkyl, —$(C_{1-6})$alkyl-aryl, —$(C_{1-6})$alkyl-heterocyclyl, —$(C_{1-6})$alkyl-heteroaryl, $(C_{3-7})$cycloalkyl, aryl, heterocyclyl and heteroaryl, wherein each said alkyl, cycloalkyl, aryl, heterocyclyl and heteroaryl, either alone or in combination with another radical, is optionally substituted with 1 to 2 substituents each independently selected from the group consisting of: halo, oxo, cyano, OH, —COOH, —O—$(C_{1-6})$alkyl, —S—$(C_{1-6})$alkyl, $(C_{3-7})$cycloalkyl, $(C_{1-6})$haloalkyl, —C(=O)—O—$(C_{1-6})$alkyl, —SO$_2$NH$_2$, SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl$)_2$, —NH$_2$, —NH$(C_{1-6})$alkyl, —N$((C_{1-6})$alkyl$)_2$, —NH—C(=O)$(C_{1-6})$alkyl and $(C_{1-6})$alkyl optionally mono- or di-substituted with OH or —O—$(C_{1-6})$alkyl;

$R^{43}$ is H, $(C_{1-3})$haloalkyl or $(C_{1-3})$alkyl optionally mono- or di-substituted with OH, —O—$(C_{1-3})$alkyl or —O—$(C_{3-5})$cycloalkyl.

Ring A-C: Ring A is a nitrogen containing heterocyclyl or heteroaryl, wherein Ring A is optionally mono- or di-substituted with $R^4$;

$R^4$ is each independently selected from the group consisting of $R^{42}$, OR$^{42}$ and N(R$^{43}$)R$^{42}$;

$R^{42}$ is each independently selected from the group consisting of $(C_{1-6})$alkyl, —$(C_{1-6})$alkyl-$(C_{3-7})$cycloalkyl, $(C_{3-7})$cycloalkyl, heterocyclyl and heteroaryl, wherein each said alkyl, cycloalkyl, heterocyclyl and heteroaryl, either alone or in combination with another radical, is optionally substituted with 1 to 2 substituents each independently selected from the group consisting of: halo, oxo, cyano, OH, —COOH, —O—$(C_{1-4})$alkyl, $(C_{3-7})$cycloalkyl, $(C_{1-4})$haloalkyl, —SO$_2$NH$_2$, —SO$_2$—NH$(C_{1-4})$alkyl, —SO$_2$—N$((C_{1-4})$alkyl$)_2$, —SO$(C_{1-4})$alkyl, —SO$_2(C_{1-4})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$, —NH—C(=O)$(C_{1-4})$alkyl and $(C_{1-4})$alkyl optionally mono- or di-substituted with OH or —O—$(C_{1-4})$alkyl;

$R^{43}$ is H, $(C_{1-3})$haloalkyl or $(C_{1-3})$alkyl optionally mono-substituted with OH, —O—$(C_{1-3})$alkyl, —O—$(C_{3-5})$cycloalkyl.

Ring A-D: Ring A is a 5- or 6-membered nitrogen containing heterocyclyl or heteroaryl, wherein Ring A is optionally mono- or di-substituted with $R^4$;

$R^4$ is each independently selected from the group consisting of $R^{42}$, OR$^{42}$ and N(R$^{43}$)R$^{42}$;

$R^{42}$ is each independently selected from the group consisting of $(C_{1-6})$alkyl, —$(C_{1-6})$alkyl-$(C_{3-7})$cycloalkyl, $(C_{3-7})$cycloalkyl, heterocyclyl and heteroaryl, wherein each said alkyl, cycloalkyl, heterocyclyl and heteroaryl, either alone or in combination with another radical, is optionally substituted with 1 to 2 substituents each independently selected from the group consisting of: halo, oxo, cyano, OH, —COOH, —O—$(C_{1-4})$alkyl, $(C_{3-7})$cycloalkyl, $(C_{1-4})$haloalkyl, —SO$_2$NH$_2$, —SO$_2$—NH$(C_{1-4})$alkyl, —SO$_2$—N$((C_{1-4})$alkyl$)_2$, —SO$(C_{1-4})$alkyl, —SO$_2(C_{1-4})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$, —NH—C(=O)$(C_{1-4})$alkyl and $(C_{1-4})$alkyl optionally mono- or di-substituted with OH or —O—$(C_{1-4})$alkyl;

$R^{43}$ is H or $(C_{1-3})$alkyl.

$R^5$:

$R^5$-A: $R^5$ is H, halo, —CN, $(C_{1-6})$alkyl, $(C_{1-6})$haloalkyl, —O—$(C_{1-6})$alkyl, $(C_{3-7})$cycloalkyl, —NH$_2$, —NH$(C_{1-6})$alkyl or —N$((C_{1-6})$alkyl$)_2$.

$R^5$-B: $R^5$ is H, —O—$(C_{1-4})$alkyl, —NH$_2$ or —NH$(C_{1-4})$alkyl.

$R^5$-C: $R^5$ is H or —O—$(C_{1-4})$alkyl.

$R^5$-D: $R^5$ is H.

Representative embodiments of the compound aspects of the present invention are described above. Further subgeneric embodiments of the present invention are set forth in the following table, wherein each substituent group of each embodiment is defined according to the definitions set forth above:

| Embodiment | Ring A | n | m | $R^1$ | $R^2/R^3$ | $R^5$ |
|---|---|---|---|---|---|---|
| E-1 | Ring A-B | n-A | m-A | $R^1$-A | $R^2/R^3$-C | $R^5$-A |
| E-2 | Ring A-B | n-A | m-A | $R^1$-A | $R^2/R^3$-B | $R^5$-A |
| E-3 | Ring A-B | n-B | m-C | $R^1$-B | $R^2/R^3$-B | $R^5$-D |
| E-4 | Ring A-C | n-C | m-C | $R^1$-C | $R^2/R^3$-D | $R^5$-D |
| E-5 | Ring A-C | n-A | m-A | $R^1$-A | $R^2/R^3$-D | $R^5$-A |
| E-6 | Ring A-C | n-B | m-B | $R^1$-A | $R^2/R^3$-C | $R^5$-B |
| E-7 | Ring A-C | n-B | m-B | $R^1$-A | $R^2/R^3$-C | $R^5$-C |
| E-8 | Ring A-C | n-C | m-C | $R^1$-C | $R^2/R^3$-C | $R^5$-D |
| E-9 | Ring A-C | n-B | m-C | $R^1$-B | $R^2/R^3$-B | $R^5$-D |
| E-10 | Ring A-C | n-C | m-C | $R^1$-B | $R^2/R^3$-B | $R^5$-D |
| E-11 | Ring A-D | n-C | m-C | $R^1$-C | $R^2/R^3$-D | $R^5$-D |
| E-12 | Ring A-D | n-A | m-A | $R^1$-A | $R^2/R^3$-D | $R^5$-B |
| E-13 | Ring A-D | n-B | m-B | $R^1$-A | $R^2/R^3$-C | $R^5$-B |
| E-14 | Ring A-D | n-A | m-A | $R^1$-A | $R^2/R^3$-D | $R^5$-C |
| E-15 | Ring A-D | n-B | m-B | $R^1$-A | $R^2/R^3$-C | $R^5$-C |
| E-16 | Ring A-D | n-B | m-B | $R^1$-A | $R^2/R^3$-C | $R^5$-B |
| E-17 | Ring A-D | n-B | m-B | $R^1$-A | $R^2/R^3$-B | $R^5$-C |

Examples of most preferred compounds according to this invention are each single compound listed in Tables 1 to 5.

Pharmaceutical Composition

Suitable preparations for administering the compounds of the invention will be apparent to those with ordinary skill in the art and include for example tablets, pills, capsules, suppositories, lozenges, troches, solutions, syrups, elixirs, sachets, injectables, inhalatives and powders. The content of the pharmaceutically active compound(s) should be in the range from 0.05 to 90 wt.-%, preferably 0.1 to 50 wt.-% of the composition as a whole.

Suitable tablets may be obtained, for example, by mixing one or more compounds according to the invention with known excipients, for example inert diluents, carriers, disintegrants, adjuvants, surfactants, binders and/or lubricants. The tablets may also consist of several layers.

Suitable injectables may be obtained, for example, by mixing one or more compounds according to the invention with known excipients, for example inert diluents, carriers, co-solvent, adjuvants, surfactants and/or cyclodextrin complex. The injectable formulation may be an emulsion or suspension.

Combination Therapy

Combination therapy is contemplated wherein a compound of the invention, or a pharmaceutically acceptable salt thereof, is co-administered with at least one additional agent selected from: a CMV entry inhibitor, a CMV early transcription event inhibitor, a CMV helicase-primase inhibitor, an other CMV DNA polymerase inhibitor, an inhibitor of UL97 kinase, a CMV protease inhibitor, a CMV terminase inhibitor, a CMV maturation inhibitor, an inhibitor of another target in the CMV life cycle, a CMV vaccine and a CMV biological agent.

These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of the invention, or a pharmaceutically acceptable salt thereof.

The dose range of the compounds of the invention applicable per day is usually from 0.01 to 100 mg/kg of body weight, preferably from 0.1 to 50 mg/kg of body weight. Each dosage unit may conveniently contain from 5% to 95% active compound (w/w). Preferably such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

When the composition of this invention comprises a combination of a compound of the invention and one or more additional therapeutic or prophylactic agent, both the compound and the additional agent should be present at dosage levels of between about 10 to 100%, and more preferably between about 10 and 80% of the dosage normally administered in a monotherapy regimen.

Antiviral agents contemplated for use in such combination therapy include agents (compounds or biologicals) that are effective to inhibit the formation and/or replication of a virus in a human being, including but not limited to agents that interfere with either host or viral mechanisms necessary for the formation and/or replication of a virus in a human being. Such agents can be selected from: a CMV entry inhibitor; a CMV early transcription event inhibitor; a CMV helicase-primase inhibitor; a CMV DNA polymerase inhibitor such as Ganciclovir (Cytovene), Valganciclovir (Valcyte; Cymeval), Cidofovir (Vistide), Foscarnet (Foscavir), CMX001, cyclopropavir (MBX-400) and Valaciclovir (Valtrex; Zelitrex); an inhibitor of UL97 kinase such as Maribavir; a CMV protease inhibitor; a CMV terminase inhibitor such as AIC246 (Letermovir); a CMV maturation inhibitor; other inhibitors such as Artesunate; a CMV vaccine such as TransVax and a CMV biological agent such as Cytogam (Cytotect).

EXAMPLES

Other features of the present invention will become apparent from the following non-limiting examples which illustrate the principles of the invention. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. The reactants used in the examples below may be obtained either as described herein, or if not described herein, are themselves either commercially available or may be prepared from commercially available materials by methods known in the art. Flash chromatography is carried out on silica gel ($SiO_2$) according to the procedure of W. C. Still et al., J. Org. Chem., (1978), 43, 2923. Mass spectral analyses may be recorded using an electrospray mass spectrometer.

Compounds and intermediates can be purified by a Teledyne ISCO Combiflash $R_f$ System at 254 nm using commercial normal phase silica 4-120 g Redisep $R_f$ or Silicycle columns at a flow rate of 18-85 mL/min depending on column size. Mass spectral analyses may be recorded using flow injection analysis mass spectrometry or Waters Acquity Ultraperformance LC System consisting of a sample organizer, PDA detector, column manager, sample manager, binary solvent manager and SQ detector.

Reactions performed in microwave conditions are conducted in a Biotage Initiator 2.0 microwave synthesizer equipped with a Robot Sixty for vial manipulations. The temperature range is from 40-250° C. The pressure range is from 0-20 bar and the power range is from 0-400 Watts at 2.45 GHz. The vial size varies from 0.5 mL to 20 mL. The solvent absorption level is high by default. Specific reaction times and temperatures are given in the experimental section when applicable.

Preparative RP-HPLC is performed under standard conditions using one of the following specific measuring conditions:

A) Waters SunFire Prep OBD C18 column (5 μm, 19×50 mm) eluting firstly with a hold period of 1 min in initial gradient condition then eluting with a linear MeOH gradient containing 10 mM Ammonium Formate (pH 3.8) over 10 min at 30 mL/min. Fractions containing the desired product are pooled, concentrated and lyophilized.

B) Waters XBridge Prep OBD C18 column (5 μm, 19×50 mm) eluting firstly with a hold period of 1 min in initial gradient condition then eluting with a linear MeOH gradient containing 10 mM Ammonium Bicarbonate (pH 10.0) over 10 min at 30 mL/min. Fractions containing the desired product are pooled, concentrated and lyophilized.

C) Waters SunFire Prep OBD C18 column (5 μm, 19×50 mm) eluting firstly with a hold period of 1 min in initial gradient condition then eluting with a linear MeCN gradient containing 0.06% TFA (v/v) over 10 min at 30 mL/min. Fractions containing the desired product are pooled and lyophilized.

D) Waters XBridge Prep OBD C18 column (5 μm, 19×50 mm) eluting firstly with a hold period of 1 min in initial gradient condition then eluting with a linear MeCN gradient containing 10 mM Ammonium Bicarbonate (pH 10.0) over 10 min at 30 mL/min. Fractions containing the desired product are pooled and lyophilized.

E) Waters SunFire Prep OBD C18 column (5 μm, 19×50 mm) eluting firstly with a hold period of 0.5 min in initial gradient condition then eluting with a linear MeCN gradient containing 10 mM Ammonium Formate (pH 3.8) over 6.9 min at 45 mL/min. The eluents are warmed at 45° C. using a Timberline Instrument TL600 Mobile Phase Heater during the whole run. Fractions containing the desired product are pooled and lyophilized.

F) Waters XSelect Prep CSH OBD C18 column (5 μm, 30×75 mm) eluting firstly with a hold period of 0.5 min in initial gradient condition then eluting with a linear MeCN gradient containing 0.1% formic acid (v/v) over 6.4 min at 60 mL/min. The eluents are warmed at 45° C. using a Timberline Instrument TL600 Mobile Phase Heater during the whole run. Fractions containing the desired product are pooled and lyophilized.

Analytical UPLC is performed under standard conditions using one of the following specific measuring conditions:

A) Waters ACQUITY UPLC BEH C18 column (1.7 μm, 2.1×30 mm) eluting with a linear MeOH gradient containing 10 mM Ammonium Bicarbonate (pH 10) over 2.2 min at 0.75 mL/min.

B) Waters ACQUITY UPLC HSS C18 column (1.8 μm, 2.1×30 mm) eluting with a linear MeOH gradient containing 10 mM Ammonium Formate (pH 3.8) over 2.3 min at 0.8 mL/min.

C) Waters ACQUITY UPLC HSS C18 column (1.8 μm, 2.1×30 mm) eluting with a linear MeCN gradient containing 0.06% TFA (v/v) over 2.2 min at 0.9 mL/min.
D) Waters ACQUITY UPLC BEH C18 column (1.7 μm, 2.1×30 mm) eluting with a linear MeCN gradient containing 10 mM Ammonium Bicarbonate (pH 10) over 2.2 min at 0.75 mL/min.
E) Waters ACQUITY UPLC HSS C18 column (1.8 μm, 2.1×30 mm) eluting with a linear MeCN gradient containing 10 mM Ammonium Formate (pH 3.8) over 2.3 min at 0.8 mL/min. The eluents are warmed at 45° C. using a column preheater during the whole run.
F) Waters XSelect UPLC CSH C18 column (1.7 μm, 2.1×30 mm) eluting with a linear MeCN gradient containing 0.1% formic acid (v/v) over 2.0 min at 0.9 mL/min. The eluents are warmed at 45° C. using a column preheater during the whole run.

Abbreviations used in the examples include:

Ac: acetyl; AcOH: acetic acid; BEH: ethylene bridged hybrid; BOC or Boc: tert-butyloxycarbonyl; Bu: butyl; DAST: (diethylamino)sulfur trifluoride; DCE: 1,2-dichloroethane; DCM: dichloromethane; DIPEA: diisopropylethylamine; DMAc: dimethylacetamide; DMAP: 4-dimethylaminopyridine; DMEM: Dulbecco's modified Eagle's medium; DMF: N,N-dimethylformamide; DMSO: dimethylsulfoxide; dppf: 1,1'-diphenylphosphinylferrocene; EDCI: 1-[3-(dimethylamino)propyl]-3-ethylcarbodiimide hydrochloride; EDTA: ethylenediamine; eq or equiv; equivalents; tetraacetic acid; Et: ethyl; Et$_3$N: triethylamine; Et$_2$O: diethyl ether; EtOAc: ethyl acetate; EtOH: ethanol; HATU: [O-(7-azabenzotriazol-1-yl)-1,1,3,3-tetramethyluronium hexafluorophosphate]; HEPES: 4-(2-hydroxyethyl)-1-piperazineethanesulfonic acid; Hex: hexanes; HPLC: high performance liquid chromatography; HSS: high strength silica; $^i$Pr or i-Pr: 1-methylethyl (iso-propyl); IC$_{50}$: 50% inhibitory concentration; LiHMDS: lithium bis(trimethylsilyl)amide; Me: methyl; MeCN: acetonitrile; MeOH: methanol; MS: mass spectrometry; MTBE: methyl tert-butyl ether; [M+H]+: protonated molecular ion; NBS: N-bromosuccinimide; NMP: N-methyl pyrrolidinone; NMR: nuclear magnetic resonance spectroscopy; OBD: optimum bed density; PDA: photodiode array; Ph: phenyl; Pr: propyl; RP: reverse phase; RT: room temperature (18 to 22° C.); RuPhos: 2-dicyclohexylphosphino-2',6'-diisopropoxybiphenyl; TBAF: tetrabutylammonium fluoride; TEA: triethylamine; tert-butyl or t-butyl: 1,1-dimethylethyl; TFA: trifluoroacetic acid; THF: tetrahydrofuran; TMS: trimethylsilyl; TPAP: tetra-n-propyl ammonium perruthenate; t$_R$: retention time; UPLC: ultraperformance liquid chromatography; VSV: vesicular stomatitis virus.

Example 1

Preparation of Intermediate 1d

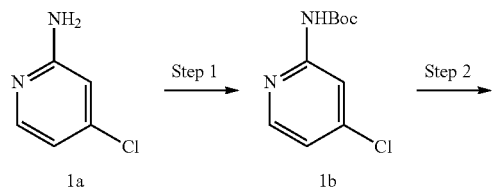

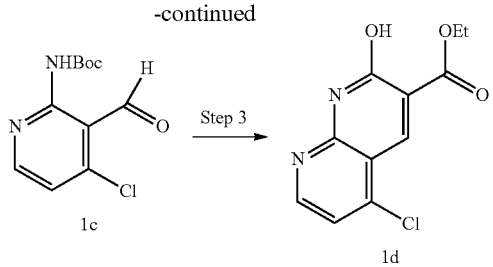

Step 1: In a 3-neck 5 L round bottom flask, a solution of sodium bis(trimethylsilyl)amide in THF (2.0 M, 400 mL, 800 mmol, 2.0 eq) is added to a cooled (−10° C.) solution of 2-amino-4-chloropyridine 1a (51 g, 400 mmol) in THF (1 L). A solution of di-tert-butyl dicarbonate (90 g, 400 mmol, 1.0 eq) in THF (500 mL) is then added at 5° C. The reaction mixture is stirred at RT for 16 h. The mixture is neutralized by the addition of a saturated aqueous solution of NH$_4$Cl (1 L). The layers are separated, and the aqueous phase is extracted with a saturated NH$_4$Cl solution (3×). The organic phases are combined and washed with brine. The solvent is removed in vacuo and the residue is washed with hexanes to afford intermediate 1b after collection by Buchner filtration. The filtrate is dried over anhydrous Na$_2$SO$_4$ and concentrated to give a second crop of intermediate 1b. The crops are combined and intermediate 1b is used in the next step without further purification.

Step 2: In a 4-neck 5 L round bottom flask fitted with an addition funnel, n-BuLi (2.5 M in hexanes, 125 mL, 313 mmol, 2.5 eq) is added over 30 min to a cooled (−78° C.) solution of 1b (28.54 g, 125 mmol, 1.0 eq). The resulting solution is stirred at −72 to −75° C. for 1 h. Neat DMF (48.4 mL, 625 mmol, 5 eq) is added via an addition funnel, keeping the temperature between −72 and −75° C. The reaction mixture is stirred at this temperature for 2 h, then it is quenched with a saturated aqueous solution of NH$_4$Cl (500 mL). This mixture is warmed to RT. The organic layer is separated and washed with a saturated NH$_4$Cl solution (5× 300 mL) until the resulting aqueous extract layer is pH~8. The organic layer is then washed with brine (2×250 mL), dried over anhydrous Na$_2$SO$_4$, and removed in vacuo. The crude product is purified by chromatography (5 to 40% EtOAc in hexanes) to give intermediate 1c.

Step 3: To a solution of 1c (1.86 g, 11.9 mmol) and diethyl malonate (3.82 g, 23.8 mmol) in anhydrous THF (60 mL) is added a solution of TiCl$_4$ (11.9 mL, 1 M in DCM, 11.9 mmol) at RT. The reaction mixture is stirred at RT for 4 h, then quenched with MeOH (2 mL). Stirring at RT is continued for 10 min, then water (20 mL) and EtOAc (20 mL) are added. This solution is stirred for 1 h. The resulting precipitate is filtered, washed with water and EtOAc, and dried under vacuum to give a first crop of intermediate 1d. The filtrate is stirred for 1 h and put aside for 15 h. The resulting precipitate is filtered, washed with water and EtOAc, and dried under vacuum to provide a second crop of intermediate 1d. Both crops are combined and intermediate 1d is used without further purification.

Example 2

Preparation of Intermediate 2f

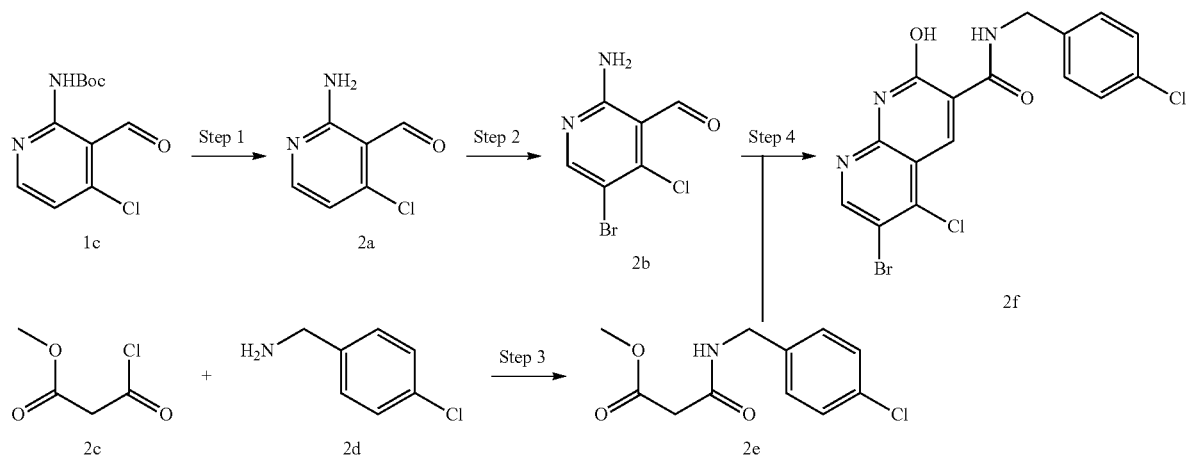

Step 1: TFA (102 mL, 1.32 mol) is added over 30 min to a cooled solution (0° C.) of 1c (68.0 g, 265 mmol) in DCM (800 mL). The mixture is stirred at RT for 21 h, and then the solvent is removed under reduced pressure. The residue is diluted in water (500 mL), cooled to 0° C., and neutralized with a saturated aqueous solution of sodium bicarbonate. The suspension is filtered, washed with water and dried under vacuum to provide intermediate 2a.

Step 2: To a slurry of 2a (37.9 g, 242 mmol) in anhydrous DCE (500 mL), NBS (47.3 g, 266 mmol) is added at RT, and the resulting slurry is stirred under reflux for 1 h. The reaction mixture is cooled to 0° C. and the solid is filtered and washed with DCE (200 mL) to give a first crop of crude intermediate 2b. The filtrate is concentrated under reduced pressure, and a second crop of intermediate 2b is collected by filtration and washed with DCE (100 mL). The crops are combined, and then intermediate 2b is rinsed once more with H$_2$O and DCE (100 mL+100 mL) and dried under vacuum to provide intermediate 2b.

Step 3: Methyl 3-chloro-3-oxopropanoate 2c (50.0 g, 366 mmol, Aldrich) is added over 30 min to a cooled solution (0° C.) of 4-chlorobenzylamine 2d (51.8 g, 366 mmol, Aldrich) and Et$_3$N (102.0 mL, 732 mmol, 2 eq) in dry DCM (1.5 L). The temperature inside the flask is kept below 10° C. during the addition of 2c. The resulting mixture is stirred at RT for 16 h, then washed with a saturated NaHCO$_3$ solution (~600 mL) and brine. The organic layer is separated, dried over Na$_2$SO$_4$ and concentrated under reduced pressure. The remaining solid is washed with 5% EtOAc in hexanes (~600 mL) and dried to give intermediate 2e.

Step 4: To a cooled solution (0° C.) of 2b (40.0 g, 170 mmol) and 2e (41.05 g, 170 mmol) in anhydrous THF (1.6 L) is added over a 1.5 h period a solution of TiCl$_4$ (1 M in DCM, 170 mL, 170 mmol, 1 eq). The resulting mixture is stirred at RT for 40 h. The reaction mixture is quenched by the addition of MeOH (100 mL) and stirred at RT for 20 min, then water (100 mL) is added and stirring is continued for 10 min. The precipitate is filtered, washed with water and MeOH, and dried under vacuum to provide compound 2f.

Example 2A

Preparation of Intermediate 8004

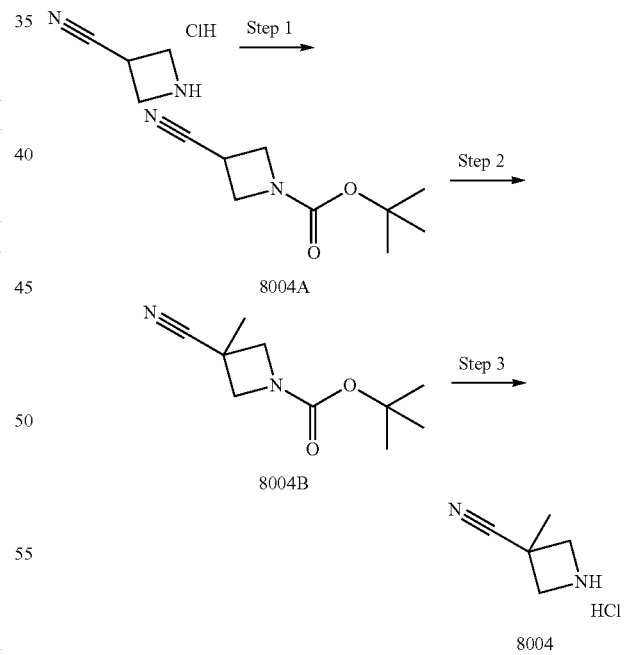

Step 1: To a stirred solution of 3-cyano azetidine hydrochloride (Oakwood) (10.0 g, 0.084 mol) in THF (100 mL) containing Et$_3$N (25.5 g, 0.252 mol, 3.0 eq) is added di-tert-butyl dicarbonate (27.6 g, 0.126 mol, 1.5 eq). The mixture is stirred at RT for 4 h, then water (100 mL) is added followed by EtOAc (50 mL). The aqueous phase is extracted with EtOAc (3× 50 mL). The organic layers are combined and washed with brine, dried over Na$_2$SO$_4$, filtered and concentrated. The crude residue is purified by silica gel flash chromatography (eluent: petroleum ether/EtOAc, 10%) to afford intermediate 8004A.

Step 2: To a stirred solution of 8004A (50.0 g, 0.274 mol) in THF (500 mL) at −78° C. is added a LiHMDS solution in THF (1 M; 330 mL, 0.330 mol, 1.2 eq). The mixture is stirred for 30 min, then methyliodide (122 g, 0.860 mol, 3.1 eq) is added and the mixture is stirred at RT for 60 min. The reaction mixture is neutralized at 0° C. by adding a saturated aqueous NH$_4$Cl solution (500 mL) and the aqueous layer is extracted with EtOAc (3×250 mL). The organic layers are combined, washed with brine, dried over Na$_2$SO$_4$, filtered and concentrated. The crude residue is purified by silica gel flash chromatography (eluent: petroleum ether/EtOAc, 10% to 15%) to afford intermediate 8004B.

Step 3: To a stirred solution of 8004B (30.0 g, 0.153 mol) in 1,4-dioxane (150 mL) at 0° C. is added a HCl solution in dioxane (4M; 150 mL, 0.60 mol, 3.9 eq) and the mixture is stirred at RT for 6 h. All volatiles are removed under reduced pressure. The crude residue is triturated in hexanes and collected by Buchner filtration to afford 8004 as the hydrochloride salt which is used without further purification.

Example 2B

Preparation of Intermediate 8005

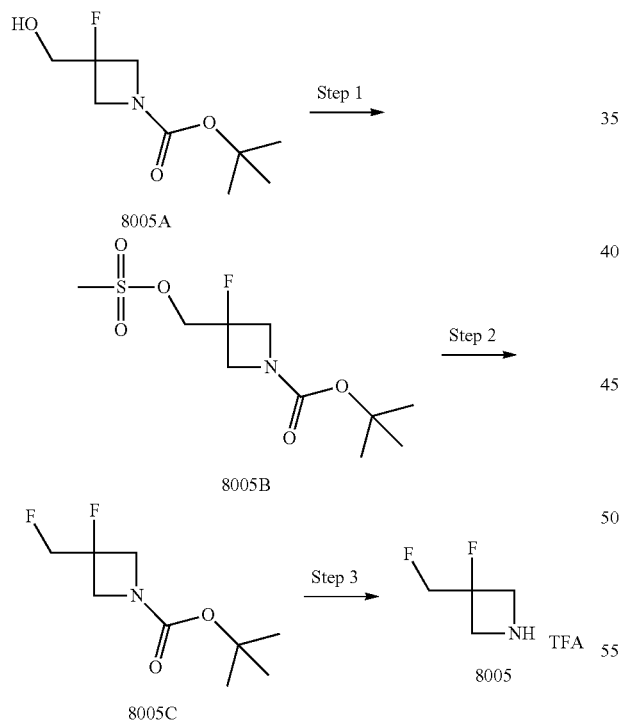

with DCM. The phases are separated and the aqueous layer is extracted with DCM (3×10 mL). The combined organic layers are dried over MgSO$_4$, filtered over a small plug of silica gel and concentrated to afford intermediate 8005B which is used without further purification.

Step 2: 8005B (434 mg, 2.67 mmol) is treated with a solution of TBAF in THF (1 M; 24.0 mL, 24.0 mmol, 9.0 eq) and heated to 65° C. for 1 h. The reaction mixture is concentrated to half of the volume and diluted with water. The aqueous layer is extracted with EtOAc (3×10 mL). The combined organic layers are washed with 0.25 M aqueous HCl followed by a saturated sodium bicarbonate solution, dried over MgSO$_4$, filtered and concentrated. The residue is purified by silica gel flash chromatography (10% to 25% EtOAc in hexanes) to provide intermediate 8005C.

Step 3: To 8005C (156 mg, 0.753 mmol) in DCM (2 mL) is added TFA (0.5 mL, 6.49 mmol, 8.6 eq) and the mixture is stirred at RT for 1 h. All volatiles are removed under reduced pressure to afford intermediate 8005 as the TFA salt which is used without further purification.

Example 2C

Preparation of Intermediate 8006

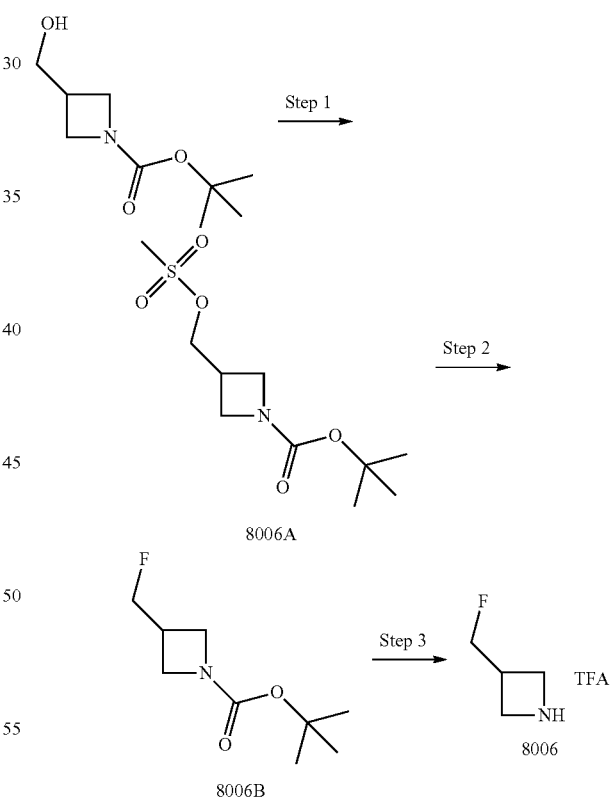

Step 1: A solution of intermediate 8005A (prepared analogously to the procedure in *J. Org. Chem.*, 74, 2009, 2250, herein incorporated by reference) (350 mg, 1.71 mmol) in DCM (10 mL) is treated with Et$_3$N (380 μL, 2.73 mmol, 1.6 eq) and cooled to 0° C. Methanesulfonyl chloride (198 μL, 2.56 mmol, 1.5 eq) is added and the reaction mixture is stirred at RT for 16 h. The reaction mixture is treated with a saturated aqueous sodium bicarbonate solution (10 mL) and diluted Step 1: A solution of tert-butyl 3-(hydroxymethyl)azetidine-1-carboxylate (Milestone) (500 mg, 2.67 mmol) in DCM (15 mL) is treated with Et$_3$N (595 μL, 4.27 mmol, 1.6 eq) and cooled to 0° C. Methanesulfonyl chloride (310 μL, 4.01 mmol, 1.5 eq) is added and the reaction mixture is stirred at RT for 16 h. The reaction mixture is treated with a saturated aqueous sodium bicarbonate solution and diluted with DCM. The phases are separated and the aqueous layer is extracted with DCM (3×10 mL). The organic layers are dried over MgSO$_4$, filtered over a small plug of silica gel and concentrated to afford intermediate 8006A which is used without further purification.

Step 2: Intermediate 8006B is prepared analogously to the procedure described in example 2B, step 2.

Step 3: Intermediate 8006 is prepared analogously to the procedure described in example 2B, step 3.

Example 2D

Preparation of Intermediate 8007

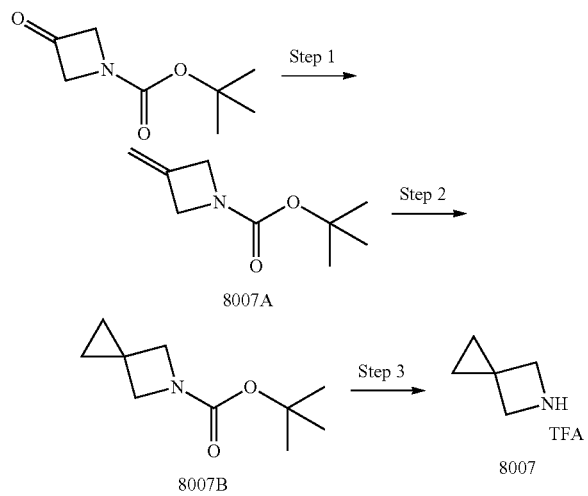

Step 1: A solution of sodium bis(trimethylsilyl)amide in THF (2M; 137 mL, 274 mmol, 2.36 eq) is added over 30 min to methyltriphenylphosphonium bromide (98.0 g, 274 mmol, 2.36 eq) in anhydrous THF (825 mL). The reaction mixture is stirred at RT for 1 h. A solution of tert-butyl 3-oxoazetidine-1-carboxylate (CNH-Tech) (20.0 g, 116 mmol) in anhydrous THF (115 mL) is added over 10 min, and the stirring is continued at RT for 1 h. The solution is diluted with hexanes (1.0 L) and filtered through Celite. The filtrate is concentrated under reduced pressure at 10° C. The crude material is purified by silica gel flash chromatography (20% diethyl ether in hexanes) to afford intermediate 8007A.

Step 2: In a plastic 2 L Erlenmeyer flask, solid 1-methyl-1-nitrosourea (30.9 g, 80 wt. %, 250 mmol) is added over 30 min to a cooled (−10° C.) mixture of diethyl ether (500 mL) and 5 M aqueous potassium hydroxide (250 mL, 1250 mmol). The mixture is stirred at 0° C. for 1 h. The layers are decanted, and the organic layer is transferred to a 1 L Erlenmeyer flask containing potassium hydroxide pellets (125 g, 2.22 mol). The flask containing diazomethane is placed in a cold bath (−10° C.) for 1 h while the next step is being set-up.

The above solution of diazomethane in ether (~500 mL, ~0.5 M, ~250 mmol, 5.0 eq) is transferred at 0° C. over 50 min to a mixture of 8007A (8.50 g, 50.2 mmol) in diethyl ether (300 mL) containing palladium (II) acetate (2.3 g, 10 mmol, 0.20 eq). The reaction mixture is stirred at RT for 16 h, then it is diluted with hexanes (500 mL). The crude mixture is filtered through Celite, and the filtrate is concentrated under reduced pressure at 10° C. The crude material is purified by silica gel flash chromatography (5 to 10% diethyl ether in hexanes) to afford intermediate 8007B.

Step 3: Intermediate 8007 is prepared analogously to the procedure described in example 2B, step 3.

Example 2E

Preparation of Intermediate 8014

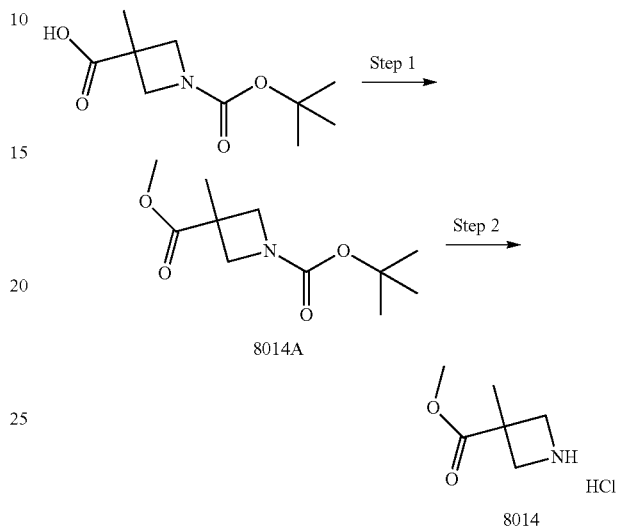

Step 1: A solution of 1-BOC-3-methylazetidine-3-carboxylic acid (ACPharmtech) (185 mg, 0.859 mmol) in DCM (5 mL) at 0° C. is treated with diazomethane etheral solution (as prepared in example 2D, step 2) until gas evolution ceases and the reaction solution remains yellowish. The volatiles are removed under reduced pressure to afford intermediate 8014A.

Step 2: To a solution of crude 8014A (197 mg, 0.859 mmol) in DCM (1 mL) is added a HCl solution in dioxane (4M; 1 mL, 4.0 mmol, 4.65 eq). The mixture is stirred at RT for 5 h, then all volatiles are removed under reduced pressure to afford intermediate 8014 as the HCl salt which is used without further purification.

Example 2F

Preparation of Intermediate 8015

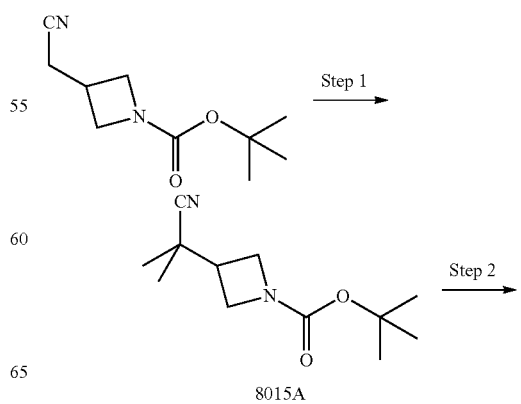

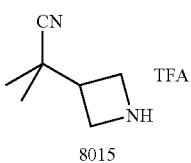

Step 1: To a stirred solution of 1-BOC-3-(cyanomethyl) azetidine (AChemblock) (300 mg, 1.529 mmol) in THF (4 mL) at −78° C. is added a LiHMDS solution in THF (1 M; 3.8 mL, 3.82 mmol, 2.5 eq). The mixture is stirred for 30 min, then methyliodide (0.28 mL, 4.586 mmol, 3.0 eq) is added and the mixture is stirred at RT for 10 h. The reaction mixture is neutralized at 0° C. by adding a saturated aqueous NH$_4$Cl solution (5 mL) and the layer is extracted with EtOAc (3×250 mL). The organic layers are combined and dried by passing through a phase separator cartridge to afford intermediate 8015A.

Step 2: Intermediate 8015 is prepared analogously to the procedure described in example 2B, step 3.

Example 2G

Preparation of Intermediate 8019

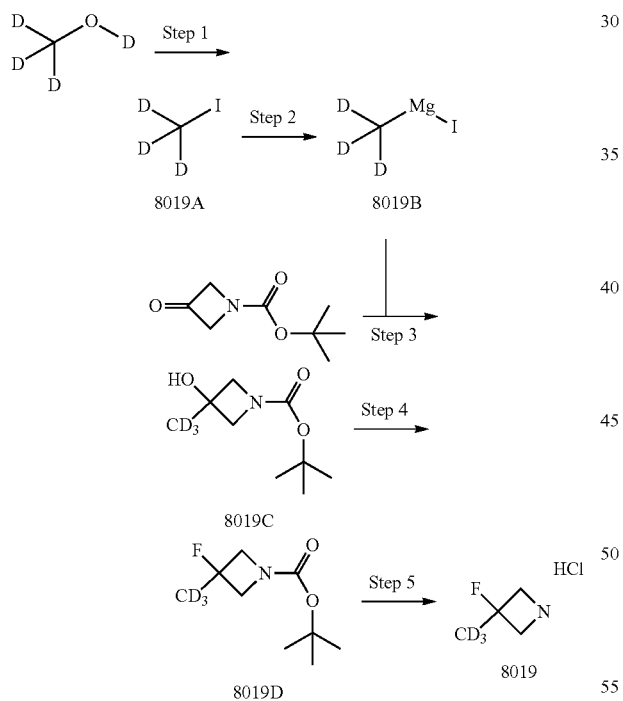

Step 1: Red phosphorus (8.59 g, 277 mmol, 0.4 eq) is placed in a receiving flask to which is attached a bulb-shaped pressure-equalizing dropping funnel fitted with a cold water condenser. Iodine crystals (106 g, 416 mmol, 0.6 eq) are supported in the dropping funnel by a glass wool plug. Methanol-d4 (25.0 g, 693 mmol) is added onto the iodine crystals and this solution is allowed to drip on the red phosphorus below. The receiving flask is immersed in a water bath and warmed to reflux. The refluxing liquid that condenses is returned back onto the iodine crystals and the process continues until all of the iodine is consumed. The resulting mixture is cooled to RT and distilled to afford trideuterated methyl iodide 8019A.

Step 2: To a stirred solution of magnesium turnings (1.99 g, 82.8 mmol, 1.2 eq) in anhydrous diethyl ether (250 mL) is added one iodine crystal and the mixture is stirred for 15 min. Trideuterated methyl iodide 8019A (10.0 g, 69.0 mmol) is added dropwise as an Et$_2$O solution (20 mL) for 1 h. The reaction mixture is stirred for 1.5 h to provide intermediate 8019B which is directly used for the next step.

Step 3: To a stirred solution 3-oxo-azetidine-1-carboxylic acid tert-butyl ester (Aldrich) (5.0 g, 29.2 mmol) in THF (100 mL) at −78° C. is added the freshly prepared Grignard reagent 8019B (assuming 100% from previous reaction: 69.0 mmol, 2.3 eq). The reaction mixture is stirred at −78° C. for 2 h, then a saturated NH$_4$Cl solution (100 mL) is added. The mixture is extracted with EtOAc (3×40 mL). The organic layers are combined, washed with water and brine, dried over Na$_2$SO$_4$, filtered and concentrated. The resulting product is triturated with petroleum ether to afford intermediate 8019C.

Step 4: To a solution of 8019C (2.0 g, 10.7 mmol) in DCM (25 mL) at −78° C. is added DAST (2.58 g, 16.0 mmol, 1.5 eq). After stirring at −78° C. for 1 h, the mixture is stirred overnight at RT. The reaction is neutralized by the addition of a saturated NaHCO$_3$ solution (10 mL) and the mixture is extracted with DCM (3×10 mL). The organic layers are combined, washed with brine, dried over Na$_2$SO$_4$, filtered and concentrated. The residue is purified by flash chromatography on silica gel to afford intermediate 8019D.

Step 5: Compound 8019 is prepared according to the procedure described in example 2E, step 2.

The following amines, their corresponding salt or the analogous N-BOC protected amines are prepared according to the procedures described in the literature, herein incorporated by reference:

8001 (*J. Org. Chem.* 2006, 71, 7100), 8002 and 8016 (*J. Med. Chem.* 2008, 51, 7380), 8018 (*Org. Lett.* 2010, 12 (9), 1944-1947).

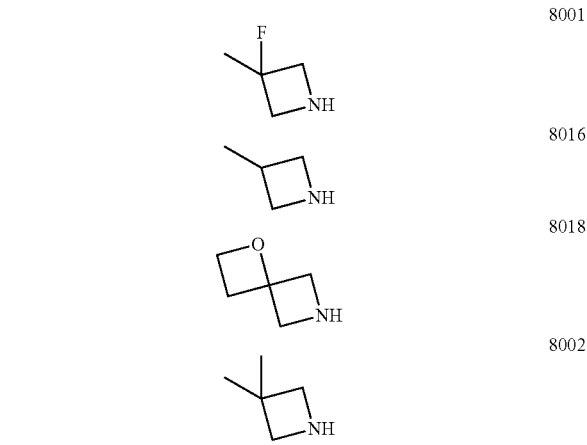

The following amines, their corresponding salt or the analogous N-BOC protected amines are commercially available:

8003 (Matrix), 8008 (Parkway), 8009 (Paradigm), 8010 (Chembridge-BB), 8011 (Alfa), 8012 (Amatek), 8013, (Enamine), 8017 (Aldrich).

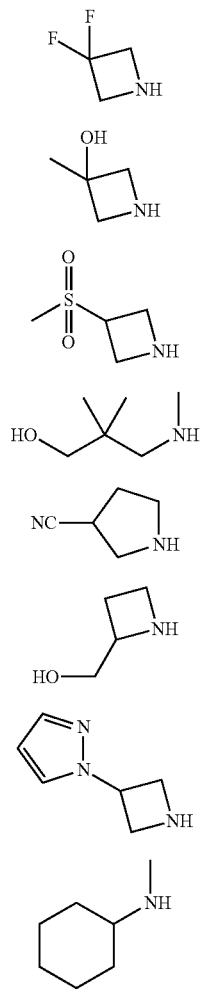

Example 3A

Preparation of Intermediate 3A

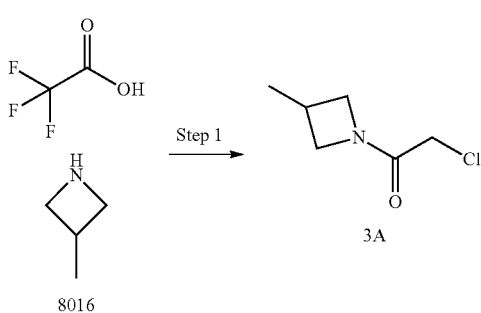

Step 1: To a solution of the TFA salt of 8016 (8.42 g, 45.5 mmol) in DCM (20 mL) is added a saturated aqueous solution of NaHCO₃ (100 mL) and the mixture is stirred for 15 min. To this mixture is added neat chloroacetyl chloride (3.6 mL, 45.5 mmol) over a 15 min period, and the mixture is stirred for 45 min. The layers are separated and the aqueous layer is extracted with DCM (3×10 mL). The combined organic layers are dried by passing through a phase separator cartridge and concentrated under vacuum to afford intermediate 3A which is used without further purification.

Example 3B

Preparation of Intermediate 3B

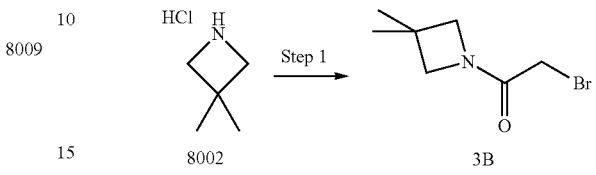

Step 1: A solution of the hydrochloride salt of 8002 (1.00 g, 11.7 mmol) is dissolved in DCM (40 mL) and NaOH (1.00 M aqueous solution) (11.7 mL, 11.7 mmol, 1.00 eq) is added. The solution is filtered on a phase separator. Bromoacetyl bromide (1.02 mL, 11.7 mmol, 1.00 eq) is added followed by Et₃N (2.46 mL, 17.6 mmol, 1.50 eq) and the solution is stirred at −10° C. for 2 h. The solution is diluted with DCM and washed with water (3×). The organic layer is dried over MgSO₄, filtered and concentrated under reduced pressure to provide intermediate 3B.

Example 3C

Preparation of Intermediate 3C

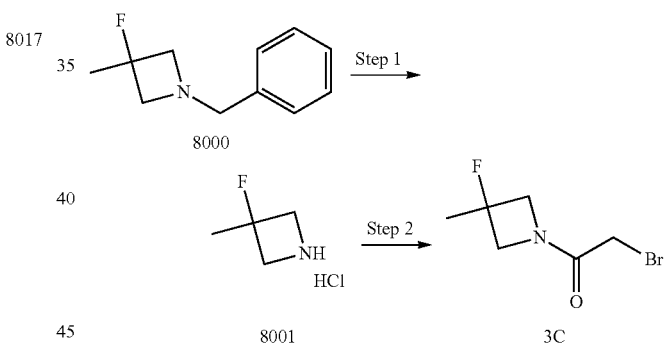

Step 1: 1-benzyl-3-fluoro-3-methylazetidine 8000 (prepared analogously to the procedure in *J. Org. Chem.* 2006, 71, 7100, herein incorporated by reference) (56.0 g, 313 mmol) is charged in a round-bottom flask and dissolved in EtOH (1.00 L). 4.0 M HCl solution in dioxane (79.0 mL, 316 mmol, 1.0 eq) is added, followed by palladium hydroxide on carbon (28 g). The mixture is hydrogenated at 2 atm for 36 h at RT. The mixture is filtered through Celite and rinsed with EtOH. The filtrate is concentrated under reduced pressure and the residue is triturated in diethyl ether. The residue is purified by flash chromatography (5% to 10% MeOH in DCM) to provide intermediate 8001 as a hydrochloride salt.

Step 2: The hydrochloride salt of intermediate 8001 (5.22 g, 41.6 mmol) is dissolved in DCM (75 mL) and NaOH (1.0 M aqueous solution; 41.6 mL, 41.6 mmol, 1.0 eq) is added. The solution is filtered though a phase separator cartridge. Bromoacetyl bromide (3.62 mL, 41.6 mmol, 1.0 eq) is added followed by Et₃N (8.69 mL, 62.4 mmol, 1.5 eq) and the solution is stirred at −10° C. for 2 h. The solution is diluted with DCM and washed with water (3×30 mL). The organic layer is dried over MgSO₄, filtered and concentrated under reduced pressure to provide intermediate 3C.

Example 4

Preparation of Compounds 5007 and 5026

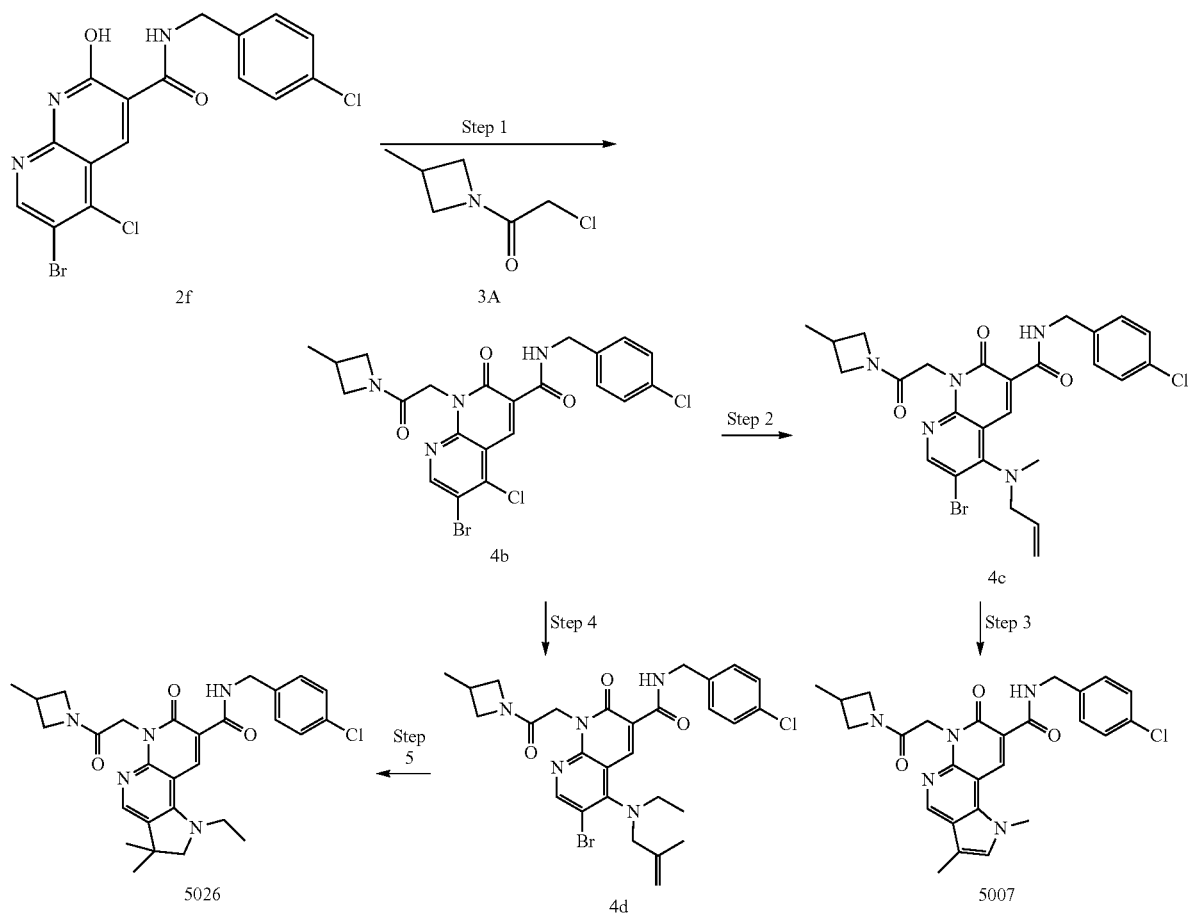

Step 1: To a solution of 2f (10.8 g, 25.3 mmol) in DMF (175 mL) is added solid potassium carbonate (8.95 g, 64.8 mmol, 2.6 eq). In another flask, a solution of 3A (4.11 g, 27.8 mmol, 1.1 eq) in DMF (25 mL) is prepared, and then transferred to the previous mixture. The reaction mixture is stirred at 50° C. for 3 h. Water is added and the mixture is extracted with DCM (3×40 mL). The organic layers are combined, washed with brine, dried by passing through a phase separator cartridge and concentrated under reduced pressure. The crude mixture is purified by Combiflash (220 g silica gel column; eluents: hexane/EtOAc (gradient 40% to 100%)). The pure fractions are combined, concentrated, and dried in vacuo to afford intermediate 4b.

Step 2: To a solution of 4b (200 mg, 0.372 mmol) and N-methyl allylamine (32 mg, 0.446 mmol, 1.2 eq) in DMF (4 mL) is added solid potassium carbonate (77 mg, 0.557 mmol, 1.5 eq). The mixture is warmed at 50° C. for 2 h, then EtOAc (10 mL) is added. The mixture is washed with water (3×5 mL) and brine (1×). The organic layers are dried by passing through a phase separator cartridge, and concentrated under reduced pressure. The crude residue is purified by Combiflash (4 g silica gel column; eluents: hexanes/EtOAc (gradient 40% to 100%)). The pure fractions are combined, concentrated, and dried in vacuo to afford intermediate 4c.

Step 3: In a high pressure flask, Et$_3$N (58 µL, 0.408 mmol, 2 eq), triphenylphosphine (16 mg, 0.061 mmol, 0.3 eq) and palladium acetate (4.6 mg, 0.020 mmol, 0.1 eq) are successively added to a solution containing 4c (117 mg, 0.204 mmol) in MeCN (5 mL). The mixture is sealed and warmed at 70° C. for 3 h, and then the solvent is removed under reduced pressure. The crude mixture is diluted in MeOH, filtered through Millex and purified by reverse phase semipreparative HPLC (MeCN/water, 0.06% TFA buffer). The pure fractions are combined and lyophilized to give compound 5007.

Step 4: Intermediate 4d is prepared analogously to the procedure described previously in step 2 using N-ethyl-2-methylallylamine.

Step 5: In a high pressure flask, Et$_3$N (21 µL, 0.146 mmol, 2 eq), triphenylphosphine (4.8 mg, 0.007 mmol, 0.1 eq), sodium formate (5.0 mg, 0.073 mmol, 1 eq) and palladium acetate (1.6 mg, 0.020 mmol, 0.1 eq) are successively added to a solution containing 4d (44 mg, 0.073 mmol) in DMF (5 mL). The mixture is sealed and warmed at 90° C. for 3 h, and then the solvent is removed under reduced pressure. The crude mixture is diluted in MeOH, filtered through Millex and purified by reverse phase semipreparative HPLC (MeOH/ammonium bicarbonate buffer pH 10). The pure fractions are combined and lyophilized to give compound 5026.

Example 5

Preparation of Compound 5021

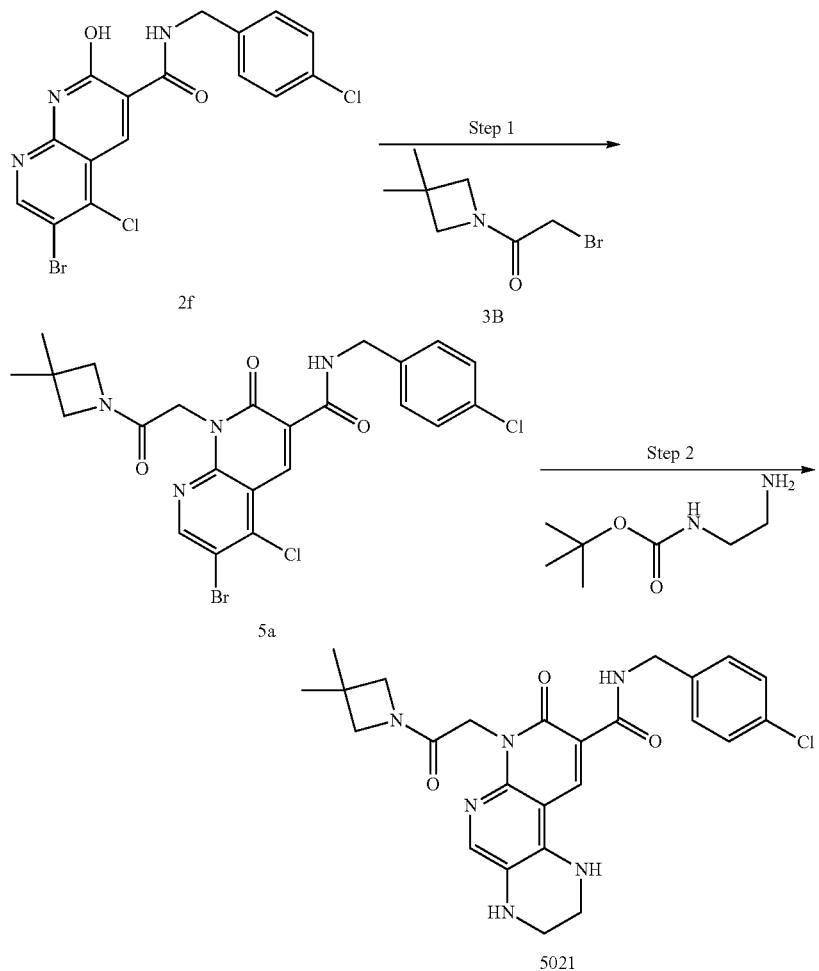

Step 1: Intermediate 5a is prepared analogously to the procedure described in example 4, step 1 using 2f (2.50 g, 5.85 mmol) and 3B (1.95 g, 9.46 mmol, 1.6 eq).

Step 2: In a microwave tube, a mixture of 5a (60 mg, 0.109 mmol), tert-butyl-N-(2-aminoethyl)carbamate (28 mg, 0.174 mmol, 1.6 eq), RuPhos ligand (10 mg, 0.021 mmol, 0.2 eq), palladium acetate (2.4 mg, 0.011 mmol, 0.1 eq) and cesium carbonate (71 mg, 0.217 mmol, 2.0 eq) in anhydrous toluene (1 mL) is prepared. This mixture is degassed with an argon stream while sonicating for 5 min, then the tube is capped and warmed at 130° C. for 14 h. EtOAc (5 mL) is added. The mixture is filtered using Millex, and then the solvent concentrated. The residue is dissolved in DCM (2 mL). TFA (0.3 mL) is added and the mixture is stirred for 1 h. The solvent is concentrated and DMF (1 mL) is added. The mixture is filtered on Acrodisc and purified by reverse phase semipreparative HPLC (MeCN/water, ammonium bicarbonate buffer, pH 10). The pure fractions are combined and lyophilized to give compound 5021.

Example 6

Preparation of Compound 5012

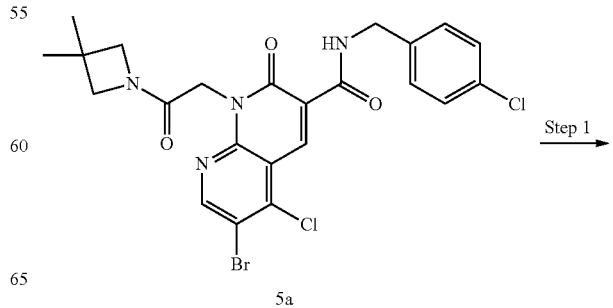

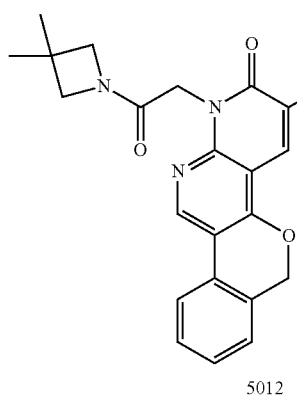

5012

Step 1: In a microwave tube, a mixture of 5a (65 mg, 0.118 mmol), 2-(hydroxymethyl)phenyl boronic acid (29 mg, 0.188 mmol, 1.6 eq), cesium fluoride (27 mg, 0.177 mmol, 1.5 eq), trans-dichloro-bis(triphenylphosphine) palladium (16 mg, 0.024 mmol, 0.2 eq) and cesium carbonate (77 mg, 0.235 mmol, 2.0 eq) in anhydrous toluene (1 mL) is prepared. This mixture is degassed with an argon stream while sonicating for 5 min, then the tube is capped and warmed at 120° C. for 2 h. The solvent is concentrated and DMF (1 mL) is added. The mixture is filtered on Acrodisc and purified by reverse phase semipreparative HPLC (MeCN/water, ammonium formate buffer, pH 3.8). The pure fractions are combined and lyophilized to give compound 5012.

Example 7

Preparation of Compounds 5010 and 5033

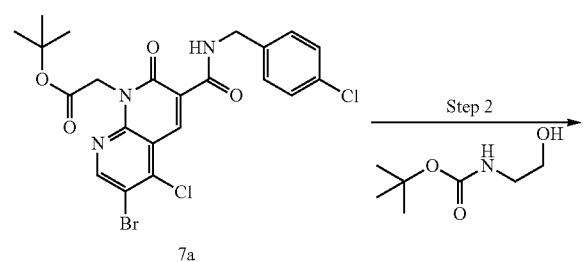

2f

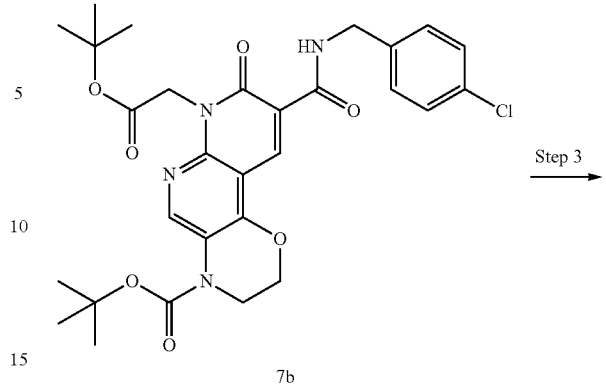

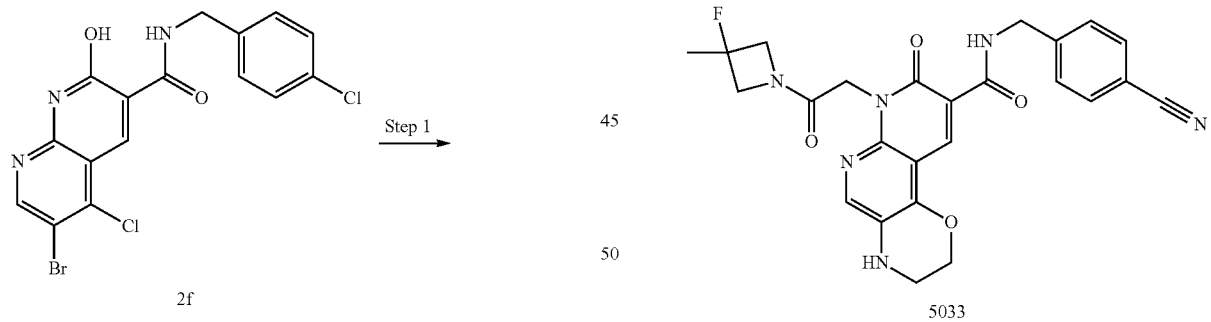

Step 1: To a solution of 2f (3.0 g, 7.02 mmol) and tert-butyl bromoacetate (1.3 mL, 8.78 mmol, 1.25 eq) in DMF (30 mL) is added solid potassium carbonate (2.91 g, 21.1 mmol, 3.0 eq). The mixture is stirred at RT for 3.5 h. Water is added and the mixture is extracted with EtOAc (3×15 mL). The combined organic layers are washed with brine (1×), dried over MgSO$_4$, filtered and concentrated. The solid is triturated with MTBE and dried under high vacuum to afford intermediate 7a which is used without further purification.

Step 2: In a microwave tube, a mixture of 7a (1.0 g, 1.85 mmol), tert-butyl N-(2-hydroxyethyl)carbamate (476 mg, 2.96 mmol, 1.6 eq), RuPhos ligand (172 mg, 0.369 mmol, 0.2 eq), palladium acetate (41 mg, 184 mmol, 0.1 eq) and cesium carbonate (1.20 g, 3.70 mmol, 2.0 eq) in anhydrous 1,4- dioxane (15 mL) is prepared. This mixture is degassed with an argon stream while sonicating for 5 min, then the tube is capped and submitted to microwave conditions for 20 min at 120° C. (2×). EtOAc (100 mL) is added and the mixture is washed with water and brine. The organic layers are dried by passing through a phase separator cartridge and concentrated. The crude residue is purified by Combiflash (20 g silica gel column; eluents: hexanes/EtOAc (gradient 40% to 100%)). The pure fractions are combined and concentrated, then dried in vacuo to afford intermediate 7b.

Step 3: A solution of 7b (398 mg, 0.60 mmol) in DCM (8 mL) is treated with TFA (8 mL) and the mixture is stirred at RT for 1 h. All volatiles are removed under reduced pressure to afford intermediate 7c which is used without further purification.

Step 4: To a solution of 7c (290 mg, 0.60 mmol), the hydrochloride salt of intermediate 8001 (110 mg, 0.88 mmol, 1.3 eq) and diisopropylethylamine (0.35 mL, 2.03 mmol, 3.0 eq) in DMF (5 mL) is added HATU (334 mg, 0.88 mmol, 1.3 eq). The mixture is stirred at RT for 15 h. EtOAc (10 mL) is added and the mixture is washed with 1N NaOH solution (2×5 mL), 1N HCl solution (2×5 mL) and brine. The organic layers are dried by passing through a phase separator cartridge and concentrated. The crude residue is triturated with MTBE and filtered to afford compound 5010.

Step 5: In a microwave tube, a solution of compound 5010 (70 mg, 0.140 mmol), zinc cyanide (33 mg, 0.28 mmol, 2.0 eq) and bis(tri-tert-butylphosphine) palladium (14 mg, 0.028 mmol, 0.2 eq) in DMAc (1.5 mL) is prepared. The tube is capped and heated to 140° C. for 5 h. The reaction mixture is filtered on Acrodisc and purified by reverse phase semi-preparative HPLC (MeCN/water, ammonium bicarbonate buffer, pH 10). The pure fractions are combined and lyophilized to give compound 5033.

Step 1: In a microwave tube, a mixture of 5a (60 mg, 0.109 mmol), N-BOC-2-amino-2-methyl-1-propanol (33 mg, 0.174 mmol, 1.6 eq), RuPhos ligand (10 mg, 0.021 mmol, 0.2 eq), palladium acetate (2.4 mg, 0.011 mmol, 0.1 eq) and cesium carbonate (71 mg, 0.217 mmol, 2.0 eq) in anhydrous toluene (1 mL) is prepared. This mixture is degassed with an argon stream while sonicating for 5 min, then the tube is capped and warmed at 120° C. for 14 h. EtOAc (5 mL) is added. The mixture is filtered using Millex and the solvent is concentrated. The residue is dissolved in DCM (1 mL). TFA (0.5 mL) is added and the mixture is stirred for 1 h. The solvent is concentrated and DMF (1 mL) is added. The mixture is filtered on Acrodisc and purified by reverse phase semipreparative HPLC (MeCN/water, ammonium bicarbonate buffer, pH 10). The pure fractions are combined and lyophilized to give compound 5022.

Example 9

Preparation of Compound 5015

Example 8

Preparation of Compound 5022

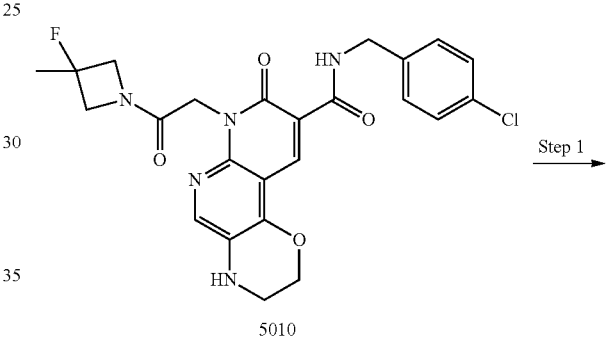

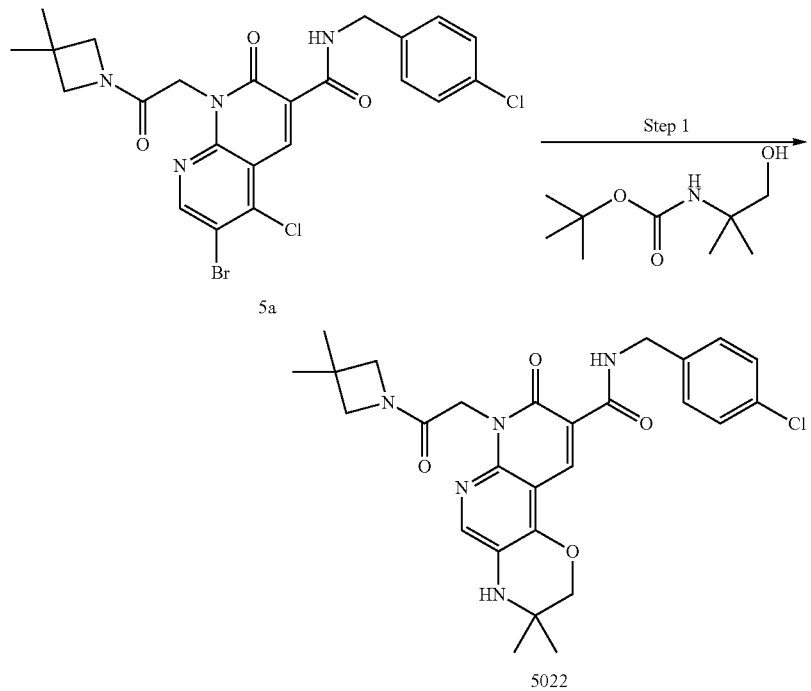

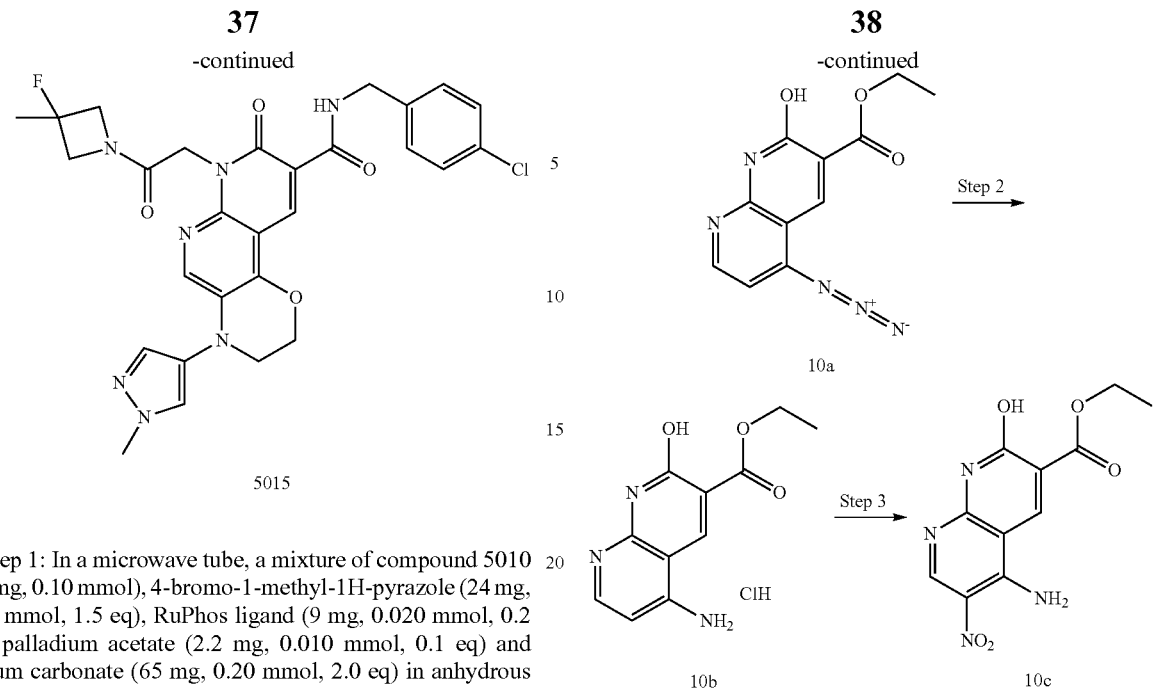

5015

Step 1: In a microwave tube, a mixture of compound 5010 (50 mg, 0.10 mmol), 4-bromo-1-methyl-1H-pyrazole (24 mg, 0.15 mmol, 1.5 eq), RuPhos ligand (9 mg, 0.020 mmol, 0.2 eq), palladium acetate (2.2 mg, 0.010 mmol, 0.1 eq) and cesium carbonate (65 mg, 0.20 mmol, 2.0 eq) in anhydrous toluene (1 mL) is prepared. This mixture is degassed with an argon stream while sonicating for 5 min, then the tube is capped and warmed at 135° C. for 14 h. The solvent is concentrated and DMF (1 mL) is added. The mixture is filtered on Acrodisc and purified by reverse phase semipreparative HPLC (MeCN/water, ammonium bicarbonate buffer, pH 10). The pure fractions are combined and lyophilized to give compound 5015.

Example 10

Preparation of Intermediate 10c

Step 1: To a suspension of 1d (6.0 g, 23.7 mmol) in NMP (200 mL) is added sodium azide (1.85 g, 28.5 mmol, 1.2 eq). This slurry is stirred overnight at RT. Cold water (100 mL) is added. The resulting precipitate is filtered, rinsed with water and dried in vacuo to afford intermediate 10a.

Step 2: In a round bottom flask equipped with a 3-way valve, a mixture of 10a (3.11 g, 12.0 mmol) in EtOH (25 mL) is prepared. This mixture is degassed with argon, then 5% palladium on charcoal (50 mg) is added. The system is purged with hydrogen using a vacuum/back filling technique. This mixture is stirred for 18 h under a hydrogen atmosphere. When the reaction is complete, the system is purged with argon (vacuum/back filling). The mixture is filtered over celite and rinsed with 6N HCl. The filtrate is concentrated to dryness to afford the hydrochloride salt 10b.

Step 3: To a solution of 10b (2.60 g, 9.64 mmol) in concentrated sulfuric acid (25 mL) is added fuming nitric acid (1.5 mL) and the mixture is stirred overnight. The reaction mixture is poured into cold water (0° C.) and stirred for 2 h. The resulting precipitate is collected by filtration and dried in vacuo to afford intermediate 10c. The pH of the filtrate is adjusted to 7 with NaOH 10N (careful: very exothermic). This mixture is stirred for 1 h at 0° C., and then filtered (Buchner) to isolate additional intermediate 10c. Both crops are combined together and intermediate 10c is used without further purification.

Example 11

Preparation of Intermediates 11c and 11h

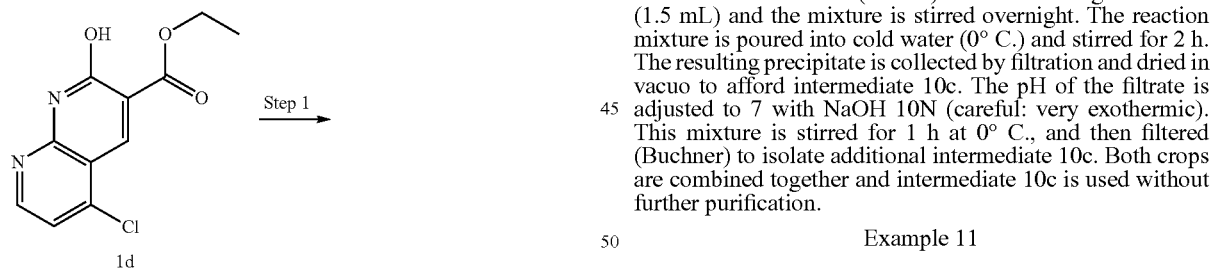

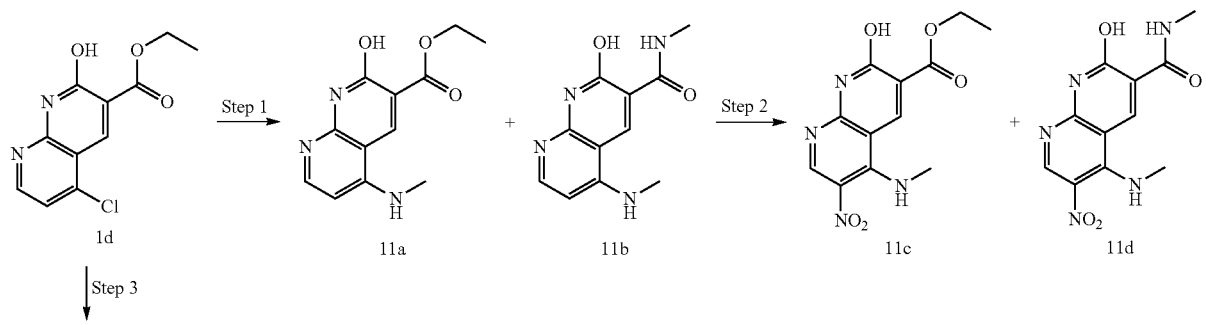

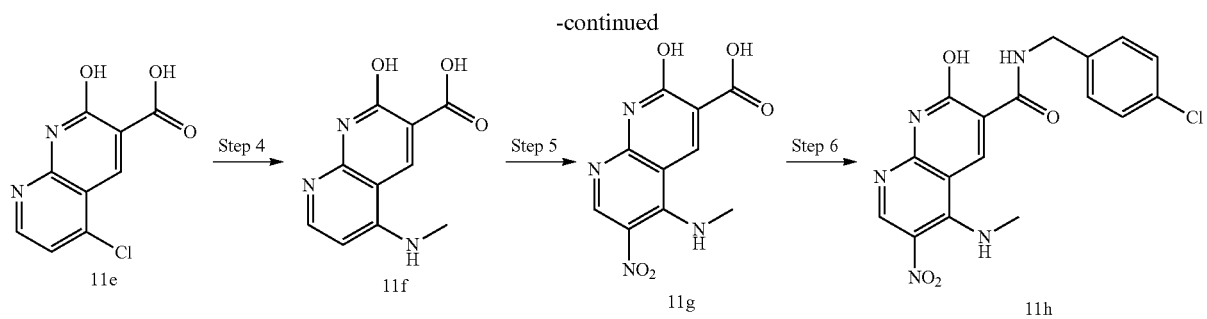

Step 1: In a high pressure reaction flask, a suspension of 1d (15 g, 23.7 mmol) and a methylamine solution (2M in THF, 30 mL, 60 mmol, 2.5 eq) in NMP (350 mL) is prepared and the mixture is stirred. The resulting mixture is heated to 50° C. for 60 min. Additional methylamine is added until the starting material is completely consumed. The reaction mixture is cooled to 0° C. and water is added. The solid is collected by Buchner filtration, rinsed with water and dried to afford a mixture of intermediates 11a and 11b. This mixture is used directly in the next step without further purification.

Step 2: To a solution of 11a (containing 11b) (13.8 g, 55.9 mmol) in concentrated sulfuric acid (50 mL) is added fuming nitric acid (3.5 mL, 83.8 mmol) [caution: exothermic reaction]. After stirring overnight at RT, the mixture is poured into cold water (0° C.) and stirred for 2 h. The resulting solid is collected by Buchner filtration, rinsed, and dried to provide compound 11c (contaminated with 11d as indicated by HPLC analysis).

Step 3: To a solution of 1d (10.0 g, 39.58 mmol) in a mixture of THF (100 mL)/MeOH (50 mL)/water (50 mL) is added solid lithium hydroxide monohydrate (4.82 g, 118.7 mmol, 3.0 eq) and the reaction mixture is warmed at 60° C. for 2 h. The mixture is cooled to RT, and then water (500 mL) and acetic acid are added until the mixture reaches ~pH 3. The resulting residue is collected by Buchner filtration and dried in vacuo to afford intermediate 11e.

Step 4: In a high pressure reaction flask, a suspension of 11e (8.71 g, 38.78 mmol) and methylamine solution (33% in EtOH, 48.3 mL, 388 mmol, 10 eq) in EtOH (200 mL) is prepared and the resulting mixture is heated to 125° C. for 24 h with stirring. The mixture is cooled to RT and concentrated to approximately 100 mL. Water is added (500 mL) and the resulting residue is collected by Buchner filtration and dried in vacuo to give intermediate 11 f.

Step 5: To a solution of 11f (4.115 g, 18.77 mmol) in concentrated sulfuric acid (22 mL) is added fuming nitric acid (1.6 mL, 37.5 mmol, 2.0 eq) [caution: exothermic reaction]. After stirring for 16 h at RT, the mixture is poured into cold water (0° C.). The resulting residue is collected by Buchner filtration, rinsed with water, and dried under high vacuum to provide intermediate 11g.

Step 6: To a solution of 11g (2.092 g, 7.92 mmol) in DMF (80 mL) is added diisopropylethylamine (4.14 mL, 23.76 mmol, 3.0 eq) followed by HATU (3.61 g, 9.50 mmol, 1.2 eq). The mixture is stirred for 10 min before adding 4-chlorobenzyl amine (1.17 mL, 9.54 mmol, 1.2 eq). This mixture is stirred for 30 min at RT, and then poured into cold water. The resulting residue is collected by Buchner filtration, rinsed with water and dried in vacuo to afford intermediate 11h.

Example 12

Preparation of Compound 5037

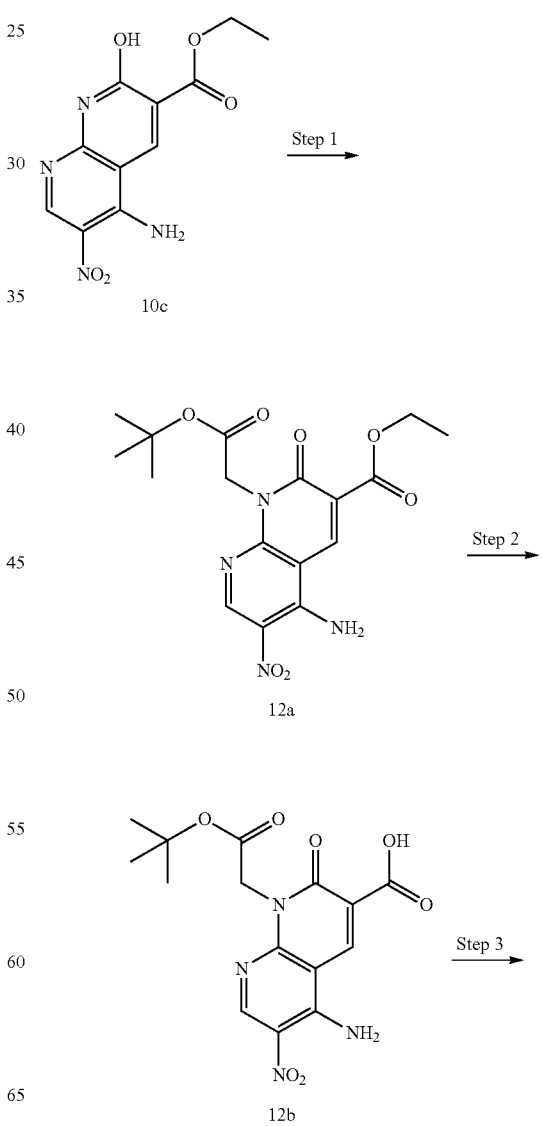

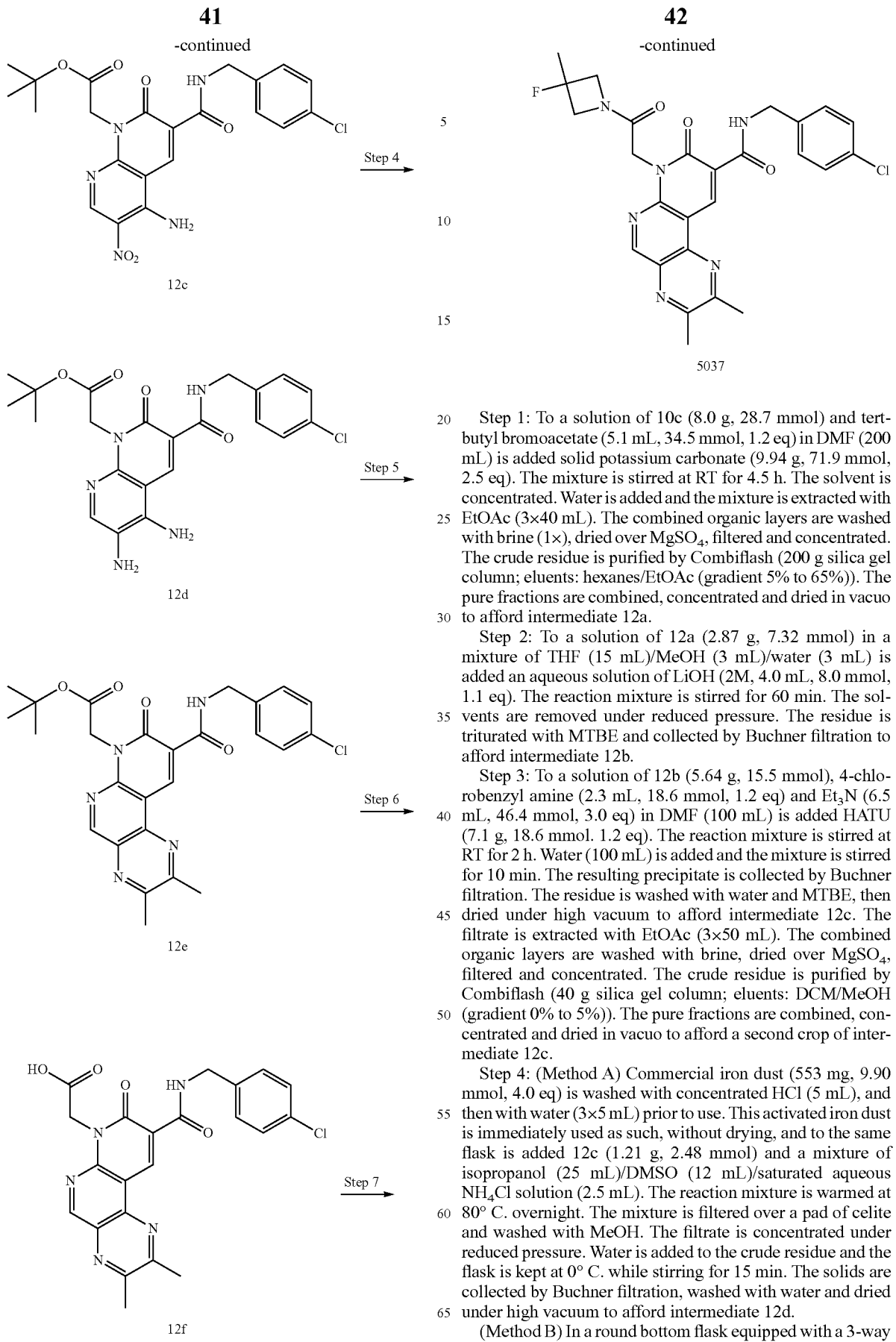

Step 1: To a solution of 10c (8.0 g, 28.7 mmol) and tert-butyl bromoacetate (5.1 mL, 34.5 mmol, 1.2 eq) in DMF (200 mL) is added solid potassium carbonate (9.94 g, 71.9 mmol, 2.5 eq). The mixture is stirred at RT for 4.5 h. The solvent is concentrated. Water is added and the mixture is extracted with EtOAc (3×40 mL). The combined organic layers are washed with brine (1×), dried over MgSO₄, filtered and concentrated. The crude residue is purified by Combiflash (200 g silica gel column; eluents: hexanes/EtOAc (gradient 5% to 65%)). The pure fractions are combined, concentrated and dried in vacuo to afford intermediate 12a.

Step 2: To a solution of 12a (2.87 g, 7.32 mmol) in a mixture of THF (15 mL)/MeOH (3 mL)/water (3 mL) is added an aqueous solution of LiOH (2M, 4.0 mL, 8.0 mmol, 1.1 eq). The reaction mixture is stirred for 60 min. The solvents are removed under reduced pressure. The residue is triturated with MTBE and collected by Buchner filtration to afford intermediate 12b.

Step 3: To a solution of 12b (5.64 g, 15.5 mmol), 4-chlorobenzyl amine (2.3 mL, 18.6 mmol, 1.2 eq) and Et₃N (6.5 mL, 46.4 mmol, 3.0 eq) in DMF (100 mL) is added HATU (7.1 g, 18.6 mmol, 1.2 eq). The reaction mixture is stirred at RT for 2 h. Water (100 mL) is added and the mixture is stirred for 10 min. The resulting precipitate is collected by Buchner filtration. The residue is washed with water and MTBE, then dried under high vacuum to afford intermediate 12c. The filtrate is extracted with EtOAc (3×50 mL). The combined organic layers are washed with brine, dried over MgSO₄, filtered and concentrated. The crude residue is purified by Combiflash (40 g silica gel column; eluents: DCM/MeOH (gradient 0% to 5%)). The pure fractions are combined, concentrated and dried in vacuo to afford a second crop of intermediate 12c.

Step 4: (Method A) Commercial iron dust (553 mg, 9.90 mmol, 4.0 eq) is washed with concentrated HCl (5 mL), and then with water (3×5 mL) prior to use. This activated iron dust is immediately used as such, without drying, and to the same flask is added 12c (1.21 g, 2.48 mmol) and a mixture of isopropanol (25 mL)/DMSO (12 mL)/saturated aqueous NH₄Cl solution (2.5 mL). The reaction mixture is warmed at 80° C. overnight. The mixture is filtered over a pad of celite and washed with MeOH. The filtrate is concentrated under reduced pressure. Water is added to the crude residue and the flask is kept at 0° C. while stirring for 15 min. The solids are collected by Buchner filtration, washed with water and dried under high vacuum to afford intermediate 12d.

(Method B) In a round bottom flask equipped with a 3-way valve, a suspension of 12c (550 mg, 1.13 mmol) in a mixture of MeOH/EtOAc (5 mL:2 mL) is prepared. This mixture is degassed with argon, and then 5% palladium on charcoal (20 mg) is added. The system is purged with hydrogen using a vacuum/back filling technique. This mixture is stirred for 20 h under a hydrogen atmosphere. When the reaction is complete, the system is purged with argon (vacuum/back filling). The mixture is filtered over celite and rinsed thoroughly with MeOH. The filtrate is concentrated to dryness to afford intermediate 12d which is used directly in the next step without further purification.

Step 5: Intermediate 12d (90 mg, 0.197 mmol) and 2,3-butadione (26 μL, 0.295 mmol, 1.5 eq) are dissolved in DMF (3 mL) and the reaction is warmed at 100° C. for 60 min. The reaction is cooled to RT and water is added. The mixture is extracted with EtOAc (3×3 mL). The combined organic layers are washed with brine, dried by passing through a phase separator cartridge and concentrated. The crude residue is purified by Combiflash (4 g silica gel column; eluents: hexanes/EtOAc (gradient 20% to 100%)). The pure fractions are combined and concentrated to afford intermediate 12e.

Step 6: A solution of 12e (41 mg, 0.081 mmol) in DCM (1 mL) is treated with TFA (0.1 mL) and the mixture is stirred at RT overnight. All volatiles are removed under reduced pressure to afford intermediate 12f which is used without further purification.

Step 7: Compound 5037 is prepared analogously to the procedure described in example 7, step 4. Using 12f (36 mg, 0.80 mmol) and the hydrochloride salt of intermediate 8001 (13 mg, 0.104 mmol, 1.3 eq), compound 5037 is isolated after purification by reverse phase semipreparative HPLC (MeOH/water, ammonium formate buffer, pH 3.8).

Example 13

Preparation of Compounds 2010 and 2001

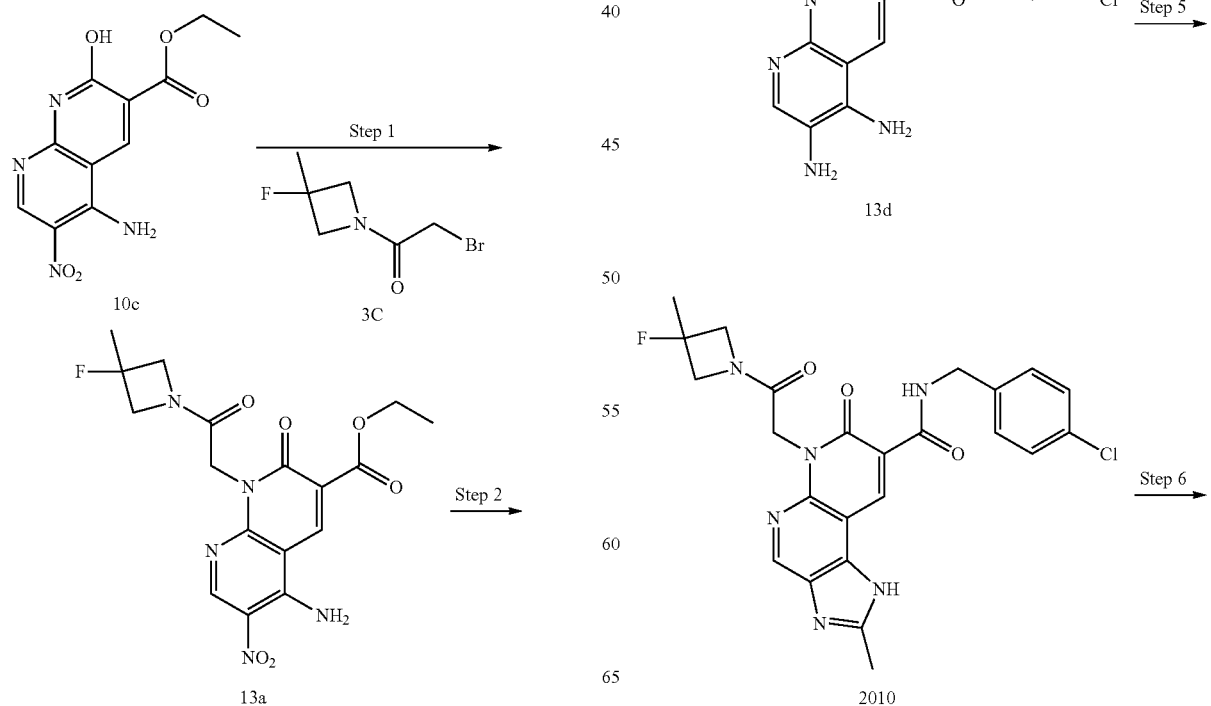

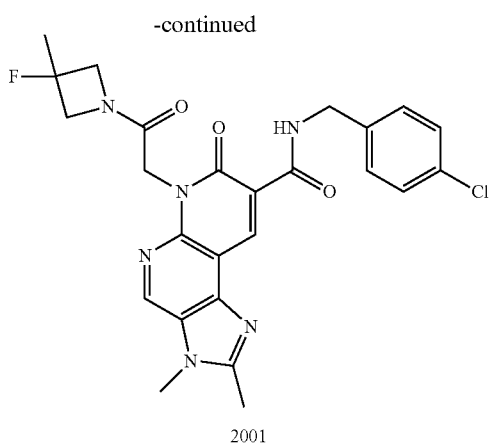

2001

Step 1: Intermediate 13a is prepared analogously to the procedure described in example 4, step 1 using 10c (1.20 g, 4.31 mmol) and 3C (1.09 g, 5.18 mmol, 1.2 eq).

Step 2: Intermediate 13b is prepared analogously to the procedure described in example 12, step 2.

Step 3: Intermediate 13c is prepared analogously to the procedure described in example 12, step 3.

Step 4: Intermediate 13d is prepared analogously to the procedure described in example 12, step 4 (Method A).

Step 5: In a flask containing trimethyl orthoacetate (2.29 g, 19.0 mmol, 100 eq) is added TFA (4 mg, 0.038 mmol, 0.2 eq). This mixture is stirred for 5 min, then transferred to a solution of 13d (90 mg, 0.190 mmol) in trimethyl orthoacetate (0.5 mL). The reaction mixture is stirred at RT for 2 h. All volatiles are removed under reduced pressure. Approximately half of the crude residue is purified by reverse phase semipreparative HPLC (MeOH/water, ammonium formate pH 3.8). The pure fractions are combined and lyophilized to give compound 2010. The remaining crude residue is used directly in the next step.

Step 6: To a solution of crude compound 2010 (29 mg, 0.058 mmol) in DMF (1 mL) containing potassium carbonate (24 mg, 0.175 mmol, 3 eq) is added iodomethane (4.3 µL, 0.070 mmol, 1.2 eq). After being stirred for 1 h at RT, the mixture is filtered on Acrodisc and purified by reverse phase semipreparative HPLC (MeOH/water, ammonium formate pH 3.8). The pure fractions are combined and lyophilized to give compound 2001.

Example 14

Preparation of Compounds 2002 and 2003

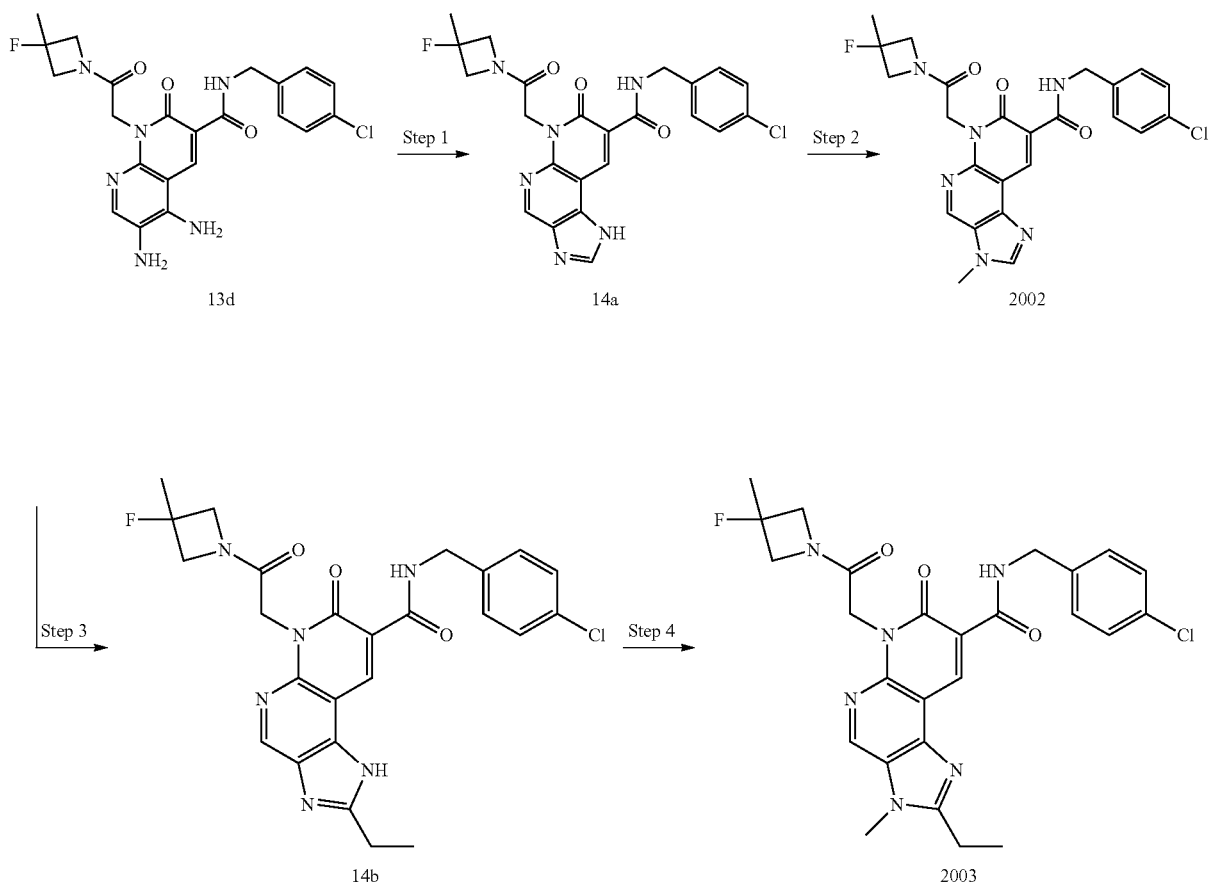

Step 1: In a flask containing trimethyl orthoformate (2.02 g, 19.0 mmol, 100 eq) is added TFA (4 mg, 0.038 mmol, 0.2 eq). This mixture is stirred for 5 min, then transferred to a solution of 13d (90 mg, 0.190 mmol) in trimethyl orthoformate (0.5 mL). The reaction mixture is stirred at RT for 2 h. All volatiles are removed under reduced pressure and the crude intermediate 14a is directly used in the next step.

Step 2: To a solution of 14a (45 mg, 0.093 mmol) in DMF (0.7 mL) containing potassium carbonate (39 mg, 0.280 mmol, 3 eq) is added iodomethane (7 µL, 0.112 mmol, 1.2 eq). Additional iodomethane is added to complete the conversion. After being stirred for 20 h at RT, the mixture is filtered on Acrodisc and purified by reverse phase semi-preparative HPLC (MeOH/water, ammonium formate pH 3.8). The pure fractions are combined and lyophilized to give compound 2002.

Step 3: In a flask containing triethyl orthopropionate (0.13 mL, 0.656 mmol, 5.0 eq) is added TFA (3 mg, 0.026 mmol, 0.2 eq). This mixture is stirred for 5 min, then transferred to a solution of 13d (62 mg, 0.131 mmol) in DCM (1 mL). The reaction mixture is stirred at RT for 20 h. All volatiles are removed under reduced pressure to afford crude intermediate 14b, which is directly used in the next step.

Step 4: To a solution of 14b (67 mg, 0.131 mmol) in DMF (1.0 mL) containing potassium carbonate (54 mg, 0.393 mmol, 3 eq) is added iodomethane (10 µL, 0.157 mmol, 1.2 eq). After being stirred for 2 h at RT, the mixture is filtered on Acrodisc and purified by reverse phase semipreparative HPLC (MeOH/water, ammonium formate pH 3.8). The pure fractions are combined and lyophilized to give compound 2003.

Example 15

Preparation of Compound 2021

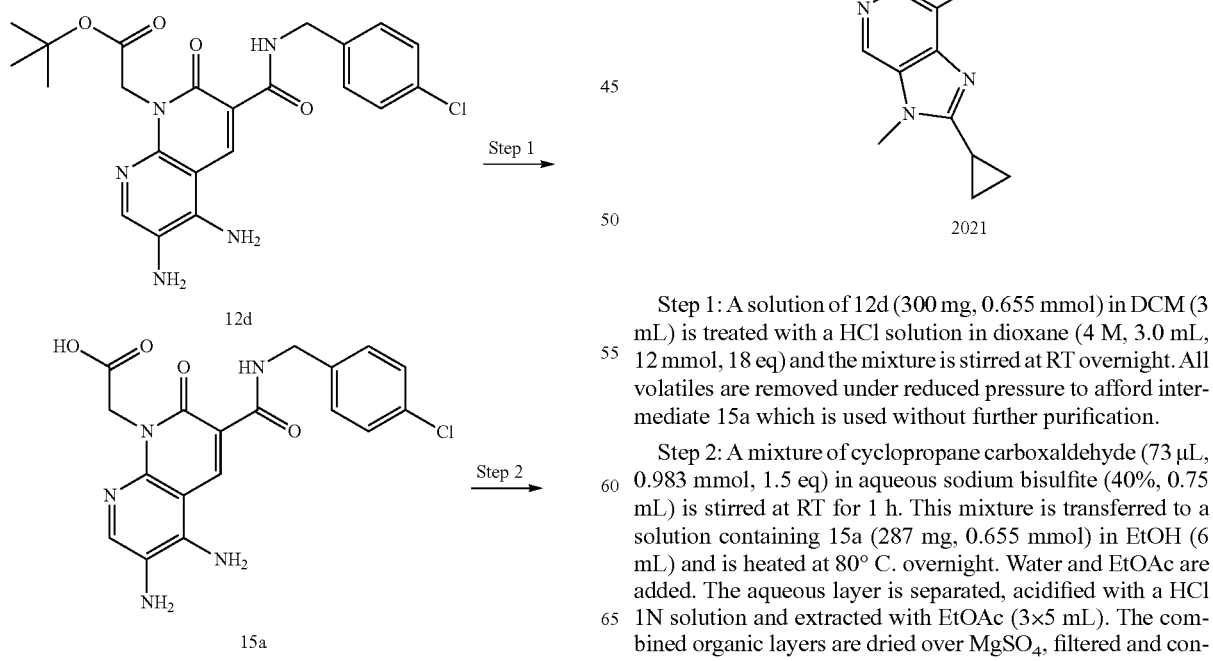

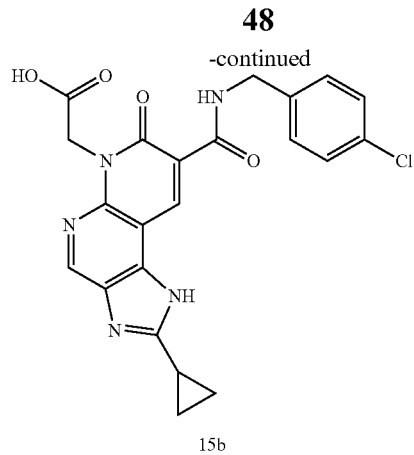

15b

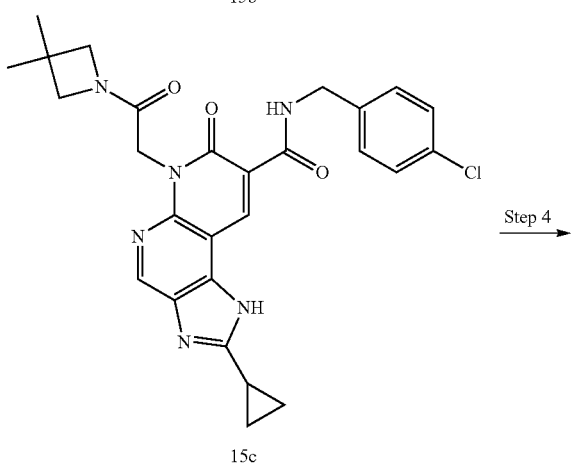

15c

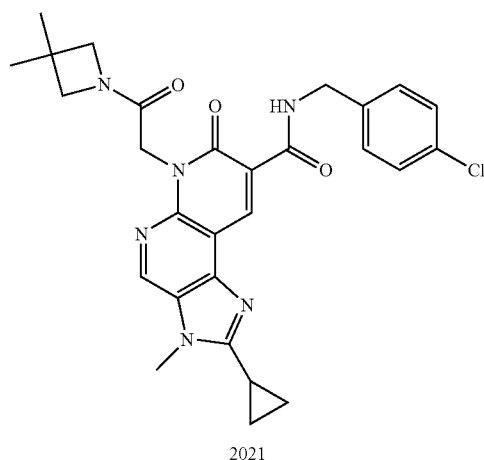 [SMILES: Cn1c(C2CC2)nc2c3cc(C(=O)NCc4ccc(Cl)cc4)c(=O)n(CC(=O)N4CC(C)(C)C4)c3ncc21]

2021

Step 1: A solution of 12d (300 mg, 0.655 mmol) in DCM (3 mL) is treated with a HCl solution in dioxane (4 M, 3.0 mL, 12 mmol, 18 eq) and the mixture is stirred at RT overnight. All volatiles are removed under reduced pressure to afford intermediate 15a which is used without further purification.

Step 2: A mixture of cyclopropane carboxaldehyde (73 µL, 0.983 mmol, 1.5 eq) in aqueous sodium bisulfite (40%, 0.75 mL) is stirred at RT for 1 h. This mixture is transferred to a solution containing 15a (287 mg, 0.655 mmol) in EtOH (6 mL) and is heated at 80° C. overnight. Water and EtOAc are added. The aqueous layer is separated, acidified with a HCl 1N solution and extracted with EtOAc (3×5 mL). The combined organic layers are dried over MgSO$_4$, filtered and concentrated to afford intermediate 15b.

Step 3: Intermediate 15c is prepared analogously to the procedure described in example 7, step 4. Using 15b (83 mg, 0.184 mmol) and the hydrochloride salt of intermediate 8002 (34 mg, 0.277 mmol, 1.5 eq), intermediate 15c is isolated and used without further purification.

Step 4: To a solution of 15c (74 mg, 0.143 mmol) in DMF (1.5 mL) containing potassium carbonate (59 mg, 0.428 mmol, 3.0 eq) is added iodomethane (12 μL, 0.185 mmol, 1.3 eq).

Additional iodomethane is added to complete conversion. After being stirred for 20 h at RT, the mixture is filtered on Acrodisc and purified by reverse phase semipreparative HPLC (MeCN/water, ammonium bicarbonate pH 10). The pure fractions are combined and lyophilized to give compound 2021.

Example 16

Preparation of Compound 5004

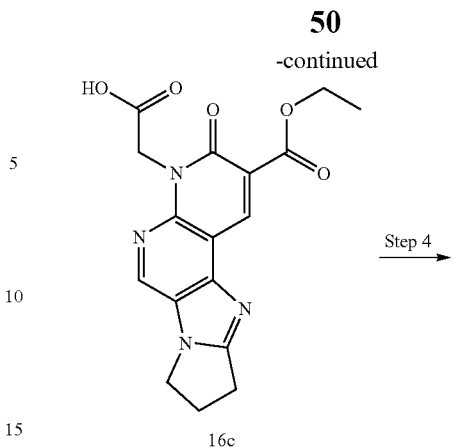

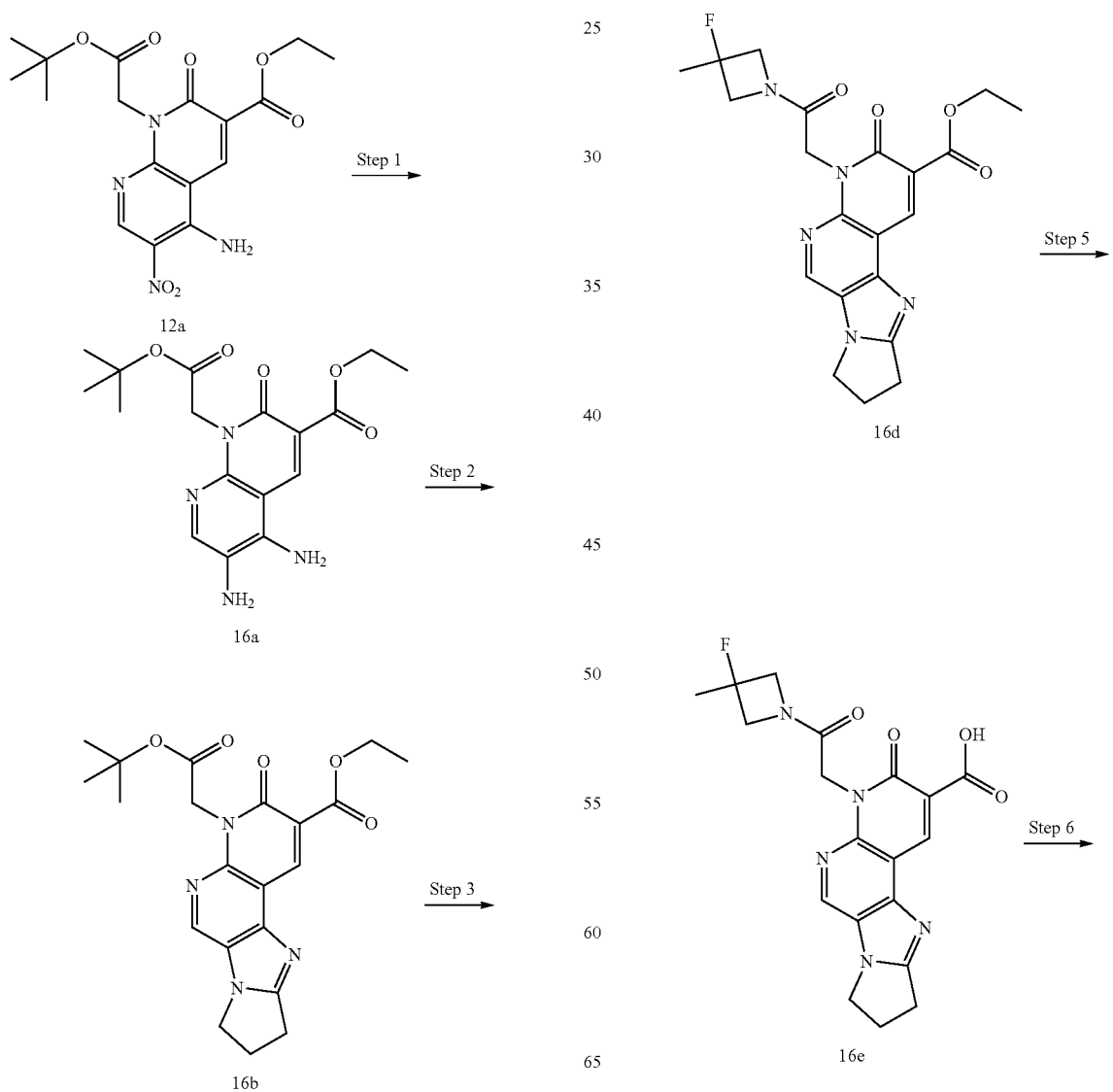

-continued

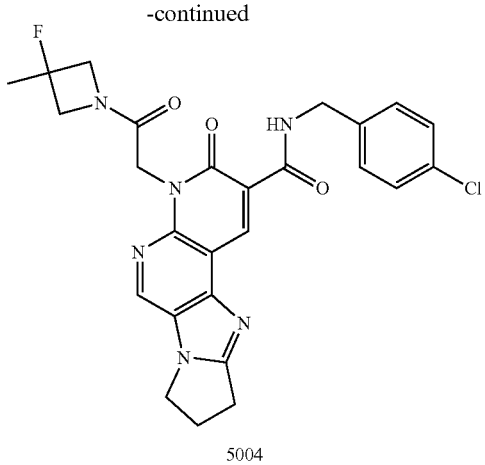

5004

Example 17

Preparation of Compounds 5029, 5030 and 5006

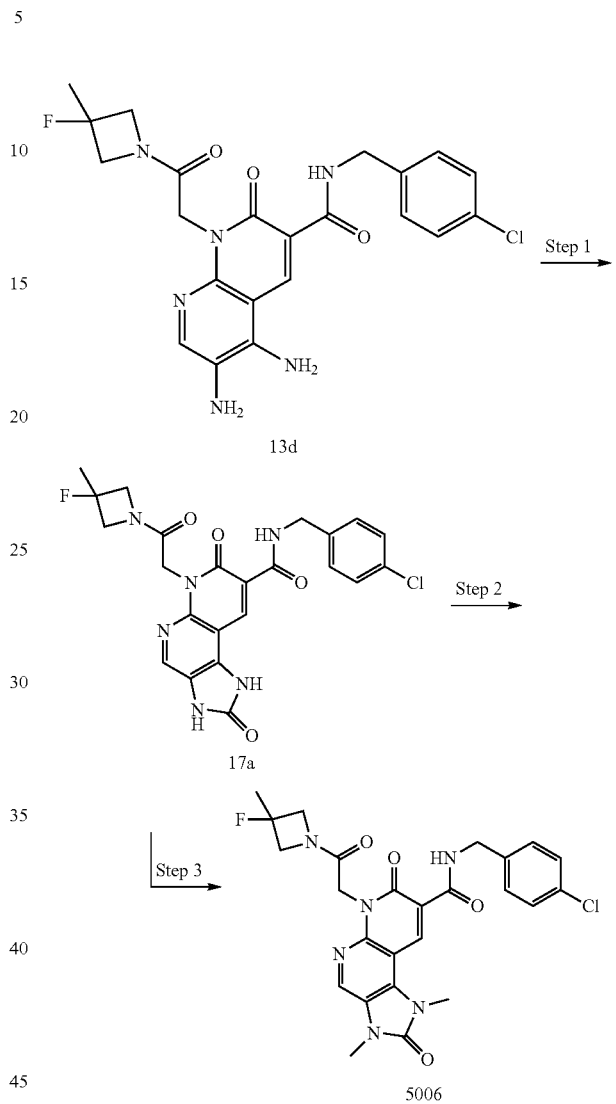

Step 1: In a round bottom flask equipped with a 3-way valve, a suspension of 12a (2.05 g, 5.23 mmol) in a mixture of MeOH/EtOAc (15 mL:10 mL) is prepared. This mixture is degassed with argon, and then 5% palladium on charcoal (~100 mg) is added. The system is purged with hydrogen using a vacuum/back filling technique. This mixture is stirred for 6 h under a hydrogen atmosphere. When the reaction is complete, the system is purged with argon (vacuum/back filling). The mixture is filtered over celite and rinsed with MeOH. The filtrate is concentrated to dryness to afford intermediate 16a which is used without further purification.

Step 2: In a flask containing 4-bromo-1,1,1-trimethoxy butane (282 mg, 1.24 mmol, 1.5 eq) in DCM (2 mL) is added TFA (13 µl, 0.166 mmol, 0.2 eq). This mixture is stirred for 5 min, then transferred to a solution of 16a (300 mg, 0.828 mmol) in DCM (3 mL). The reaction mixture is stirred at RT overnight, then the volatiles are removed under reduced pressure. Water is added and the mixture is extracted with EtOAc (3×10 mL). The organic layers are combined, dried over MgSO$_4$, filtered and concentrated. The crude residue is dissolved in DMF (5 mL) and solid potassium carbonate (228 mg, 1.66 mmol, 2.0 eq) is added. After being stirred for 45 min, water is added and the mixture is extracted with EtOAc (3×10 mL). The organic layers are combined, dried over MgSO$_4$, filtered and concentrated. The residue is purified by Combiflash (12 g silica gel column; eluents: hexanes/EtOAc (gradient 20% to 100%)), then with a mixture of DCM/MeOH (gradient 0% to 20%). The pure fractions are combined and concentrated to afford intermediate 16b.

Step 3: Intermediate 16c is prepared analogously to the procedure described in example 12, step 6.

Step 4: Intermediate 16d is prepared analogously to the procedure described in example 12, step 7.

Step 5: Intermediate 16e is prepared analogously to the procedure described in example 12, step 2.

Step 6: Compound 5004 is prepared analogously to the procedure described in example 12, step 3.

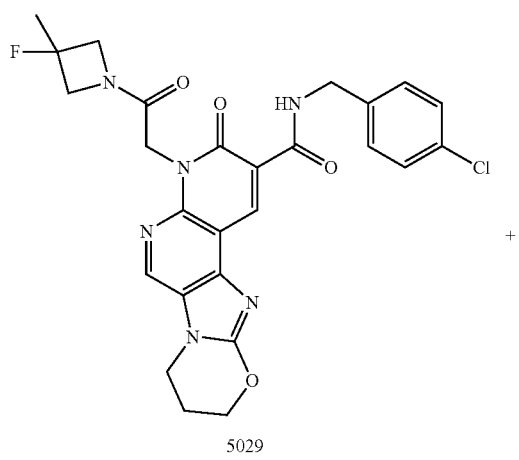

5029
+

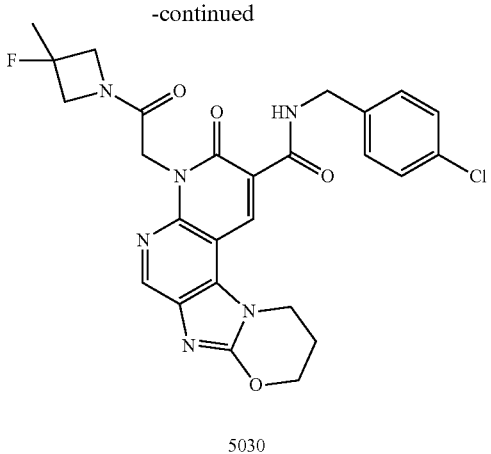

5030

Step 1: To a solution of 13d (484 mg, 1.023 mmol) in THF (10 mL) is added carbonyl diimidazole (249 mg, 1.535 mmol, 1.5 eq). The reaction mixture is warmed at 70° C. overnight. Water and EtOAc are added and the aqueous layer is extracted with EtOAc (3×5 mL). The organic layers are washed with brine, dried over MgSO₄, filtered and concentrated under reduced pressure to afford intermediate 17a which is used without further purification.

Step 2: Potassium carbonate (50 mg, 0.361 mmol, 3.0 eq) and 1,3-diiodopropane (17 μL, 0.144 mmol, 1.2 eq) are added to a solution of 17a (60 mg, 0.120 mmol) in DMF (1.2 mL). The mixture is warmed at 50° C. for 2.5 h. After being cooled to RT, the mixture is filtered on Acrodisc, purified by reverse phase semipreparative HPLC (MeCN/water, ammonium bicarbonate pH 10) and the fractions are lyophilized to give a mixture of compounds 5030/5029. This mixture is repurified by semipreparative supercritical fluid chromatography to afford compound 5030 and compound 5029.

Step 3: To a solution of 17a (50 mg, 0.100 mmol) in DMF (0.8 mL) containing potassium carbonate (41 mg, 0.301 mmol, 3 eq) is added iodomethane (425 μL, 0.401 mmol, 4.0 eq). After being stirred for 5 h at 70° C., the mixture is filtered on Acrodisc and purified by reverse phase semipreparative HPLC (MeOH/water, ammonium formate pH 3.8). The pure fractions are combined and lyophilized to give compound 5006.

Example 18

Preparation of Compound 2017

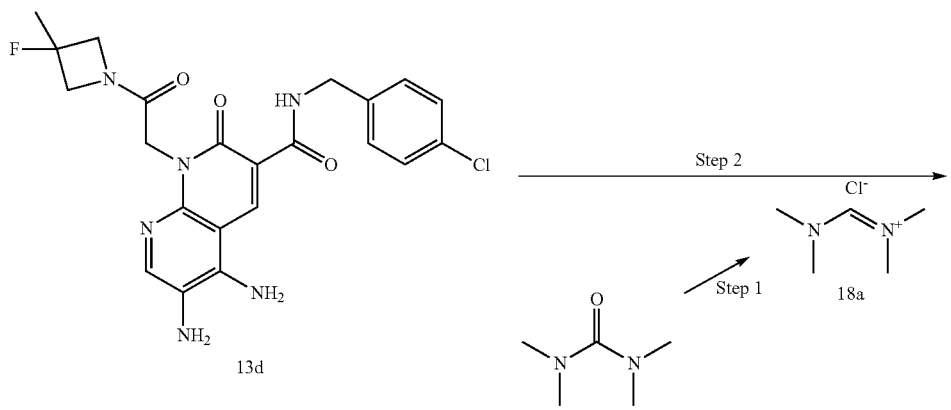

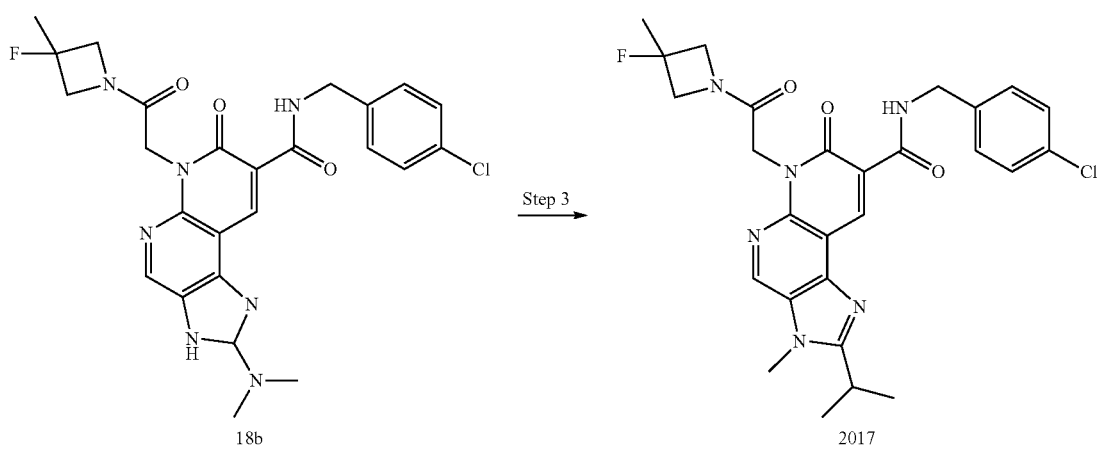

Step 1: To a solution of tetramethylurea (2.0 mL, 17.01 mmol) in DCE (25 mL) is added oxalyl chloride (4.0 mL, 47.63 mmol, 2.8 eq). The mixture is stirred at 60° C. for 1.5 h, and then the volatiles are removed under reduced pressure. The crude residue is put under high vacuum for 20 h to afford the salt 18a.

Step 2: A mixture of 13d (30 mg, 0.063 mmol), 18a (16 mg, 0.093 mmol, 1.5 eq) and Et$_3$N (27 μL, 0.190 mmol, 3.0 eq) is prepared in DCM (0.5 mL) and stirred at RT for 5 h. This reaction mixture is then warmed at 40° C. overnight. All volatiles are removed under reduced pressure to afford the crude residue 18b, which is used directly without further purification.

Step 3: To a solution of 18b (33 mg, 0.063 mmol) in DMF (1 mL) containing potassium carbonate (26 mg, 0.190 mmol, 3.0 eq) is added iodomethane (6 μL, 0.095 mmol, 1.5 eq) and the mixture is stirred at 60° C. overnight. Additional iodomethane is added to complete the conversion. The mixture is filtered on Acrodisc and purified by reverse phase semipreparative HPLC (MeCN/water, ammonium bicarbonate pH 10). The pure fractions are combined and lyophilized to give compound 2017.

Example 19

Preparation of Compounds 1044, 1048, 1002 and 1012

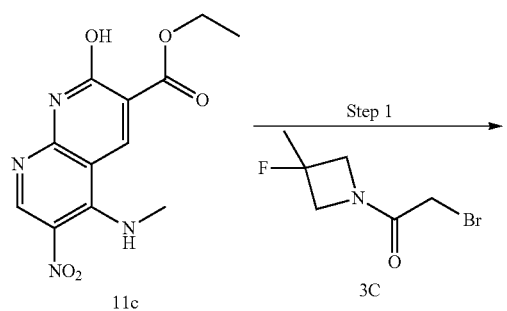

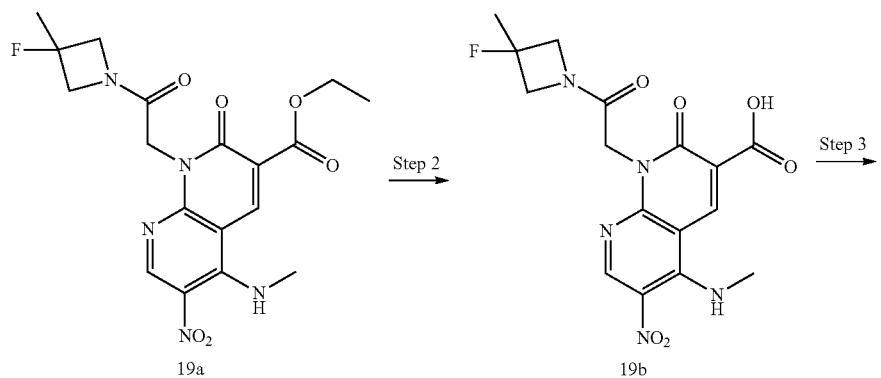

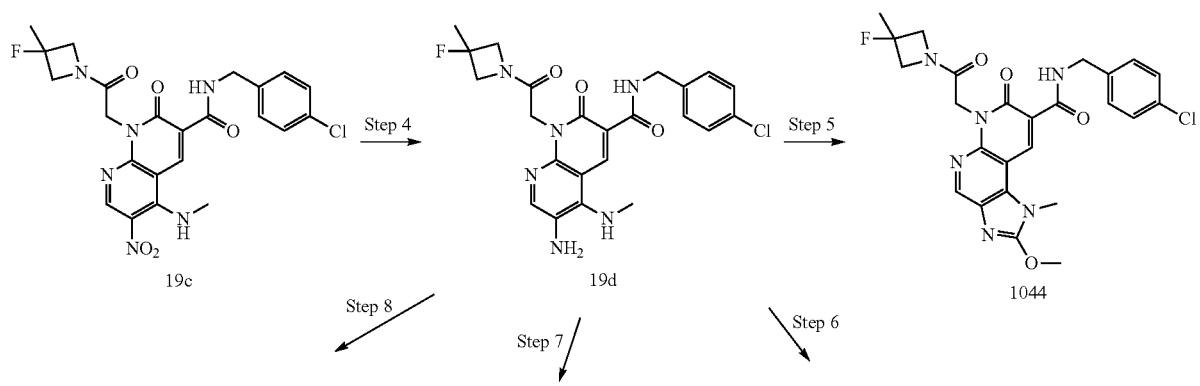

-continued

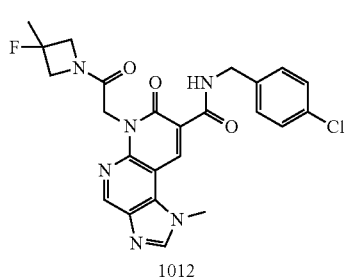
1012

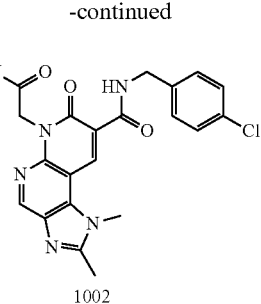
1002

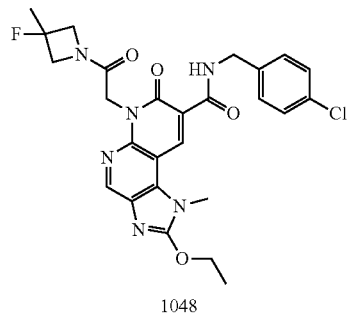
1048

Step 1: Intermediate 19a is prepared analogously to the procedure described in example 4, step 1 using 11c (3.91 g, 13.36 mmol) and 3C (3.29 g, 15.37 mmol, 1.15 eq).

Step 2: Intermediate 19b is prepared analogously to the procedure described in example 12, step 2.

Step 3: Intermediate 19c is prepared analogously to the procedure described in example 12, step 3.

Step 4: Intermediate 19d is prepared analogously to the procedure described in example 12, step 4 (Method A).

Step 5: In a flask containing tetramethylortho carbonate (98 mg, 0.719, 7.0 eq) in MeOH (0.8 mL) is added TFA (2 μL, 0.010 mmol, 0.1 eq). This mixture is stirred for 5 min, and then transferred to a solution of 19d (50 mg, 0.103 mmol) in MeOH (0.5 mL). The reaction mixture is stirred at 60° C. for 3 h. The crude residue is purified by reverse phase semi-preparative HPLC (MeOH/water, ammonium formate pH 3.8). The pure fractions are combined and lyophilized to give compound 1044.

Step 6: Compound 1048 is prepared analogously to the procedure described in step 5, but using tetraethyl orthocarbonate.

Step 7: Compound 1002 is prepared analogously to the procedure described in step 5, but using trimethyl orthoacetate.

Step 8: Compound 1012 is prepared analogously to the procedure described in step 5, but using trimethyl orthoformate.

Example 20

Preparation of Compounds 5018 and 5031

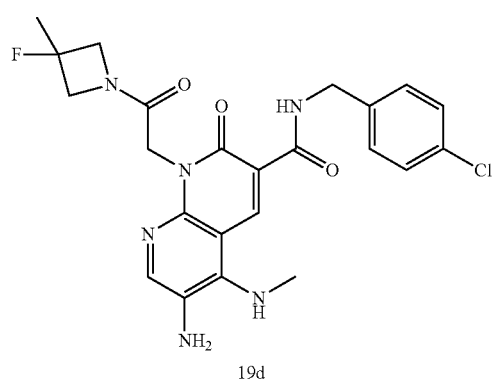
19d

-continued

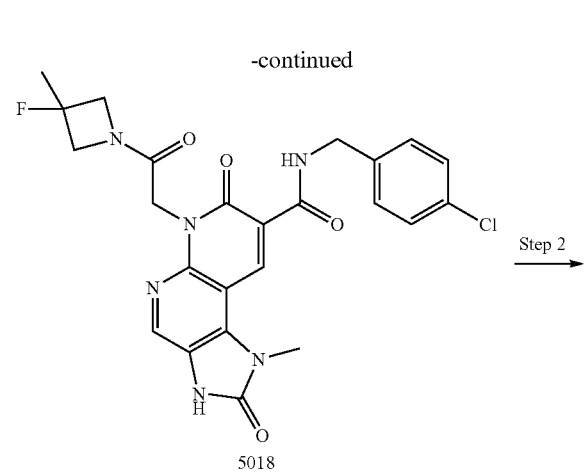
5018

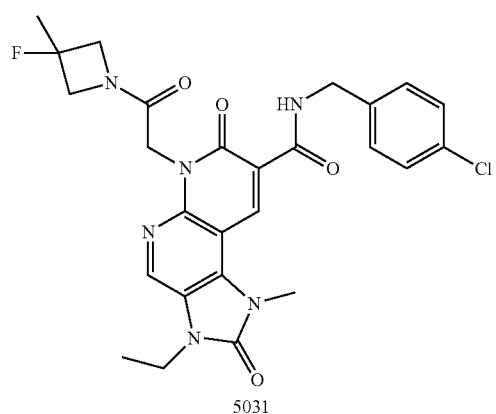
5031

Step 1: Compound 5018 is prepared analogously to the procedure described in example 17, step 1.

Step 2: To a solution of compound 5018 (30 mg, 0.058 mmol) in DMF (0.5 mL) containing potassium carbonate (24 mg, 0.175 mmol, 3.0 eq) is added iodoethane (9 μL, 0.117 mmol, 2.0 eq) and the mixture is stirred at 50° C. for 2 h. The mixture is filtered on Acrodisc and purified by reverse phase semipreparative HPLC (MeOH/water, ammonium formate pH 3.8). The pure fractions are combined and lyophilized to give compound 5031.

Example 21

Preparation of Compound 1009

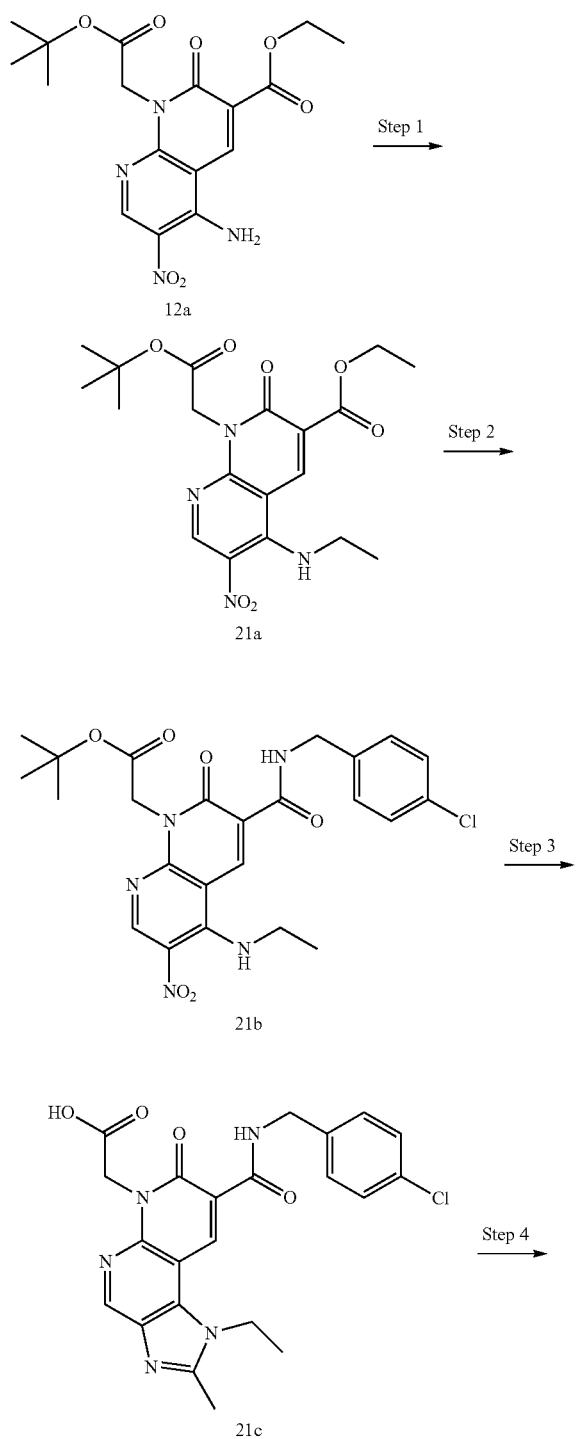

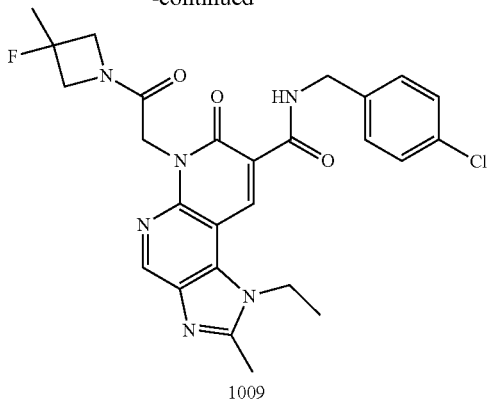

Step 1: To a solution of 12a (530 mg, 1.35 mmol) in DMF (2 mL) containing potassium carbonate (280 mg, 2.03 mmol, 1.5 eq) is added iodoethane (216 µL, 2.70 mmol, 2.0 eq) and the mixture is stirred at 80° C. overnight. The reaction is cooled to RT and water is added. The mixture is extracted with EtOAc (3×10 mL). The combined organic layers are washed with brine, dried over $MgSO_4$, filtered and concentrated. The crude residue is purified by Combiflash (12 g silica gel column; eluents: hexanes/EtOAc (gradient 10% to 100%)). The pure fractions are combined and concentrated to afford intermediate 21a.

Step 2: To a solution of 21a (415 mg, 0.987 mmol) in a mixture of THF (7 mL)/MeOH (2 mL)/water (2 mL) is added an aqueous solution of LiOH (2M, 0.54 mL, 1.086 mmol, 1.1 eq). The reaction mixture is stirred at RT for 60 min, and then the solvents are removed under reduced pressure. The residue is dissolved in DCM (20 mL) and washed with a saturated $NH_4Cl$ solution (2×10 mL). The organic layers are dried over $MgSO_4$, filtered and concentrated under reduced pressure. After drying under high vacuum for 1 day, the crude residue is dissolved in DMF (15 mL). Diisopropylethylamine (0.52 mL, 2.96 mmol, 2.0 eq), 4-chlorobenzylamine (0.24 mL, 1.974 mmol, 2.0 eq) and HATU (750 mg, 1.974 mmol, 2.0 eq) are successively added. The reaction mixture is stirred at RT for 30 min, then all volatiles are removed under reduced pressure at 80° C. The crude residue is purified by Combiflash (12 g silica gel column; eluents:hexanes/EtOAc (gradient 10% to 100%)). The pure fractions are combined and concentrated to afford intermediate 21 b.

Step 3: In a sealed tube, a solution of 21b (80 mg, 0.155 mmol) in acetic acid (2 mL) containing iron dust (69 mg, 1.240 mmol, 8.0 eq) is warmed at 120° C. overnight. After being cooled to RT, the mixture is filtered over celite and rinsed with EtOAc. The filtrate is concentrated to dryness and azeotroped three times with toluene to remove residual water. The intermediate 21c is isolated and used in the next step without purification.

Step 4: Compound 1009 is prepared analogously to the procedure described in example 7, step 4. Using 21c (70 mg, 0.155 mmol) and the hydrochloride salt of intermediate 8001 (39 mg, 0.308 mmol, 2.0 eq), compound 1009 is obtained after being purified by reverse phase semipreparative HPLC (MeOH/water, ammonium bicarbonate, pH 10).

Example 22

Preparation of Compounds 1004 and 1005

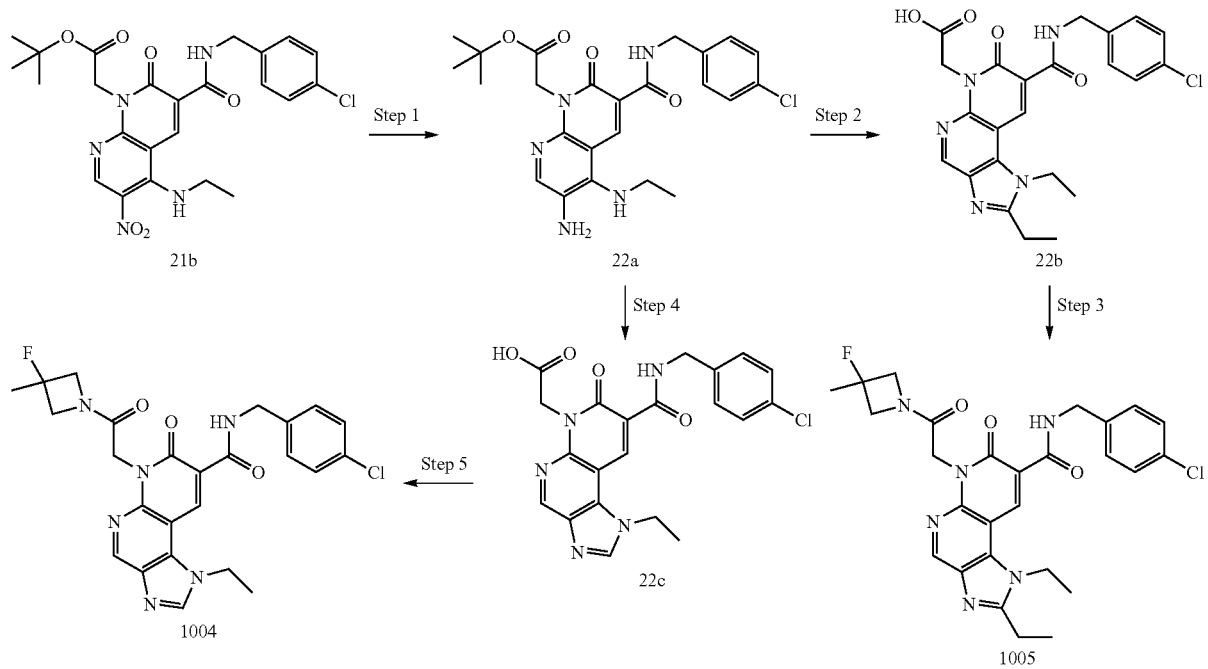

Step 1: Intermediate 22a is prepared analogously to the procedure described in example 12, step 4 (method A) using 21b (300 mg, 0.580 mmol).

Step 2: To a flask containing triethyl orthopropionate (0.35 mL, 1.75 mmol, 10 eq) is added TFA (5 µL, 0.028 mmol, 0.15 eq). This mixture is stirred for 5 min, then transferred to a solution of 22a (85 mg, 0.175 mmol) in DCM (1 mL). The reaction mixture is stirred at RT for 3 h. TFA (2 mL) is added and the mixture is stirred at RT for 2 h. All volatiles are removed under reduced pressure to afford the crude intermediate 22b, which is directly used in the the next step.

Step 3: Compound 1005 is prepared analogously to the procedure described in example 7, step 4. Using crude 22b (81 mg, 0.175 mmol) and the hydrochloride salt of intermediate 8001 (60 mg, 0.481 mmol, 2.8 eq), compound 1005 is obtained after purification by reverse phase semipreparative HPLC (MeOH/water, ammonium bicarbonate, pH 10).

Step 4: In a flask containing trimethyl orthoformate (0.15 mL, 1.40 mmol, 10 eq) is added TFA (3 µL, 0.028 mmol, 0.2 eq). This mixture is stirred for 5 min, then transferred to a solution of 22a (68 mg, 0.140 mmol) in DCM (1 mL). The reaction mixture is stirred at RT for 3 h. TFA (2 mL) is added and this mixture is stirred at RT for 2 h. All volatiles are removed under reduced pressure to provide the crude intermediate 22c, which is directly used in the next step.

Step 5: Compound 1004 is prepared according to the procedure described in example 7, step 4. Using crude 22c (61 mg, 0.139 mmol) and the hydrochloride salt of intermediate 8001 (34 mg, 0.273 mmol, 2.0 eq), compound 1004 is obtained after purification by reverse phase semipreparative HPLC (MeOH/water, ammonium bicarbonate, pH 10).

Example 23

Preparation of Compound 5002

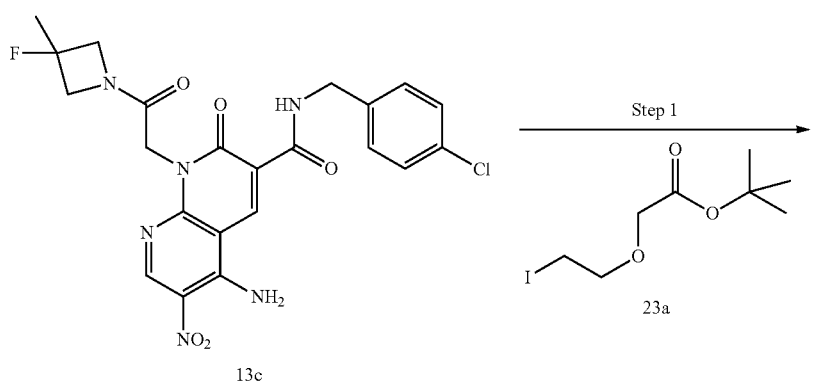

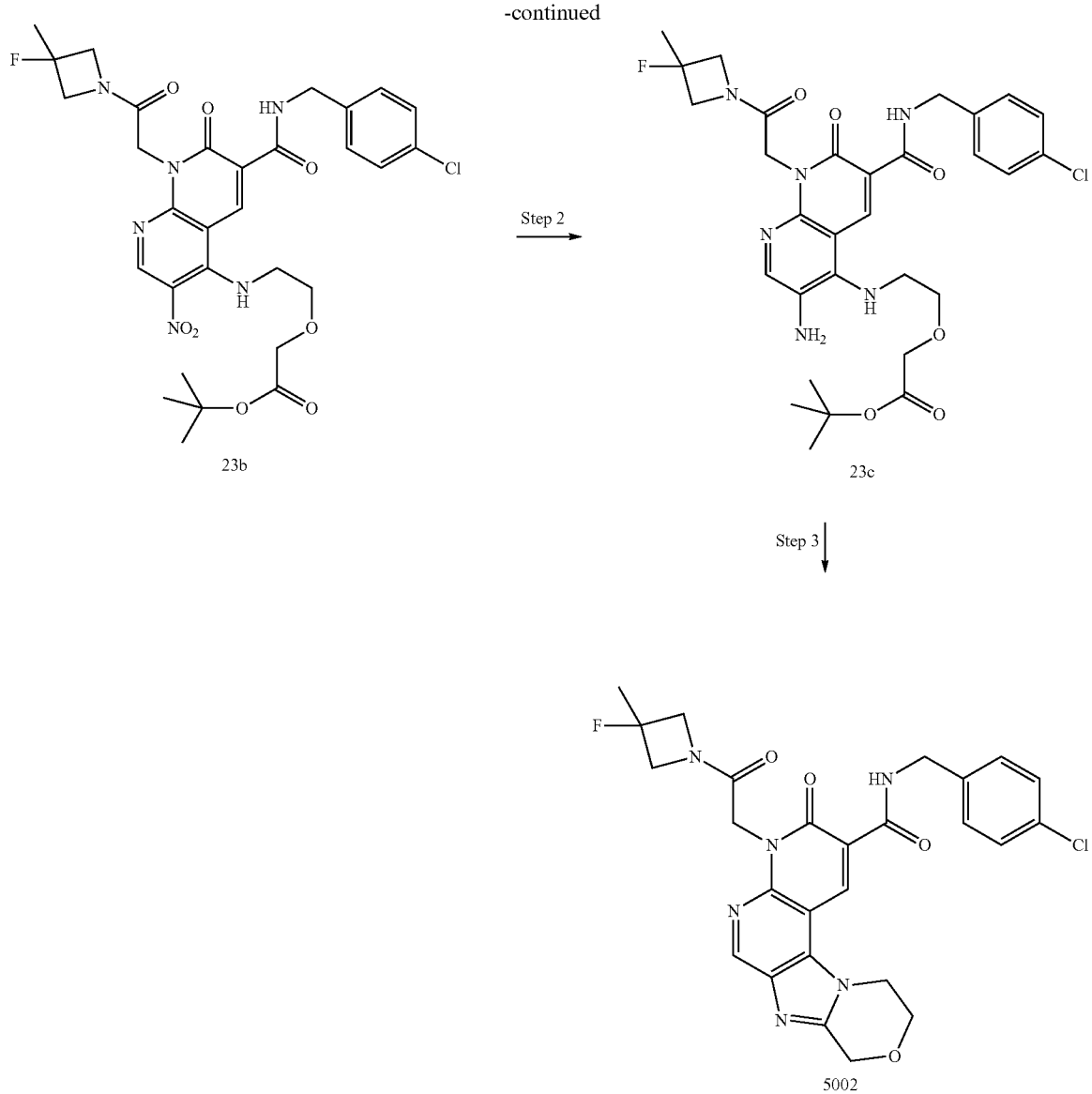

Step 1: Intermediate 23b is prepared analogously to the procedure described in example 21, step 1 using 13c (339 mg, 0.674 mmol) and 23a (482 mg, 1.685 mmol, 2.5 eq).

Preparation of intermediate 23a: (procedure is analogous to that described in WO2009/147121, herein incorporated by reference). To a solution of t-butyl bromoacetate (12.0 g, 61.5 mmol) in DMF (20 mL) is added a solution of 2-chloroethanol (4.95 g, 61.5 mmol) in DMF (5 mL). The mixture is cooled at 0° C. and pellets of NaOH (2.95 g, 73.8 mmol, 1.2 eq) are added. The reaction mixture is stirred at 0° C. for 2 h, then at RT overnight. Water and heptane are added, and the mixture is extracted with MTBE (3×20 mL). The organic layers are combined, washed with water (50 mL), dried over Na$_2$SO$_4$, filtered and evaporated. To this crude material (2.0 g, 10.3 mmol) in THF (15 mL) is added sodium iodide (3.08 g, 20.5 mmol, 2.0 eq) and this reaction mixture is warmed at 70° C. overnight. Water and EtOAc are added. The layers are separated and the aqueous phase is extracted with EtOAc (3×10 mL). The organic layers are combined, dried over Na$_2$SO$_4$, filtered and evaporated to afford crude 23a which is used without further purification.

Step 2: Intermediate 23c is prepared analogously to the procedure described in example 12, step 4 (method A) using 23b (401 mg, 0.605 mmol).

Step 3: To a solution of 23c (160 mg, 0.254 mmol) in DCM (1 mL) is added TFA (1 mL). The mixture is stirred for 1 h, then all volatiles are concentrated under reduced pressure. This crude residue is dissolved in DMF (8 mL), diisopropylethylamine (0.23 mL, 0.761 mmol, 3.0 eq) and HATU (193 mg, 0.507 mmol, 2.0 eq) are successively added, and the mixture is stirred at RT for 2 h. All volatiles are then removed under reduced pressure, and DCM/TFA (1 mL:1 mL) are added. After being stirred for 1 h, the mixture is concentrated under reduced pressure and purified by reverse phase semi-preparative HPLC (MeCN/water, 0.06% TFA buffer). The pure fractions are combined and lyophilized to give compound 5002.

Example 24

Preparation of Compounds 1029, 1031 and 5035

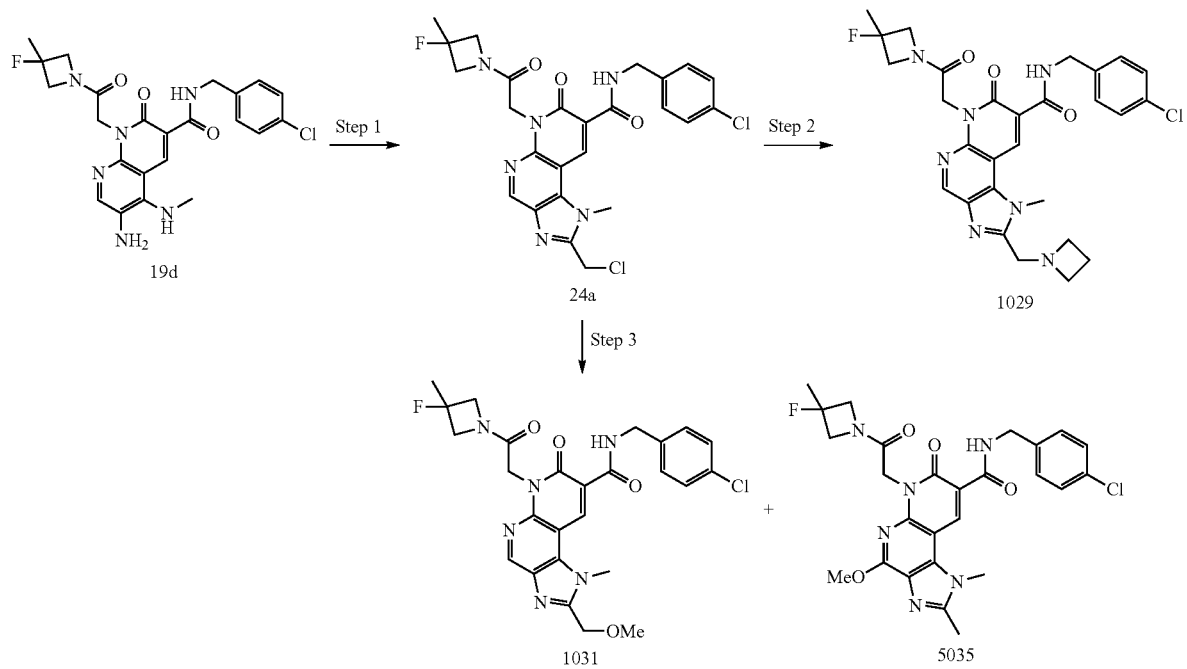 [SMILES: CNc1c(N)cnc2c1cc(C(=O)NCc1ccc(Cl)cc1)c(=O)n2CC(=O)N1CC(C)(F)C1 ; Cn1c(CCl)nc2cnc3c(cc(C(=O)NCc4ccc(Cl)cc4)c(=O)n3CC(=O)N3CC(C)(F)C3)c21 ; Cn1c(CN2CCC2)nc2cnc3c(cc(C(=O)NCc4ccc(Cl)cc4)c(=O)n3CC(=O)N3CC(C)(F)C3)c21 ; COCc1nc2cnc3c(cc(C(=O)NCc4ccc(Cl)cc4)c(=O)n3CC(=O)N3CC(C)(F)C3)c2n1C ; COc1nc2c(cc(C(=O)NCc3ccc(Cl)cc3)c(=O)n2CC(=O)N2CC(C)(F)C2)c2c1nc(C)n2C]

Step 1: Intermediate 19d (500 mg, 1.027 mmol) is charged in a flask in DCM (5 mL) along with 2-chloro-1,1,1-triethoxyethane (0.98 mL, 5.134 mmol, 5.0 eq) and TFA (25 µL, 0.339 mmol, 0.3 eq). After being stirred for 1 h, all volatiles are removed under reduced pressure to afford the crude intermediate 24a, which is directly used in the next step.

Step 2: To a solution of 24a (40 mg, 0.073 mmol) in NMP (0.5 mL) is added Et$_3$N (20 µL, 0.147 mmol, 2.0 eq), sodium iodide (5.5 mg, 0.037 mmol, 0.5 eq) and azetidine (13 mg, 0.220 mmol, 3.0 eq). The mixture is stirred at 70° C. for 4 h. The mixture is filtered on Acrodisc and purified by reverse phase semipreparative HPLC (MeCN/water, formic acid buffer with column heater 45° C.). The pure fractions are combined and lyophilized to give compound 1029.

Step 3: To a solution of 24a (50 mg, 0.092 mmol) is added a solution of sodium methoxide in MeOH (0.5M, 3 mL, 1.5 mmol, 16 eq) and the mixture is stirred at RT overnight. The mixture is filtered on Acrodisc and purified by reverse phase semipreparative HPLC (MeCN 0.06% TFA). Two products are isolated which correspond to compounds 1031 and 5035.

Example 25

Preparation of Compounds 1049 and 1006

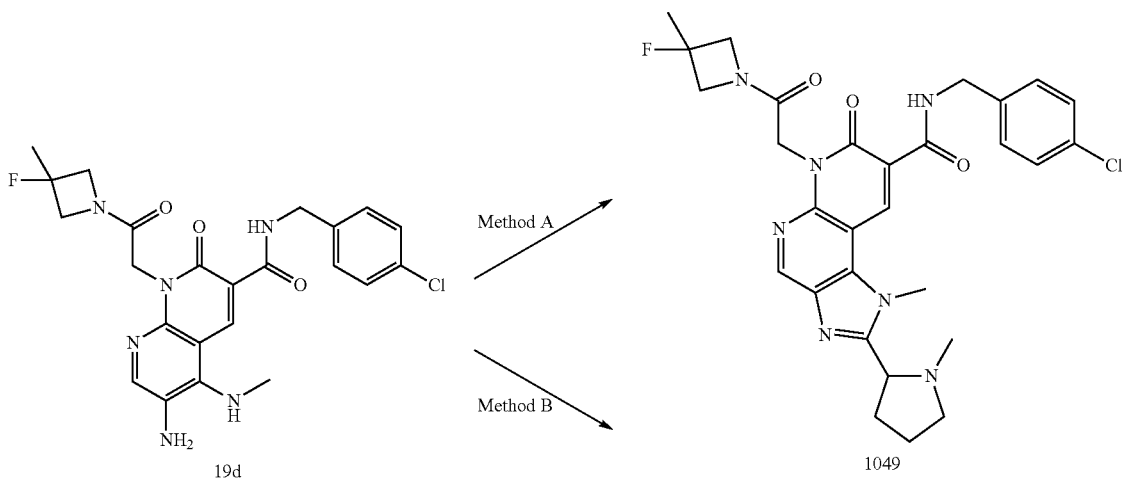

-continued

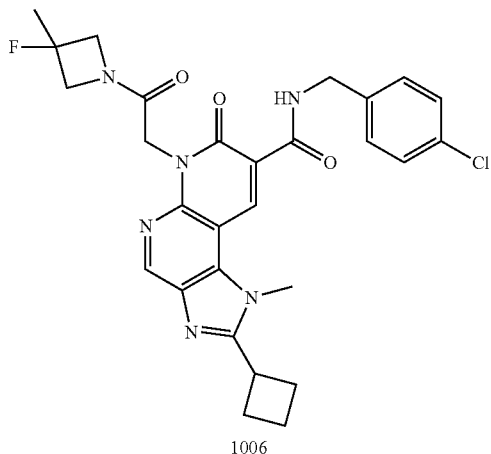

1006

Method A: In a microwave tube, intermediate 19d (50 mg, 0.103 mmol) is charged in a flask in DMF (0.6 mL) with 1-methylpyrrolidine-2-carboxylic acid (27 mg, 0.164 mmol, 1.6 eq), diisopropylethylamine (71 μL, 0.411 mmol, 4.0 eq), and HATU (59 mg, 0.154 mmol, 1.5 eq). The mixture is stirred at RT for 3.5 h. DCE (2 mL) and MgSO$_4$ (approximately 50 mg) are added. The flask is capped and put in a microwave at 150° C. for 10 min (3×). The mixture is passed through a phase separator cartridge, and then the filtrate is purified by reverse phase semipreparative HPLC (MeCN/water, formic acid buffer with column heater 45° C.). The pure fractions are combined and lyophilized to give compound 1049.

Method B: A solution of cyclobutane carboxaldehyde (7.6 mg, 0.090 mmol, 1.1 eq) in aqueous sodium bisulfite (40%, 94 μL, 0.361, 4.4 eq) is stirred at RT for 1 h. A solution of 19d (40 mg, 0.82 mmol) in EtOH (1 mL) is then transferred to the previous mixture and the reaction is heated at 80° C. overnight. Additional aldehyde and sodium bisulfite are added to complete the conversion. A minimal amount of water and DMSO are added, and then the mixture is filtered on Acrodisc and purified by reverse phase semipreparative HPLC (MeCN/water, 0.06% TFA buffer). The pure fractions are combined and lyophilized to give compound 1006.

Example 26

Preparation of Compound 1016

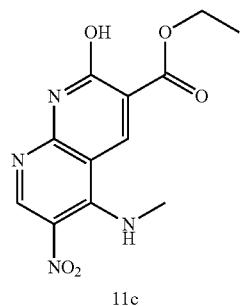

11c

Step 1 →

-continued

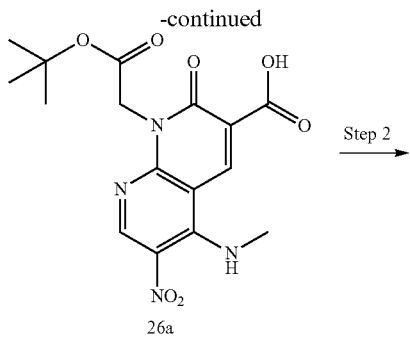

26a

Step 2 →

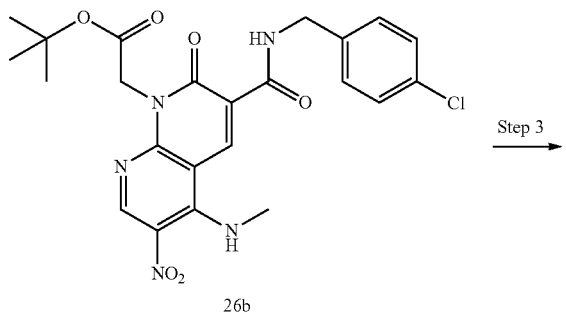

26b

Step 3 →

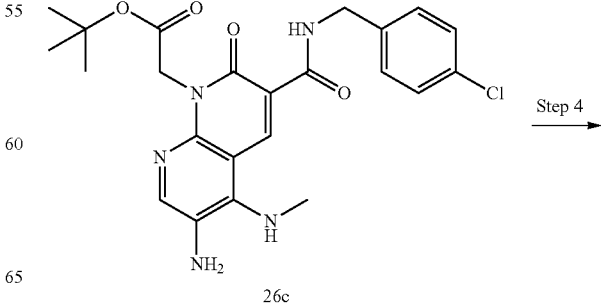

26c

Step 4 →

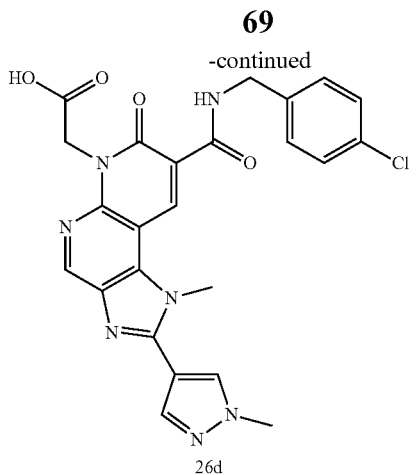

26d

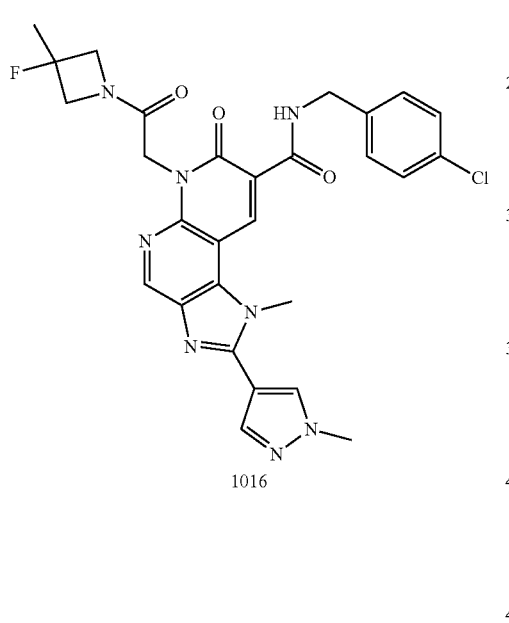

1016

Step 1: Intermediate 26a is prepared analogously to the procedure described in example 12, steps 1 and 2.

Step 2: Intermediate 26b is prepared analogously to the procedure described in example 12, step 3.

Step 3: Intermediate 26c is prepared analogously to the procedure described in example 12, step 4 (method A).

Step 4: (analogous to the procedure described in Synthesis 2003, 1683-1692, herein incorporated by reference) To a solution of intermediate 26c (50 mg, 0.106 mmol) and 1-methyl-1H-pyrazole-4-carbaldehyde (17 mg, 0.159 mmol, 1.5 eq) in DMF/water (3 mL:0.1 mL) is added oxone (42 mg, 0.069 mmol). The mixture is vigorously stirred at RT for 1 h, then water (5 mL) is added and the mixture is extracted with DCM (3×5 mL). The organic layers are dried by passing through a phase separator cartridge and the filtrate is concentrated under reduced pressure. The residue is dissolved in DCM (2 mL) and TFA (1 mL) is added. After being stirred for 20 h, all volatiles are removed under reduced pressure to afford crude intermediate 26d, which is directly used without further purification.

Step 5: Compound 1016 is prepared analogously to the procedure described in example 7, step 4.

Example 27

Preparation of Compound 1053

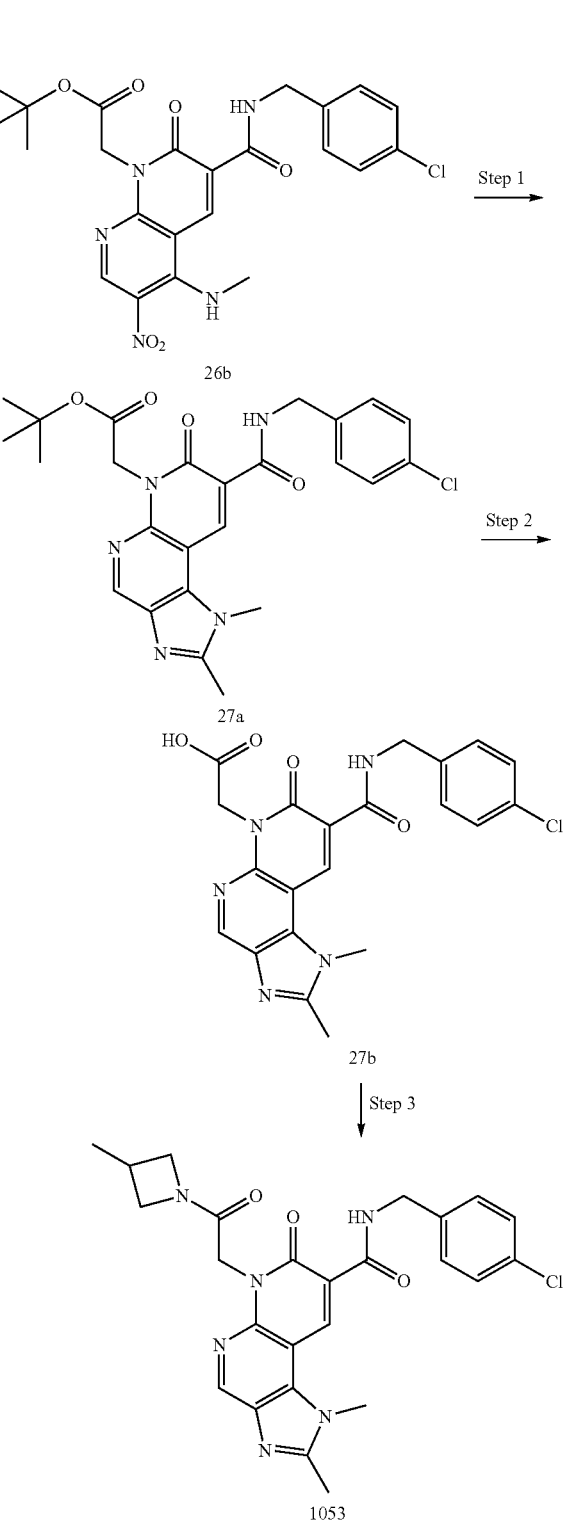

Step 1: A solution of intermediate 26b (3.08 g, 6.13 mmol) in MeOH (200 mL) is degassed by bubbling an argon stream for 15 min. Then 1% platinum on carbon, vanadium doped (342 mg, 6.13 mmol, 1 eq) is added and the reaction is stirred under a hydrogen atmosphere at 50° C. for 1 h. The system is purged with argon (vacuum/back filling). The mixture is filtered over celite and rinsed thoroughly with MeOH, and the filtrate is concentrated to dryness. The crude residue is dissolved in DCM (100 mL) and triethyl orthoacetate (1.7 mL, 9.20 mmol, 1.5 eq) is added followed by TFA (91 µL, 1.23 mmol, 0.2 eq). This reaction mixture is stirred at RT for 8 h, then a saturated aqueous solution of NaHCO$_3$ (100 mL) is added. The layers are separated and the aqueous phase is extracted with EtOAc (3×50 mL). The organics are combined, washed with brine, dried over MgSO$_4$, filtered and concentrated. The crude residue is purified by Combiflash (80 g silica gel column; eluting with 100% EtOAc, then with a mixture of EtOAc/MeOH, gradient 0% to 8%) to afford intermediate 27a.

Step 2: To a solution of intermediate 27a (2.37 g, 4.79 mmol) in DCM (20 mL) is added TFA (10 mL) and the mixture is stirred at RT for 4 h. All volatiles are evaporated under reduced pressure and the crude residue is triturated with MTBE while sonicating for 5 min. The solid is recovered by Buchner filtration and dried under high vacuum to afford intermediate 27b.

Step 3: Compound 1053 is prepared analogously to the procedure described in example 7, step 4.

Example 28

Preparation of Compound 3001

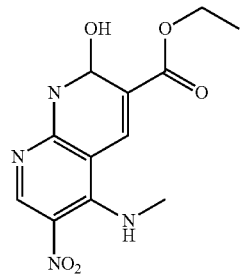
11c

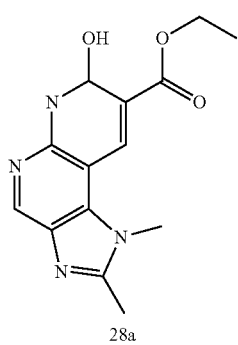
28a

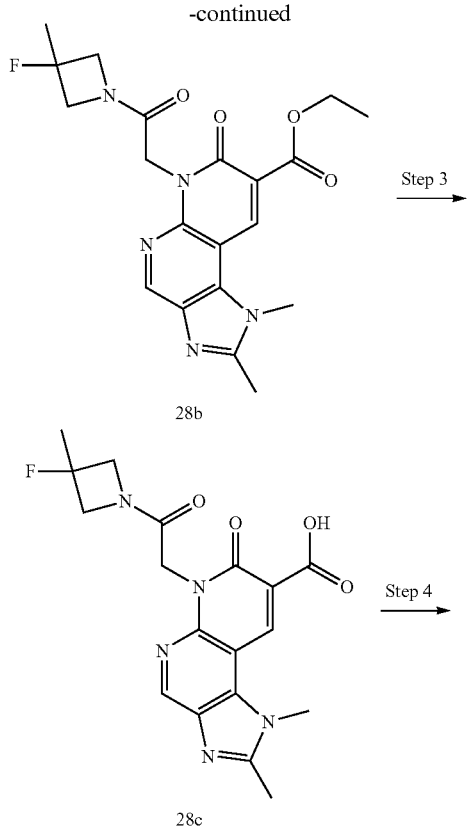
28b
28c
3001

Step 1: Activation of iron dust proceeds as follows: iron dust is washed with concentrated HCl, and then with water. The solid is kept under an inert atmosphere to prevent air oxidation. A mixture of 11c (500 mg, 1.71 mmol) and activated iron dust (100 mg, 1.79 mmol, 1.05 eq) in a mixture of EtOH (20 mL)/saturated aqueous NH$_4$Cl solution (1 mL) is warmed at 90° C. for 3 h. All volatiles are removed under reduced pressure, then glacial acetic acid (5 mL) is added and the mixture is warmed at 120° C. for 4 h. The solvents are removed under reduced pressure and the mixture is purified by preparative HPLC (MeCN, 0.06% TFA buffer). The pure fractions are combined and lyophilized to afford intermediate 28a.

Step 2: Intermediate 28b is prepared analogously to the procedure described in example 4, step 1 using 28a (130 mg, 0.454 mmol) and 3C (152 mg, 0.727 mmol, 1.6 eq).

Step 3: Intermediate 28c is prepared analogously to the procedure described in example 12, step 2.

Step 4: Compound 3001 is prepared analogously to the procedure described in example 12, step 3.

Example 29

Preparation of Compound 2020

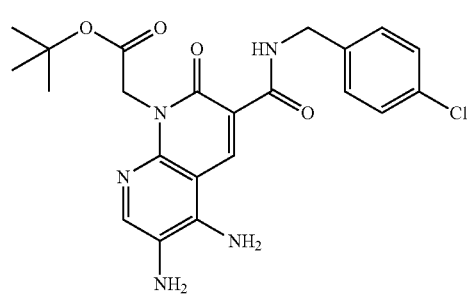
12d

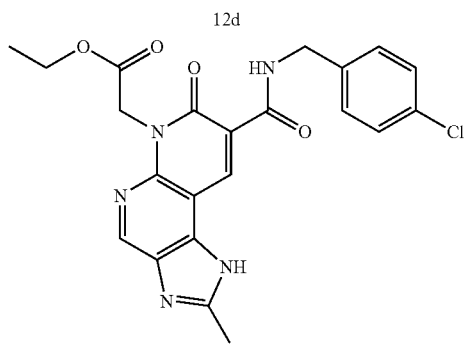
29a

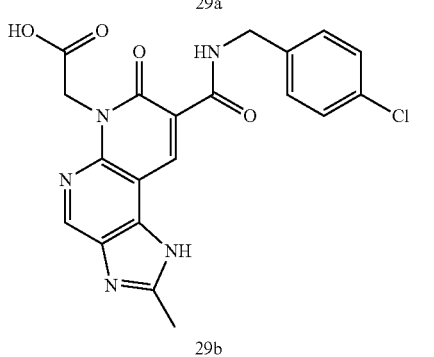
29b

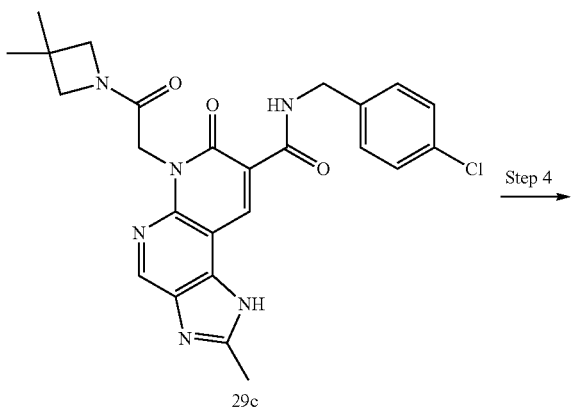
29c

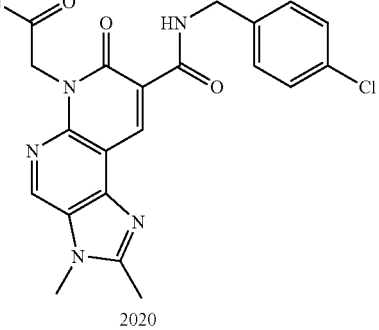
2020

Step 1: To a solution of 12d (300 mg, 0.655 mmol) in EtOH (3.3 mL) is added 2,4-pentanedione (0.135 mL, 1.31 mmol, 2.0 eq) and HCl 5N (0.33 mL, 1.64 mmol, 2.5 eq) and the mixture is warmed at 85° C. overnight. The mixture is concentrated to dryness to afford intermediate 29a which is directly used for next step.

Step 2: A solution of 29a (297 mg, 0.655 mmol) in a mixture of THF (3 mL)/MeOH (1 mL) is added a commercial solution of NaOH (1N, 2.2 mL, 2.2 mmol, 3.4 eq). The reaction mixture is stirred at room temperature overnight. The solvents are removed under reduced pressure and HCl 1N (5 mL) is added. The aqueous layer is extracted with EtOAc (4×5 mL). The organic layers are combined, dried over MgSO$_4$, filtered and concentrated to afford intermediate 29b which is directly used for next step.

Step 3: Intermediate 29c is prepared analogously to the procedure described in example 7, step 4.

Step 4: Compound 2020 is prepared analogously to the procedure described in example 15, step 4.

Example 30

Preparation of Compound 3004

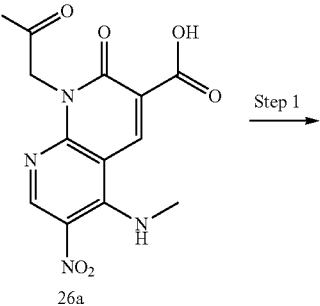
26a

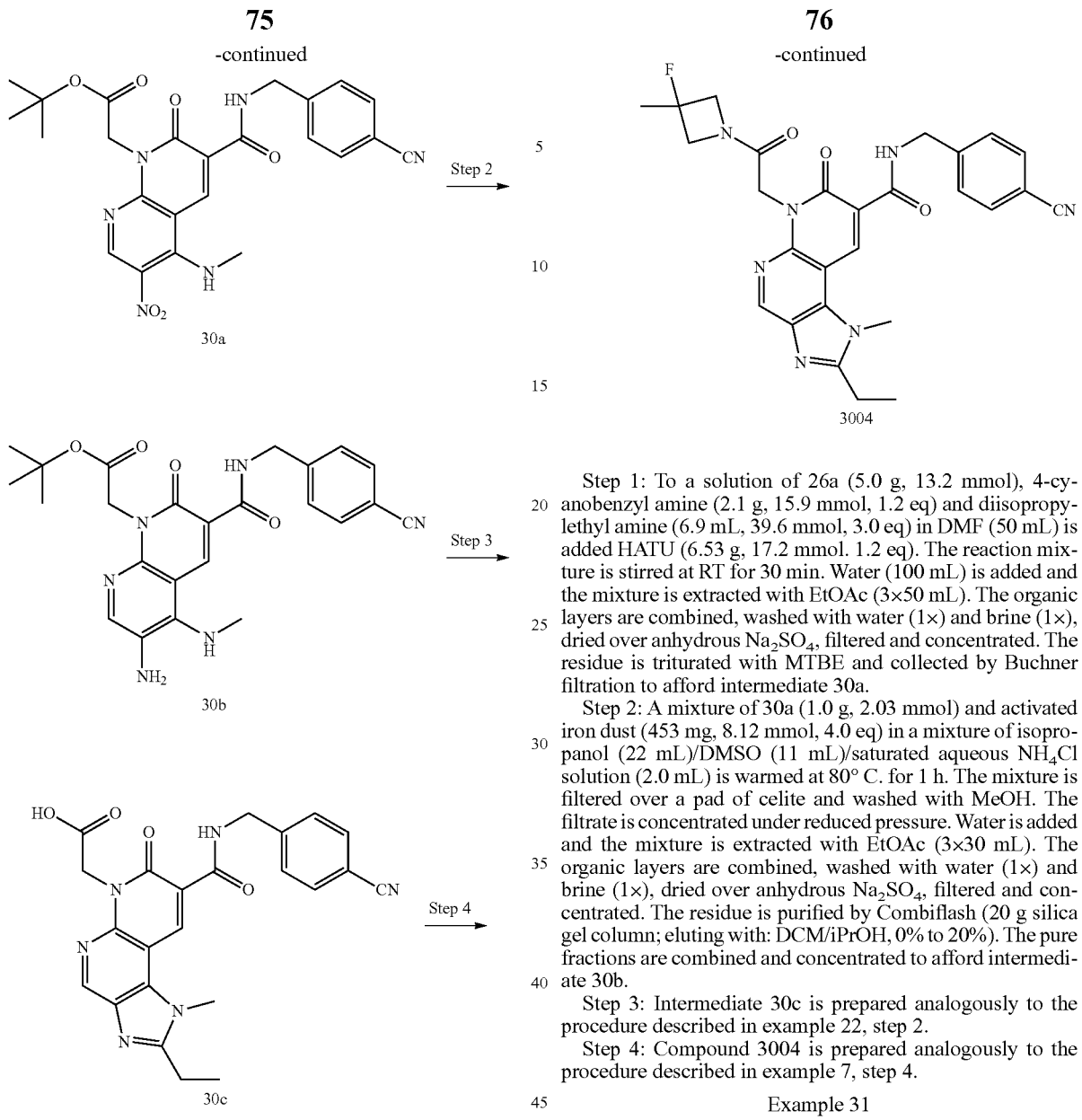

Step 1: To a solution of 26a (5.0 g, 13.2 mmol), 4-cyanobenzyl amine (2.1 g, 15.9 mmol, 1.2 eq) and diisopropylethyl amine (6.9 mL, 39.6 mmol, 3.0 eq) in DMF (50 mL) is added HATU (6.53 g, 17.2 mmol. 1.2 eq). The reaction mixture is stirred at RT for 30 min. Water (100 mL) is added and the mixture is extracted with EtOAc (3×50 mL). The organic layers are combined, washed with water (1×) and brine (1×), dried over anhydrous $Na_2SO_4$, filtered and concentrated. The residue is triturated with MTBE and collected by Buchner filtration to afford intermediate 30a.

Step 2: A mixture of 30a (1.0 g, 2.03 mmol) and activated iron dust (453 mg, 8.12 mmol, 4.0 eq) in a mixture of isopropanol (22 mL)/DMSO (11 mL)/saturated aqueous $NH_4Cl$ solution (2.0 mL) is warmed at 80° C. for 1 h. The mixture is filtered over a pad of celite and washed with MeOH. The filtrate is concentrated under reduced pressure. Water is added and the mixture is extracted with EtOAc (3×30 mL). The organic layers are combined, washed with water (1×) and brine (1×), dried over anhydrous $Na_2SO_4$, filtered and concentrated. The residue is purified by Combiflash (20 g silica gel column; eluting with: DCM/iPrOH, 0% to 20%). The pure fractions are combined and concentrated to afford intermediate 30b.

Step 3: Intermediate 30c is prepared analogously to the procedure described in example 22, step 2.

Step 4: Compound 3004 is prepared analogously to the procedure described in example 7, step 4.

Example 31

Preparation of Compounds 1040, 1034, and 1056

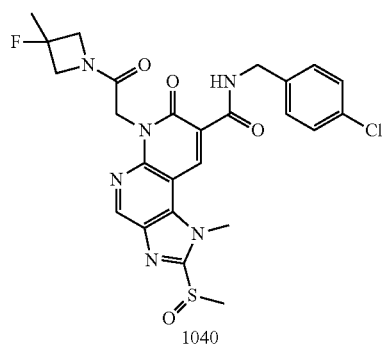

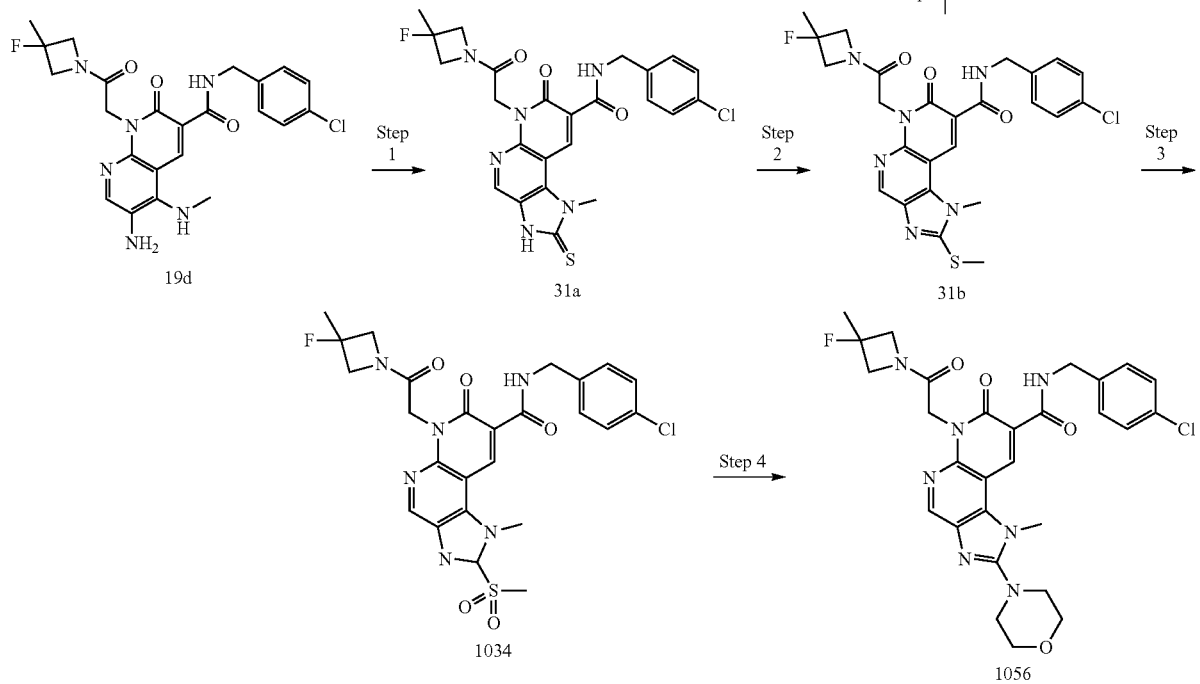

Step 1: To a solution of 19d (1.34 g, 2.758 mmol) in THF (25 mL) is added 1,1-thiocarbonylimidazole (737 mg, 4.137 mmol, 1.5 eq) and the reaction mixture is stirred at 60° C. for 15 h. Water and EtOAc are added. The layers are separated and the aqueous phase is extracted with EtOAc (3×15 mL). The organic layers are combined, washed with brine, dried over MgSO$_4$, filtered and concentrated to afford crude intermediate 31a which is used in the next step without further purification.

Step 2: Methyl iodide (0.304 mL, 4.88 mmol, 2.0 eq) is added to a solution of 31a (1.29 g, 2.439 mmol) in a mixture of EtOH (6 mL)/water (6 mL)/concentrated ammonium hydroxide (4 mL). This reaction mixture is stirred at RT for 15 h. The mixture is extracted with DCM (3×10 mL). The organic layers are combined, dried over MgSO$_4$, filtered and concentrated. The crude residue is purified by Combiflash (40 g silica gel column; eluents: DCM/MeOH, gradient 0% to 5%). The pure fractions are combined, concentrated, and dried in vacuo to afford intermediate 31 b.

Step 3: To a solution of 31 b (669 mg, 1.23 mmol) in DCM (20 mL) at 0° C. is added 3-chloroperoxybenzoic acid (77%; 608 mg, 2.71 mmol, 2.2 eq). The mixture is stirred at RT for 40 h, and then saturated NaHSO$_3$ solution is added (20 mL). The layers are separated and the aqueous phase is extracted with DCM (3×15 mL). The organic layers are combined, washed with saturated sodium bicarbonate solution, dried over MgSO$_4$, filtered and concentrated. The crude residue is purified by Combiflash (20 g silica gel column; eluents: DCM/MeOH, gradient 0% to 3%) to afford compound 1034.

Step 4: In a capped vial is prepared a solution of 1034 (40 mg, 0.070 mmol) in Et$_3$N (0.1 mL) and morpholine (36 µL, 0.417 mmol, 6.0 eq). The reaction mixture is stirred at 150° C. for 14 h. DMSO and MeOH are added. The mixture is filtered through Acrodisc filter and purified by semipreparative HPLC (MeOH/water, ammonium formate buffer pH 3.8). The pure fractions are combined and lyophilized to give compound 1056.

Step 5: To a solution of 31 b (50 mg, 0.092 mmol) in water (1.5 mL)/dichloromethane (1.5 mL) is added silica gel (500 mg). Pyridium tribromide (31 mg, 0.097 mmol, 1.1 eq) is added and the mixture is stirred at RT for 40 h. The reaction mixture is filtered through a fritted funnel and rinsed with DCM. More water is added and the mixture is extracted with DCM (3×5 mL). The organic layers are combined, dried over MgSO$_4$, filtered and concentrated. MeOH/DMSO is added. The mixture is filtered through Acrodisc and purified by semipreparative HPLC (MeOH/water, ammonium formate buffer pH 3.8). The pure fractions are combined and lyophilized to give compound 1040.

Example 32

Preparation of Intermediate 32a and 32c

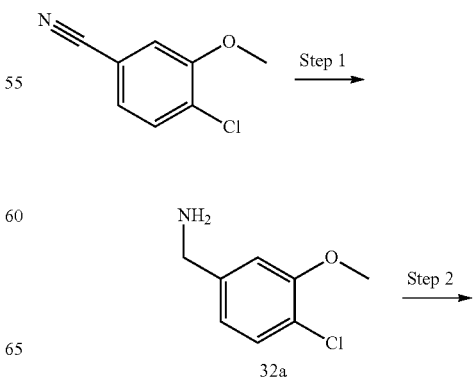

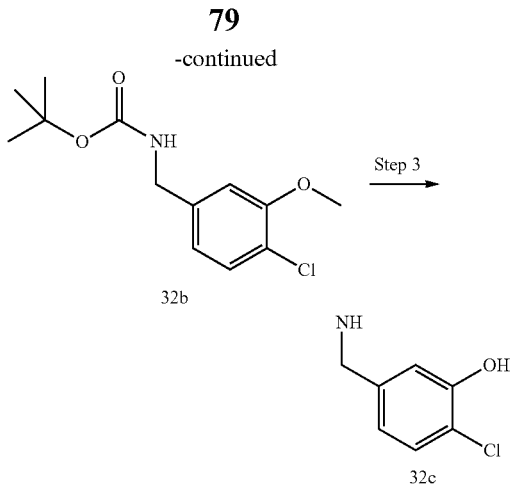

Step 1: A solution of 4-chloro-3-methoxybenzonitrile (Accelachem) (1.03 g, 6.15 mmol) in THF (25 mL) is cooled to 0° C. and a commercial solution of borane-dimethyl sulfide complex (10 M, 2.46 mL, 24.6 mmol, 4.0 eq) is added over 10 min. The reaction is refluxed for 1 h, then MeOH (5 mL) is added and all volatiles are removed under reduced pressure. The solid residue is triturated in EtOAc and collected by Buchner filtration to afford benzylamine 32a.

Step 2: To a solution of benzylamine 32a (1.05 g, 6.15 mmol) in THF (30 mL) is added triethylamine (2.63 mL, 18.9 mmol, 3.0 eq) followed by di-tert-butyl-dicarbonate (2.06 g, 9.44 mmol, 1.5 eq). The reaction is stirred overnight at RT. EtOAc (30 mL) and water are added and the phases are separated. The organic layer is washed with brine (2×20 mL), dried over $MgSO_4$, filtered and concentrated. The residue is purified by Combiflash (40 g column, Hex/EtOAc 10% to 50%) and the pure fractions are combined. After being concentrated, intermediate 32b is obtained.

Step 3: A solution of 32b (150 mg, 0.552 mmol) in DCM (6 mL) is cooled at 0° C. and a solution of $BBr_3$ in DCM (1 M, 1.1 mL, 1.10 mmol, 2.0 eq) is added. The mixture is stirred at 0° C. for 45 min, then HCl 1N solution (0.25 mL) is added followed by water (3 mL). The mixture is extracted with DCM (3×5 mL). The organic layers are dried by passing through a phase separator cartridge, and concentrated to afford crude intermediate 32c which is directly used for next step.

Example 33

Expression Vector, Protein Expression and Purification

The codon optimized UL54 HCMV polymerase gene for expression in insect cells is obtained from DNA 2.0 (Menlo Park, Calif.) and subcloned in 3' of the Glutathione-S-transferase (GST) gene in a pFastBac-derived vector. Bacmids and baculoviruses are generated and expression performed in Sf21 insect cells cultured in SF900 II SFM media. Infection using the baculoviruses is performed using an MOI of 5-10 and the cells are harvested 48 h post-infection and frozen.

Reagents and Materials (equivalents are acceptable):

| Product | Company | Catalog # | Storage |
|---|---|---|---|
| SF900 II SFM media | Invitrogen | 10902104 | 4° C. |
| Tris | Sigma | T1503 | RT |
| TCEP | Thermo Fisher Scientific | 77720 | 4° C. |
| EDTA | Ambion | AM9262 | RT |
| NaCl | Sigma | S6191 | RT |
| Glycerol | Thermo Fisher Scientific | BP229-4 | RT |
| PMSF | VWR | PB0425 | RT |
| Leupeptin | Cedarlane | N-1000.0025 | −20° C. |
| Antipain | MP Biomedicals | 152843 | −20° C. |
| Pepstatin A | MP Biomedicals | 195368 | −20° C. |
| Glutathione | Thermo Fisher Scientific | BP229-4 | RT |
| Glutathione Sepharose 4B | GE Healthcare | 17-0756-05 | 4° C. |
| HiTrap DEAE-Sepharose FF dolumn | GE Healthcare | 17-5055-01 | 4° C. |

All purification procedures are performed at 4° C. The cell pellet from 1 L of culture (1×10$^9$ cells) is resuspended in 25 mL of 50 mM Tris pH 7.5, 1 mM TCEP, 0.1 mM EDTA, 150 mM NaCl, 10% Glycerol, 1 mM PMSF, 2 μg/mL Leupeptin, 2 μg/mL Antipain, 2 μg/mL Pepstatin A. The solution is homogenized using a Dounce tissue grinder. Following homogenization, the volume is increased to 40 mL followed by centrifugation at 750×g for 5 min to remove nuclei. The supernatant is then transferred and 3 cc of 50% slurry of glutathione-sepharose 4B resin is added. The mixture is incubated on a rotator for 1 h. The slurry is centrifuged at 500 g for 5 min. The supernatant is discarded and the pellet is resuspended in 10× volume of wash buffer (50 mM Tris pH 7.5, 1 mM TCEP, 0.1 mM EDTA, 150 mM NaCl, 10% Glycerol) and incubated for 5 min. The slurry is centrifuged at 500 g for 5 min and the supernatant is discarded. The wash step is performed 5 times. The elution is performed by adding 1.5 volume of elution buffer (50 mM Tris pH 7.5, 1 mM TCEP, 0.1 mM EDTA, 150 mM NaCl, 10% Glycerol, 20 mM glutathione) and incubating on a rotator for 15 min. The slurry is centrifuged at 500 g for 5 min and the supernatant is removed and kept. The elution step is performed four times. The supernatants are pooled and centrifuged at 500×g for 5 min to remove resin particles and frozen at −80° C.

The frozen protein is thawed and the NaCl concentration reduced to 37.5 mM by the addition of 3 volumes of DEAE buffer A (50 mM Tris pH 7.5, 1 mM TCEP, 0.1 mM EDTA, 10% Glycerol). The protein is loaded on a HiTrap DEAE-Sepharose μF column and eluted using a gradient with DEAE buffer B (50 mM Tris pH 7.5, 1 mM TCEP, 0.1 mM EDTA, 10% Glycerol, 1 M NaCl). UL54 eluted at 140 mM NaCl. The DEAE fractions are pooled, frozen and stored at −80° C. The protein concentration is determined by $OD_{280}$ ($A_{280}$=1.03 mg/mL).

Example 34

HCMV Polymerase LANCE TR-FRET Assay

This non-radiometric assay determines the enzymatic activity of purified recombinant HCMV polymerase (UL54) using a Digoxigenin-labeled oligonucleotide priming a heteropolymeric template. The enzymatic activity is determined by incorporating Biotin-dUTP in the nascent complementary strand. The signal is generated by Fluorescence Resonance Energy Transfer from the donor (Anti-Digoxigenin-Europium Chelate binding with the primer) to the acceptor Streptavidin-AlloPhycoCyanin (SA-APC) binding to the biotin of the labeled nucleotides incorporated in proximity.

Reagents and Materials (equivalents are acceptable):

| Product | Company | Catalog # | Storage |
|---|---|---|---|
| 384-well white PP | SeaHorse | S30033W | RT |
| 1M Hepes | Invitrogen | 15630-080 | 4° C. |
| 10 mg/mL BSA | New England Biolabs | B9001S | −20° C. |
| 0.5M TCEP pH 7.0 | Thermo Fisher Scientific | 77720 | 4° C. |
| 0.5M EDTA pH 8.0 | Ambion | AM9262 | RT |
| DMSO | VWR (EMD Chemicals) | CAMX1457-6 | RT |
| KCl | Sigma | P9541 | RT |
| NaCl | Sigma | S6191 | RT |
| $MgCl_2$ | VWR (EMD Chemicals) | CAMX0045-1 | RT |
| Glycerol | Thermo Fisher Scientific | BP229-4 | RT |
| Tris | Sigma | T1503 | RT |
| 10% Tween-20 | Bio-Rad | 161-0781 | RT |
| Heteropolymeric template | Integrated DNA Technologies | Custom | −20° C. |
| Digoxigenin-labeled primer | Integrated DNA Technologies | Custom | −20° C. |
| 100 mM Deoxynucleotide Solution | New England Biolabs | N0446S | −20° C. |
| 1 mM Biotin-16-dUTP | Roche | 11093070910 | −20° C. |
| Streptavidin-APC | PerkinElmer | CR130-100 | 4° C. |
| Anti-Dig-Europium | PerkinElmer | Custom | 4° C. |
| GST-UL54 | Purified as described in Example 33 | | −80° C. |

Preparation of Compounds:

Serial dilutions of the DMSO stock compound solution are performed using DMSO in columns 2-11 and 14-23. DMSO alone is present in columns 1, 12, 13 and 24. The plate is centrifuged at 200×g for 30 sec. 35 µL of compound dilution buffer (10 mM Hepes pH 7.5, 25 mM KCl, 5 mM $MgCl_2$, 1 mM TCEP) is added to 5 µL of the diluted compound in DMSO to obtain 12.5% DMSO. 4 µL per well of the 12.5% DMSO serial dilution compound solution is added to the assay plate.

LANCE TR-FRET Assay:

The assay conditions are the following: 10 mM HEPES pH 7.5, 25 mM KCl, 7.5 mM NaCl, 5 mM $MgCl_2$, 0.2 mg BSA/mL, 1 mM TCEP, 1.5% glycerol, 5% DMSO, 235 nM dATP, 350 nM dCTP, 350 nM dGTP, 235 nM dTTP, 12 nM biotin-16-dUTP, 23.5 nM Dig-primer/template, 2 nM GST-UL54. The assay volume is 10 µL. Each reagent is added as follow: 4 µL a+3 µL b+3 µL c; a: compound diluted in compound dilution buffer to obtain 12.5% DMSO; b: enzyme (GST-UL54) in 10 mM Hepes pH 7.5, 25 mM KCl, 5 mM $MgCl_2$, 25 mM NaCl, 5% Glycerol, 0.67 mg BSA/mL, 1 mM TCEP w/o DMSO (2 nM GST-UL54 is present in the assay); c: substrate in 10 mM HEPES pH 7.5, 25 mM KCl, 5 mM $MgCl_2$, 1 mM TCEP, 783 nM dATP, 1166 nM dCTP, 1166 nM dGTP, 783 nM dTTP, 40 nM biotin-16-dUTP, 78 nM Dig-primer (5'-/Dig/AGC TCG TTT AGT GAA CC-3') (SEQ ID NO: 1)/template (5'-GAG GTC AAA ACA GCG TGG ATG GCG TCT CCA GGC GAT CTG ACG GTT CAC TAA ACG AGC T-3') (SEQ ID NO: 2) w/o DMSO. The primer and template are annealed in 10 mM Tris-HCl pH 7.5, 50 mM NaCl at a respective concentration of 50 µM. They are incubated at 95° C. for 5 min in a dry batch block. The block is removed from the dry bath and allowed to cool to RT. Aliquots are made and stored at −20° C.

To perform the assay, 3 µL of the enzyme solution is added to columns 2-12 and 14-24. The enzyme is substituted by the blank solution (b solution without enzyme) for columns 1 and 13 (blanks). 3 µL of substrate solution is added to each well. Plates are incubated at 37° C. for 30 min. 5 µL of conjugate solution is added (25 mM Hepes pH 7.5, 0.1 M NaCl, 0.25% Tween-20, 1 mg/mL BSA, 12 mM EDTA, 24 nM Sreptavidin-APC, 342 ng/mL Anti-Dig-Europium). Plates are incubated at RT for at least 120 min. The signal is read on the Envision plate reader (Perkin-Elmer) or equivalent.

All compounds of the invention are tested in the assay described in Example 34. Compounds tested in the assay of Example 34 showed $IC_{50}$ value in the range of 2 µM or less. Representative data is shown in the table below:

Example 34

| Cmpd # | Example 34 $IC_{50}$ (nM) |
|---|---|
| 1002 | 38 |
| 1004 | 26 |
| 1007 | 48 |
| 1016 | 74 |
| 1024 | 29 |
| 1031 | 58 |
| 1038 | 78 |
| 1056 | 110 |
| 1061 | 60 |
| 1065 | 35 |
| 1070 | 61 |
| 1072 | 260 |
| 1073 | 42 |
| 1074 | 75 |
| 2017 | 210 |
| 3001 | 140 |
| 4003 | 93 |
| 5002 | 69 |
| 5004 | 77 |
| 5006 | 89 |
| 5007 | 65 |
| 5012 | 160 |
| 5015 | 200 |
| 5021 | 330 |
| 5022 | 460 |
| 5035 | 240 |
| 5037 | 440 |
| 5038 | 140 |
| 5046 | 190 |
| 5048 | 170 |

Tables of Compounds

The following tables list compounds representative of the invention. All of the compounds in Tables 1 to 5 are synthesized analogously to the Examples described above. For each compound in the tables, the analogous synthetic route to prepare each compound is identified by Example number. It will be apparent to a skilled person that the analogous synthetic routes may be used, with appropriate modifications, to prepare the compounds of the invention as described herein.

Retention times ($t_R$) for each compound are measured using the standard analytical HPLC or UPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC or UPLC instruments. Even when measured on the same instrument, the values may vary when measured, for example, using different individual HPLC or UPLC columns, or, when measured on the same instrument and the same individual column, the values may vary, for example, between individual measurements taken on different occasions.

TABLE 1
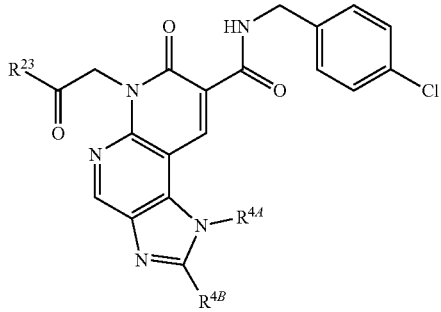
| Cmpd # | R4A | R4B | R23 | $t_R$ (min) | (M + H)+ | Ex. # |
|---|---|---|---|---|---|---|
| 1001 | —CH3 | —CH3 |  | 1.69 | 521.2 523.1 | 27 |
| 1002 | —CH3 | —CH3 |  | 1.77 | 511.3 513.4 | 19 |
| 1003 | —CH3 | N(CH3)S(O)2CH3 | 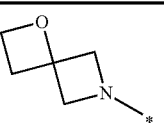 | 5.55 | 604.2 | 31 |
| 1004 | —CH2CH3 | H |  | 1.79 | 511 513 | 22 |
| 1005 | —CH2CH3 | —CH2CH3 |  | 1.88 | 539 541 | 22 |
| 1006 | —CH3 | cyclobutyl | 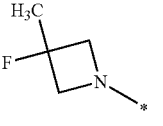 | 2.01 | 551.3 | 25 |
| 1007 | —CH3 | —CH3 |  | 1.75 | 529.2 531.1 | 27 |
| 1008 | —CH3 | —CH3 | 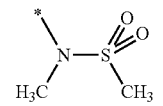 | 1.85 | 505 507 | 27 |
| 1009 | —CH2CH3 | —CH3 | 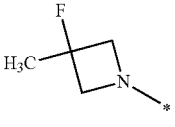 | 1.82 | 525 527 | 21 |

TABLE 1-continued

| Cmpd # | R<sup>4A</sup> | R<sup>4B</sup> | R<sup>23</sup> | t<sub>R</sub> (min) | (M + H)<sup>+</sup> | Ex. # |
|---|---|---|---|---|---|---|
| 1010 | —CH₃ | —CF₃ | 3-fluoro-3-methylazetidin-1-yl (via C=O-CH₂) | 1.46 | 564.9, 566.9 | 26 |
| 1011 | —CH₃ | —CH₃ (ethyl, *CH₂CH₃) | 3-(1H-pyrazol-1-yl)azetidin-1-yl | 1.05 | 545, 547 | 27 |
| 1012 | —CH₃ | H | 3-fluoro-3-methylazetidin-1-yl | 1.74 | 497, 499 | 19 |
| 1013 | —CH₃ | —CH₂NHCH₃ | 3-fluoro-3-methylazetidin-1-yl | 1.03 | 540.0, 542.0 | 24 |
| 1014 | —CH₃ | —CH₂CH₃ | N-methyl-N-cyclohexylamino | 2.12 | 535.2, 537.2 | 27 |
| 1015 | —CH₃ | —CH₂CH₃ | 3-(fluoromethyl)azetidin-1-yl | 1.73 | 511.2, 513.1 | 27 |
| 1016 | —CH₃ | 1-methyl-1H-pyrazol-4-yl | 3-fluoro-3-methylazetidin-1-yl | 1.81 | 577.4, 579.4 | 26 |
| 1017 | —CH₃ | —CH₂CH₃ | 2-(hydroxymethyl)azetidin-1-yl | 1.65 | 509.2, 511.1 | 27 |

TABLE 1-continued
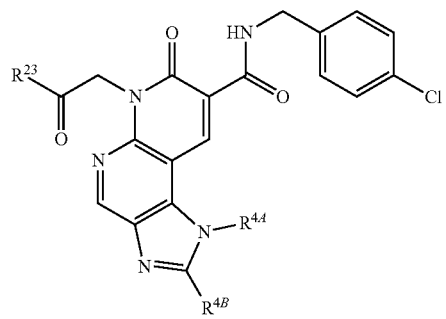
| Cmpd # | R[4A] | R[4B] | R[23] | t[R] (min) | (M + H)+ | Ex. # |
|---|---|---|---|---|---|---|
| 1018 | CH₃ | tetrahydrofuran-2-yl | 3-fluoro-3-methylazetidin-1-yl | 1.85 | 567.4, 569.4 | 26 |
| 1019 | CH₃ | CH₃ | methyl 3-methylazetidine-3-carboxylate | 1.8 | 551, 553 | 27 |
| 1020 | CH₃ | CH₃ | 3-cyanopyrrolidin-1-yl | 1.64 | 518, 520 | 27 |
| 1021 | CH₃ | 2-(dimethylamino)pyrimidin-5-yl | 3-fluoro-3-methylazetidin-1-yl | 1.9 | 618.4, 620.4 | 26 |
| 1022 | CH₃ | ethyl acetate | 3-fluoro-3-methylazetidin-1-yl | 1.81 | 584, 586 | 19 |
| 1023 | CH₃ | CH₃ | 2-(azetidin-3-yl)-2-methylpropanenitrile | 1.78 | 546, 548 | 27 |
| 1024 | CH₂CH₂OH | H | 3-fluoro-3-methylazetidin-1-yl | 1.72 | 527, 529 | 21 |

TABLE 1-continued

| Cmpd # | R⁴ᴬ | R⁴ᴮ | R²³ | $t_R$ (min) | (M + H)⁺ | Ex. # |
|---|---|---|---|---|---|---|
| 1025 | H | H | 3-fluoro-3-methylazetidinyl | 1.72 | 483.3 (M − H) | 13 |
| 1026 | CH₃ | 2-methyl-1H-imidazol-4-yl | 3-fluoro-3-methylazetidinyl | 1.82 | 577.4 579.4 | 26 |
| 1027 | CH₃ | N-methylaminomethyl | 3-fluoro-3-methylazetidinyl | 4.44 | 526.2 | 31 |
| 1028 | CH₃ | morpholinomethyl | 3-fluoro-3-methylazetidinyl | 0.92 | 596.2 598.2 | 24 |
| 1029 | CH₃ | azetidin-1-ylmethyl | 3-fluoro-3-methylazetidinyl | 0.79 | 566.2 568.2 | 24 |
| 1030 | CH₃ | (3,3-difluoroazetidin-1-yl)methyl | 3-fluoro-3-methylazetidinyl | 1.2 | 602.2 604.1 | 24 |
| 1031 | CH₃ | methoxymethyl | 3-fluoro-3-methylazetidinyl | 1.23 | 541 543 | 24 |

TABLE 1-continued

| Cmpd # | R^4A | R^4B | R^23 | t_R (min) | (M + H)+ | Ex. # |
|---|---|---|---|---|---|---|
| 1032 | CH3 | cyclopropylmethyl | 3-fluoro-3-methylazetidinyl | 1.26 | 551.0 553.0 | 25 |
| 1033 | CH3 | CH2S(O)2CH3 | 3-fluoro-3-methylazetidinyl | 1.28 | 589.2 591.2 | 24 |
| 1034 | CH3 | S(O)2CH3 | 3-fluoro-3-methylazetidinyl | 5.55 | 575.2 | 31 |
| 1035 | CH3 | tetrahydropyran-4-yl | 3-fluoro-3-methylazetidinyl | 1.16 | 581.3 583.3 | 25 |
| 1036 | CH3 | CH2CH2S(O)CH3 | 3-fluoro-3-methylazetidinyl | 1.18 | 587.2 589.2 | 25 |
| 1037 | CH3 | CH2CH2S(O)2CH3 | 3-fluoro-3-methylazetidinyl | 1.27 | 603.2 605.2 | 25 |
| 1038 | CH3 | 2-oxopyrrolidin-1-yl | 3-fluoro-3-methylazetidinyl | 5.29 | 580.2 | 31 |

TABLE 1-continued
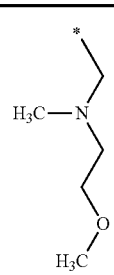
| Cmpd # | R⁴ᴬ | R⁴ᴮ | R²³ | $t_R$ (min) | (M + H)⁺ | Ex. # |
|---|---|---|---|---|---|---|
| 1039 | —CH₃ | *-CH₂-N(CH₃)-CH₂CH₂-O-CH₃ | 3-fluoro-3-methylazetidinyl | 0.81 | 598.1 600.0 | 24 |
| 1040 | —CH₃ | *-S(=O)-CH₃ | 3-fluoro-3-methylazetidinyl | 5.01 | 559.2 | 31 |
| 1041 | —CH₃ | *-CH₂-CN | 3-fluoro-3-methylazetidinyl | 1.22 | 536.0 538.0 | 25 |
| 1042 | —CH₃ | *-CH₂CH₂-C(=O)OH | 3-fluoro-3-methylazetidinyl | 1.09 | 569.2 571.2 | 25 |
| 1043 | —CH₃ | *-C(CH₃)₂-CH₂OH | 3-fluoro-3-methylazetidinyl | 1.17 | 569.2 571.2 | 25 |
| 1044 | —CH₃ | *-O-CH₃ | 3-fluoro-3-methylazetidinyl | 1.95 | 527.1 | 19 |
| 1045 | —CH₃ | *-N(CH₃)₂ | 3-fluoro-3-methylazetidinyl | 1.94 | 540.2 | 18 |

TABLE 1-continued

| Cmpd # | R$^{4A}$ | R$^{4B}$ | R$^{23}$ | t$_R$ (min) | (M + H)$^+$ | Ex. # |
|---|---|---|---|---|---|---|
| 1046 | CH$_3$ | *-CH$_2$-N(CH$_3$)-CH$_2$CH$_2$F | 3-fluoro-3-methylazetidinyl | 0.89 | 586.2, 588.2 | 24 |
| 1047 | CH$_3$ | *-CH$_2$-N(CH$_3$)-CH$_2$CN | 3-fluoro-3-methylazetidinyl | 1.18 | 579.2, 581.2 | 24 |
| 1048 | CH$_3$ | *-O-CH$_2$CH$_3$ | 3-fluoro-3-methylazetidinyl | 2.00 | 541.1 | 19 |
| 1049 | CH$_3$ | 1-methylpyrrolidin-2-yl | 3-fluoro-3-methylazetidinyl | 1.07 | 580.0, 582.0 | 25 |
| 1050 | CH$_3$ | pyrrolidin-1-yl | 3-fluoro-3-methylazetidinyl | 4.6 | 566.3 | 31 |
| 1051 | CH$_3$ | *-NH-CH$_2$CH$_2$-NH-C(O)CH$_3$ | 3-fluoro-3-methylazetidinyl | 4.44 | 597.3 | 31 |
| 1052 | CH$_3$ | *-NH-S(O)$_2$-N(CH$_3$)$_2$ | 3-fluoro-3-methylazetidinyl | 5.49 | 619.2 | 31 |

TABLE 1-continued

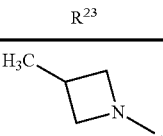

| Cmpd # | R<sup>4A</sup> | R<sup>4B</sup> | R<sup>23</sup> | t<sub>R</sub> (min) | (M + H)<sup>+</sup> | Ex. # |
|---|---|---|---|---|---|---|
| 1053 | —CH₃ | —CH₃ | 3-methylazetidinyl | 1.79 | 493<br>495 | 27 |
| 1054 | —CH₃ | 4-methylpiperazin-1-yl | 3-fluoro-3-methylazetidinyl | 4.49 | 595.3 | 31 |
| 1055 | —CH₃ | cyclobutyl | 3-methylazetidinyl | 1.29 | 533.2<br>535.2 | 25-26 |
| 1056 | —CH₃ | morpholin-4-yl | 3-fluoro-3-methylazetidinyl | 5.1 | 582.2 | 31 |
| 1057 | —CH₃ | tetrahydrofuran-3-yl | 3,3-dimethylazetidinyl | 1.23 | 563.2<br>565.3 | 25-26 |
| 1058 | —CH₃ | azetidin-1-yl | 3-fluoro-3-methylazetidinyl | 4.57 | 552.2 | 31 |
| 1059 | —CH₃ | NHS(O)₂CH₃ | 3-fluoro-3-methylazetidinyl | 5.12 | 590.2 | 31 |
| 1060 | —CH₃ | —OCH₂C(CH₃)₂COOH | 3-fluoro-3-methylazetidinyl | 5.63 | 613.3 | 31 |

TABLE 1-continued

| Cmpd # | R^4A | R^4B | R^23 | t_R (min) | (M + H)^+ | Ex. # |
|---|---|---|---|---|---|---|
| 1061 | CH₃ | 1H-imidazol-1-yl | 3-fluoro-3-methylazetidin-1-yl | 4.56 | 563.2 | 31 |
| 1062 | CH₃ | CH₃ | 3-hydroxy-3-methylazetidin-1-yl | 1.66 | 509, 511 | 27 |
| 1063 | CH₃ | CH₃ | 3-fluoroazetidin-1-yl | 1.78 | 497, 499 | 27 |
| 1064 | CH₃ | CH₃ | 3,3-difluoroazetidin-1-yl | 1.83 | 515, 517 | 27 |
| 1065 | CH₃ | CH₃ | 3-fluoro-3-(hydroxymethyl)azetidin-1-yl | 1.7 | 527, 529 | 27 |
| 1066 | CH₃ | CH₃ | 3-methoxyazetidin-1-yl | 1.8 | 509, 511 | 27 |
| 1067 | CH₃ | CH₃ | 3-cyanoazetidin-1-yl | 1.67 | 504, 506 | 27 |
| 1068 | CH₃ | CH₃ | 3-(methylsulfonyl)azetidin-1-yl | 1.64 | 557, 559 | 27 |
| 1069 | CH₃ | CH₃ | 3-cyano-3-methylazetidin-1-yl | 1.74 | 518, 520 | 27 |

TABLE 1-continued

| Cmpd # | R^4A | R^4B | R^23 | t_R (min) | (M + H)^+ | Ex. # |
|---|---|---|---|---|---|---|
| 1070 | —CH$_3$ | —CH$_2$N(CH$_3$)$_2$ | 3,3-dimethylazetidin-1-yl | 1.1 | 550.1, 552.1 | 24 |
| 1071 | —CH$_3$ | —CH$_3$ | 2,6-diazaspiro[3.3]heptan-2-yl | 1.43 | 520, 522 | 27 |
| 1072 | —CH$_3$ | —CH$_3$ | 6,6-difluoro-2,6-diazaspiro[3.3]heptan-2-yl | 1.78 | 556, 558 | 27 |
| 1073 | —CH$_3$ | —CH$_3$ | HOCH$_2$C(CH$_3$)$_2$CH$_2$N(CH$_3$)— | 1.91 | 539, 541 | 27 |
| 1074 | —CH$_3$ | —OCH$_3$ | 3-cyano-3-methylazetidin-1-yl | 5.35 | 534.2 | 19 |
| 1075 | —CH$_3$ | —OCH$_3$ | 3,3-dimethylazetidin-1-yl | 5.84 | 523.3 | 19 |

TABLE 2
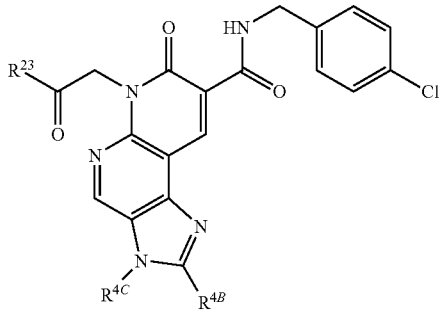
| Cmpd # | R[23] | R[4C] | R[4B] | t_R (min) | (M + H)+ | Ex. # |
|---|---|---|---|---|---|---|
| 2001 | 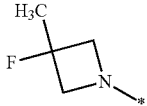 | *—CH₃ | *—CH₃ | 1.74 | 511.3 | 13 |
| 2002 | 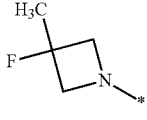 | *—CH₃ | H | 1.81 | 497.3 | 14 |
| 2003 |  | *—CH₃ | *—CH₂CH₃ | 1.88 | 525.3 | 14 |
| 2004 | 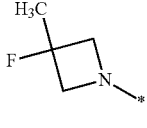 | *—CH₃ | *-cyclopropyl | 1.92 | 537.3 | 15 |
| 2005 | 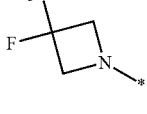 | *—CH₂CH₃ | H | 1.85 | 511.4 | 14 |
| 2006 |  | *—CH₂-cyclopropyl | H | 1.92 | 537.4 | 14 |
| 2007 |  | *—CH₃ | *—CH(CH₃)₂ | 5.14 | 539.3 | 15 |
| 2008 |  | *—CH₂CH₃ | *—CH₃ | 4.96 | 525.3 | 13 |
| 2009 |  | H | *—CH₂CH₃ | 1.95 | 511.3 | 13 |

TABLE 2-continued
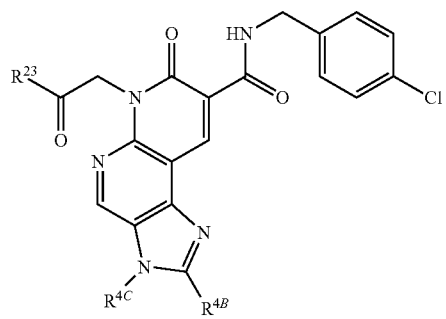
| Cmpd # | R²³ | R⁴ᶜ | R⁴ᴮ | $t_R$ (min) | (M + H)⁺ | Ex. # |
|---|---|---|---|---|---|---|
| 2010 | H₃C-[3-F-azetidinyl] | H | *—CH₃ | 1.89 | 497.3 | 13 |
| 2011 | H₃C-[3-F-azetidinyl] | (CH₃)₂CH—* | H | 1.89 | 525.4 | 14 |
| 2012 | H₃C-[3-F-azetidinyl] | H₃C—O—CH₂—* | H | 1.85 | 527.3 | 14 |
| 2013 | H₃C-[3-F-azetidinyl] | H₃C—O—CH₂CH₂—* | H | 1.85 | 541.4 | 14 |
| 2014 | H₃C-[3-F-azetidinyl] | H₃C-CH(OH)-CH₂—* | H | 1.79 | 541.4 | 14 |
| 2015 | H₃C-[3-F-azetidinyl] | HO-CH₂CH₂—* | *—CH₃ | 1.78 | 541.4 | 13 |
| 2016 | H₃C-[3-F-azetidinyl] | N≡C-CH₂—* | H | 1.81 | 522.3 | 14 |
| 2017 | H₃C-[3-F-azetidinyl] | *—CH₃ | (CH₃)₂N—* | 1.91 | 540.2 | 18 |
| 2018 | H₃C-[3-F-azetidinyl] | *—CH₃ | cyclobutyl-* | 5.25 | 551.1 | 15 |

TABLE 2-continued

[Structure diagram showing core scaffold with R23, R4C, R4B substituents and 4-chlorobenzyl amide]

| Cmpd # | R23 | R4C | R4B | t_R (min) | (M + H)+ | Ex. # |
|---|---|---|---|---|---|---|
| 2019 | H3C-azetidinyl (3-methyl) | *—CH3 | *—CH3 | 4.71 | 493.3 | 29 |
| 2020 | H3C, H3C-azetidinyl (3,3-dimethyl) | *—CH3 | *—CH3 | 4.99 | 507.3 | 29 |
| 2021 | H3C, H3C-azetidinyl (3,3-dimethyl) | *—CH3 | *-cyclopropyl | 5.37 | 533.3 | 15 |
| 2022 | H3C, H3C-azetidinyl (3,3-dimethyl) | H3C-CH2—* | *—CH3 | 5.19 | 521.3 | 29 |
| 2023 | H3C-azetidinyl (3-methyl) | *—CH3 | *-cyclopropyl | 5.07 | 519.3 | 15 |
| 2024 | H3C-azetidinyl (3-methyl) | H3C-CH2—* | *—CH3 | 4.9 | 507.3 | 29 |
| 2025 | H3C, H3C-azetidinyl (3,3-dimethyl) | H | *—CH3 | 4.89 | 493.3 | 14 |

TABLE 3

[Structure: R23-C(=O)-CH2-N of pyridone fused to imidazole with N-CH3 and R4B substituent; pyridone bears C(=O)NH-CH2-(4-cyanophenyl)]

| Cmpd # | R23 | R4B | tR (min) | (M + H)+ | Ex. # |
|---|---|---|---|---|---|
| 3001 | 3-methyl-3-fluoroazetidin-1-yl (H3C, F on azetidine) | *-CH3 | 1.51 | 502.4 | 28 |
| 3002 | 3,3-dimethylazetidin-1-yl | *-cyclopropyl | 1.73 | 524.2 | 26-27 |
| 3003 | 3-methyl-3-fluoroazetidin-1-yl | *-cyclopropyl | 1.62 | 528.2 | 26-27 |
| 3004 | 3-methyl-3-fluoroazetidin-1-yl | *-CH2CH3 | 158 | 516.2, 514.3 | 30 |
| 3005 | 3,3-dimethylazetidin-1-yl | *-CH2CH3 | 1.69 | 512.2 | 30 |
| 3006 | 3-methyl-3-fluoroazetidin-1-yl | *-CH(OCH3) (methoxymethyl) | 4.86 | 518.3 | 19 |

TABLE 4

[Structure: analogous scaffold with R4C and CH3 on imidazole ring]

| Cmpd # | R23 | R4C | tR (min) | (M + H)+ | Ex. # |
|---|---|---|---|---|---|
| 4001 | 3,3-dimethylazetidin-1-yl | *-CH3 | 4.37 | 498.3 | 13 |
| 4002 | 3-methyl-3-fluoroazetidin-1-yl | *-CH3 | 4.12 | 502.3 | 13 |
| 4003 | 3-methylazetidin-1-yl | *-CH3 | 4.06 | 484.3 | 13 |
| 4004 | 3,3-dimethylazetidin-1-yl | H3C-CH(*)- (ethyl branched) | 4.56 | 512.3 | 13 |
| 4005 | 3-methylazetidin-1-yl | H3C-CH(*)- | 4.07 | 498.3 | 13 |
| 4006 | 3-methyl-3-fluoroazetidin-1-yl | H3C-CH(*)- | 4.32 | 516.3 | 13 |

TABLE 5

| Cmpd # | Structure | tR (min) | (M + H)+ | Ex. # |
|---|---|---|---|---|
| 5001 | [Structure: 3-fluoro-3-methylazetidin-1-yl-C(=O)-CH2-N of pyridone fused to pyrrolo-imidazole; pyridone bears C(=O)NH-CH2-(4-chlorophenyl)] | 1.79 | 523, 525 | 23 |

TABLE 5-continued

| Cmpd # | Structure | t_R (min) | (M + H)+ | Ex. # |
|---|---|---|---|---|
| 5002 | 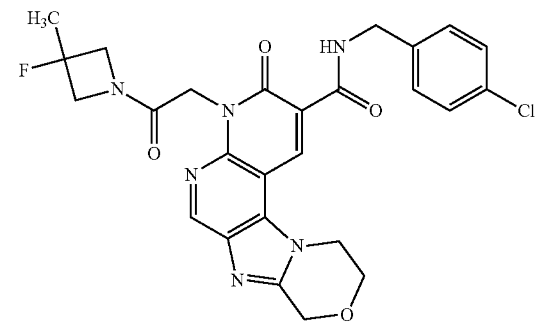 [SMILES: CC1(F)CN(C(=O)Cn2c(=O)c(C(=O)NCc3ccc(Cl)cc3)cc3c4c(cnc32)nc2n4CCOC2)C1] | 1.75 | 539 541 | 23 |
| 5003 | 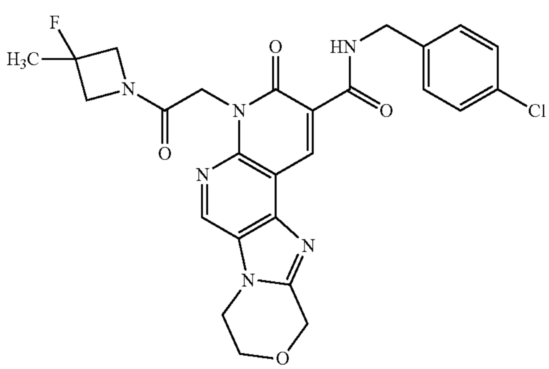 [SMILES: CC1(F)CN(C(=O)Cn2c(=O)c(C(=O)NCc3ccc(Cl)cc3)cc3c4nc5n(c4cnc32)CCOC5)C1] | 1.77 | 539 541 | 16 |
| 5004 | 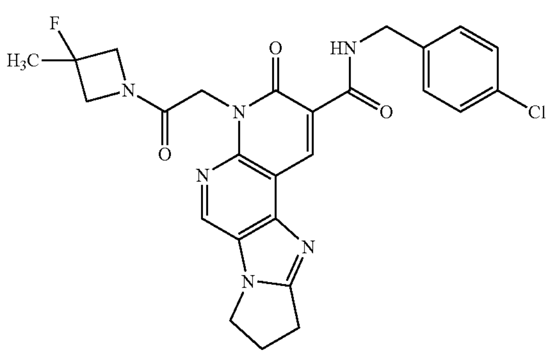 [SMILES: CC1(F)CN(C(=O)Cn2c(=O)c(C(=O)NCc3ccc(Cl)cc3)cc3c4nc5n(c4cnc32)CCC5)C1] | 1.78 | 523 525 | 16 |
| 5005 | 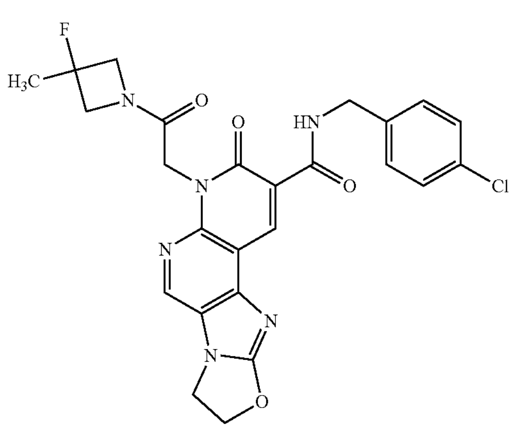 [SMILES: CC1(F)CN(C(=O)Cn2c(=O)c(C(=O)NCc3ccc(Cl)cc3)cc3c4nc5n(c4cnc32)CCO5)C1] | 5.29 | 525.2 | 17 |

TABLE 5-continued

| Cmpd # | Structure | $t_R$ (min) | (M + H)+ | Ex. # |
|---|---|---|---|---|
| 5006 | 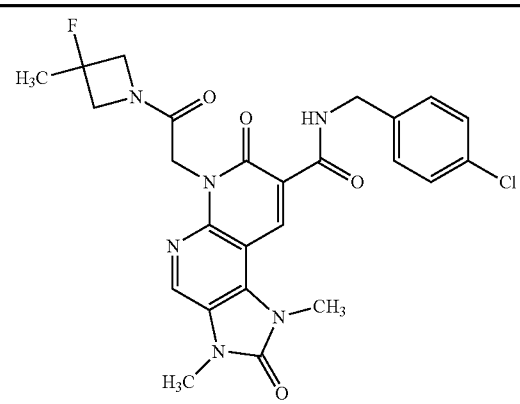 | 1.86 | 527.3 | 17 |
| 5007 | 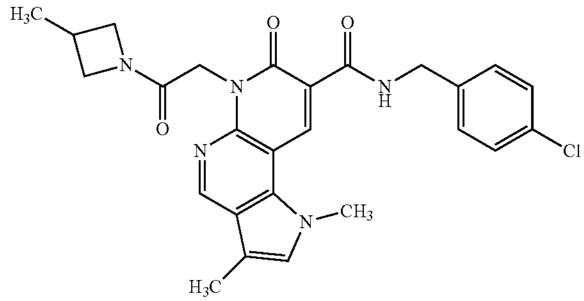 [SMILES: Cc1cn(C)c2c1cnc1c2cc(C(=O)NCc2ccc(Cl)cc2)c(=O)n1CC(=O)N1CC(C)C1] | 1.5 | 492.1 | 4 |
| 5008 | 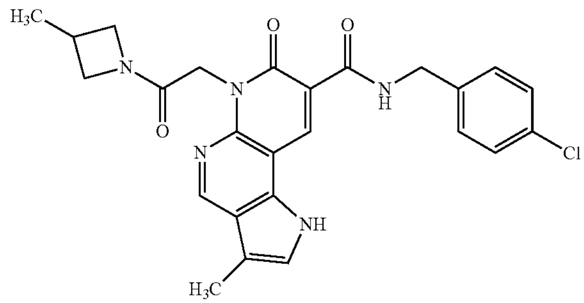 [SMILES: Cc1c[nH]c2c1cnc1c2cc(C(=O)NCc2ccc(Cl)cc2)c(=O)n1CC(=O)N1CC(C)C1] | 2.07 | 478.2 | 4 |
| 5009 | 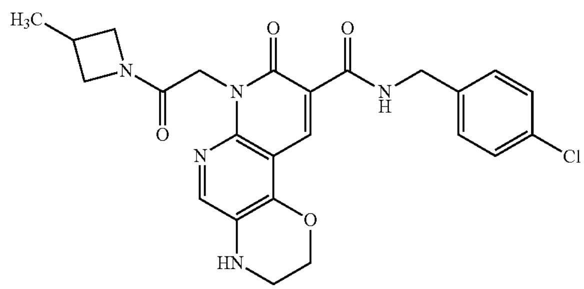 [SMILES: CC1CN(C(=O)Cn2c(=O)c(C(=O)NCc3ccc(Cl)cc3)cc3c4c(cnc32)NCCO4)C1] | 1.3 | 482.0<br>484.0 | 8 |
| 5010 | 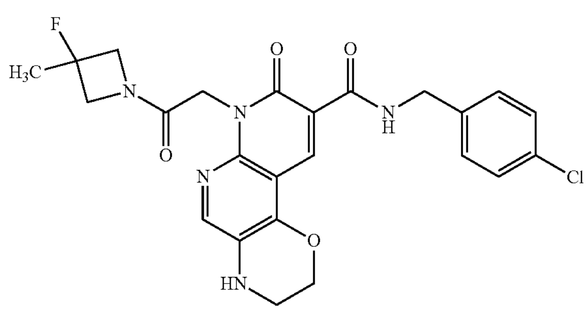 [SMILES: CC1(F)CN(C(=O)Cn2c(=O)c(C(=O)NCc3ccc(Cl)cc3)cc3c4c(cnc32)NCCO4)C1] | 1.3 | 500.1<br>501.9 | 7 |

TABLE 5-continued

| Cmpd # | Structure | $t_R$ (min) | (M + H)+ | Ex. # |
|---|---|---|---|---|
| 5011 | 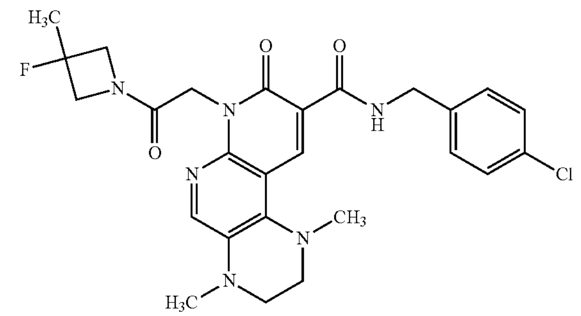 [SMILES: CN1CCN(C)c2c1cnc1c2cc(C(=O)NCc2ccc(Cl)cc2)c(=O)n1CC(=O)N1CC(C)(F)C1] | 1.89 | 527, 529 | 5 |
| 5012 | 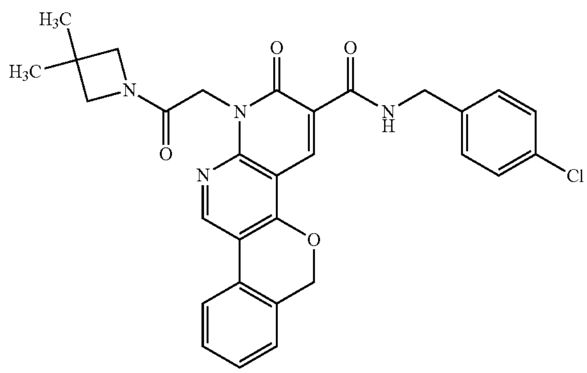 [SMILES: CC1(C)CN(C(=O)Cn2c(=O)c(C(=O)NCc3ccc(Cl)cc3)cc3c4c(cnc32)-c2ccccc2CO4)C1] | 1.7 | 543.1, 545.3 | 6 |
| 5013 | 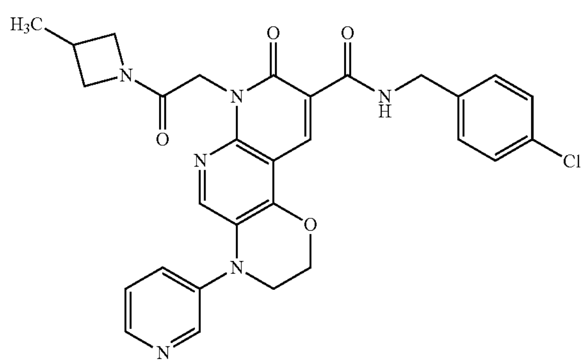 [SMILES: CC1CN(C(=O)Cn2c(=O)c(C(=O)NCc3ccc(Cl)cc3)cc3c4c(cnc32)N(c2cccnc2)CCO4)C1] | 1.1 | 559.1, 561.2 | 9 |
| 5014 | 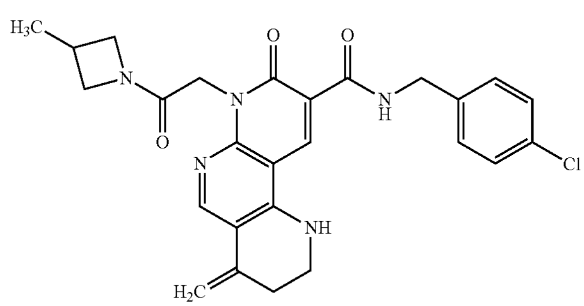 [SMILES: C=C1CCNc2c1cnc1c2cc(C(=O)NCc2ccc(Cl)cc2)c(=O)n1CC(=O)N1CC(C)C1] | 2.08 | 492.2 | 4 |

TABLE 5-continued

| Cmpd # | Structure | $t_R$ (min) | (M + H)+ | Ex. # |
|---|---|---|---|---|
| 5015 | 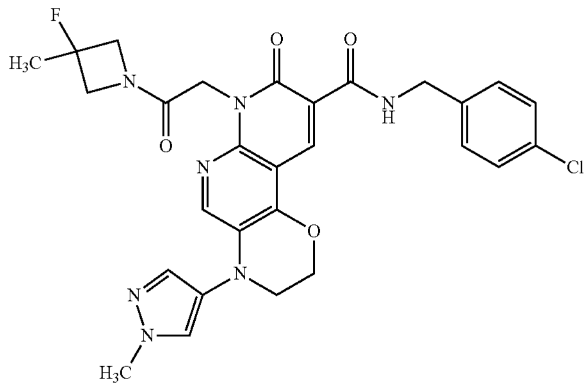 [SMILES: Cn1cc(N2CCOc3c2cnc2c3cc(C(=O)NCc3ccc(Cl)cc3)c(=O)n2CC(=O)N2CC(C)(F)C2)cn1] | 1.3 | 580.2 582.1 | 9 |
| 5016 | 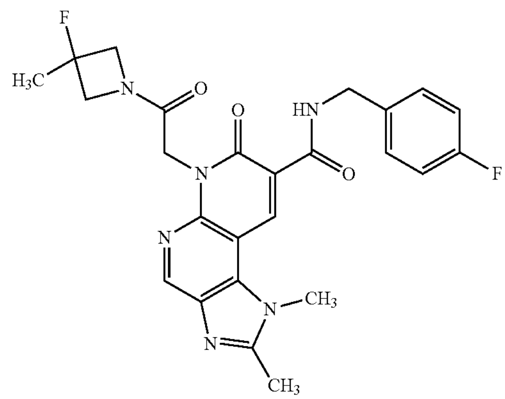 [SMILES: Cc1nc2cnc3c(cc(C(=O)NCc4ccc(F)cc4)c(=O)n3CC(=O)N3CC(C)(F)C3)c2n1C] | 1.69 | 495 | 28 |
| 5017 | 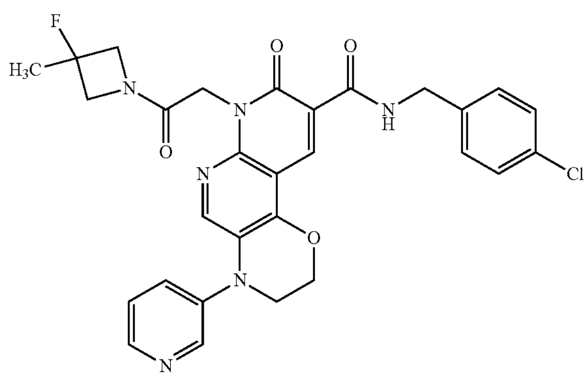 [SMILES: CC1(F)CN(C(=O)Cn2c(=O)c(C(=O)NCc3ccc(Cl)cc3)cc3c4c(cnc32)N(c2cccnc2)CCO4)C1] | 1.1 | 577.1 579.1 | 9 |
| 5018 | 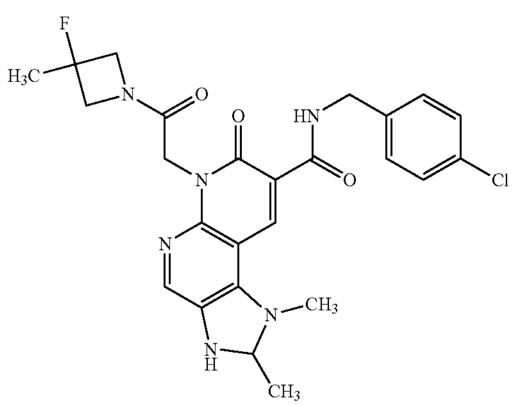 [SMILES: CC1Nc2cnc3c(cc(C(=O)NCc4ccc(Cl)cc4)c(=O)n3CC(=O)N3CC(C)(F)C3)c2N1C] | 1.84 | 513.1 | 20 |

TABLE 5-continued

| Cmpd # | Structure | t_R (min) | (M + H)+ | Ex. # |
|---|---|---|---|---|
| 5019 | 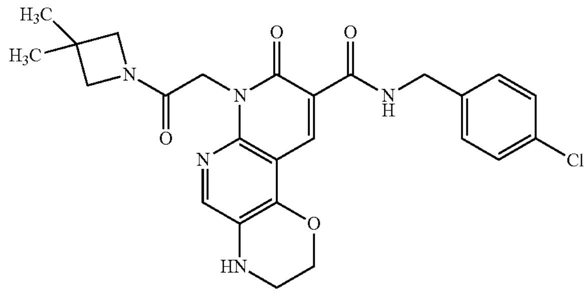 [SMILES: CC1(C)CN(C(=O)Cn2c(=O)c(C(=O)NCc3ccc(Cl)cc3)cc3c4c(cnc32)NCCO4)C1] | 1.4 | 496.1 498.1 | 8 |
| 5020 | 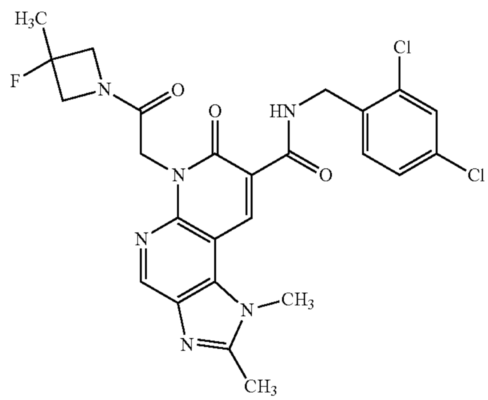 [SMILES: Cc1nc2cnc3c(cc(C(=O)NCc4ccc(Cl)cc4Cl)c(=O)n3CC(=O)N3CC(C)(F)C3)c2n1C] | 1.91 | 545 547 | 28 |
| 5021 | 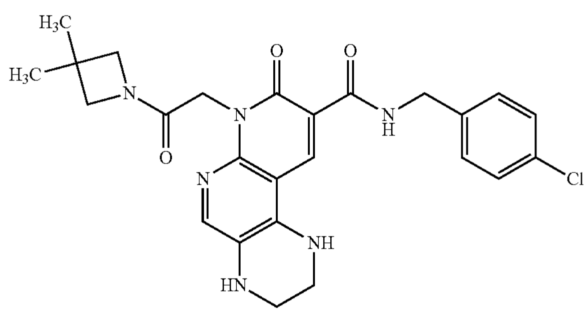 [SMILES: CC1(C)CN(C(=O)Cn2c(=O)c(C(=O)NCc3ccc(Cl)cc3)cc3c4c(cnc32)NCCN4)C1] | 1.1 | 494.9 497.0 | 5 |
| 5022 | 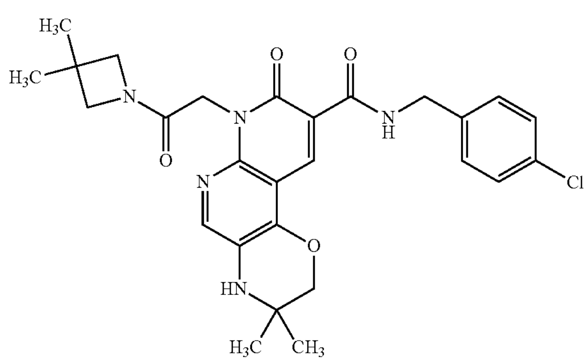 [SMILES: CC1(C)CN(C(=O)Cn2c(=O)c(C(=O)NCc3ccc(Cl)cc3)cc3c4c(cnc32)NC(C)(C)CO4)C1] | 1.5 | 524.2 526.2 | 8 |

TABLE 5-continued

| Cmpd # | Structure | $t_R$ (min) | (M + H)+ | Ex. # |
|---|---|---|---|---|
| 5023 | 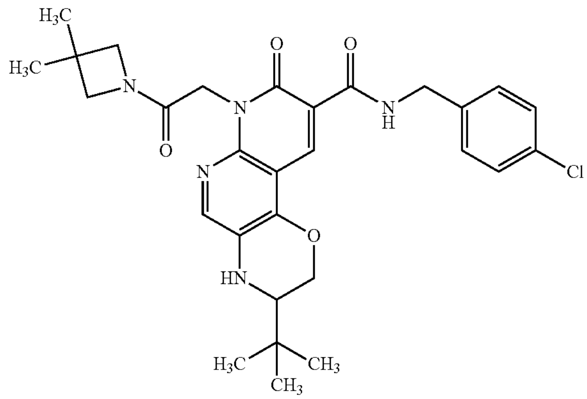 [SMILES: CC1(C)CN(C(=O)Cn2c(=O)c(C(=O)NCc3ccc(Cl)cc3)cc3c4c(cnc32)NC(C(C)(C)C)CO4)C1] | 1.7 | 552.2 554.2 | 8 |
| 5024 | 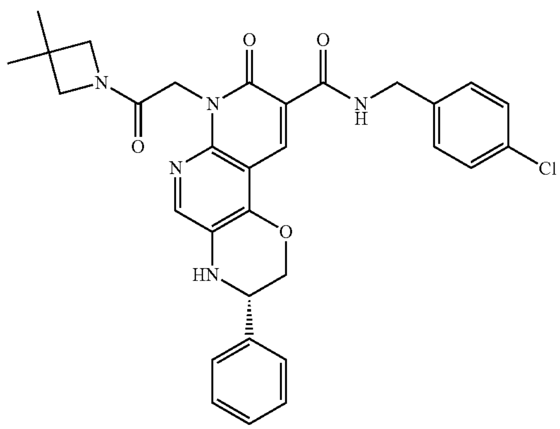 [SMILES: CC1(C)CN(C(=O)Cn2c(=O)c(C(=O)NCc3ccc(Cl)cc3)cc3c4c(cnc32)N[C@@H](c2ccccc2)CO4)C1] | 1.7 | 572.1 574.1 | 8 |
| 5025 | 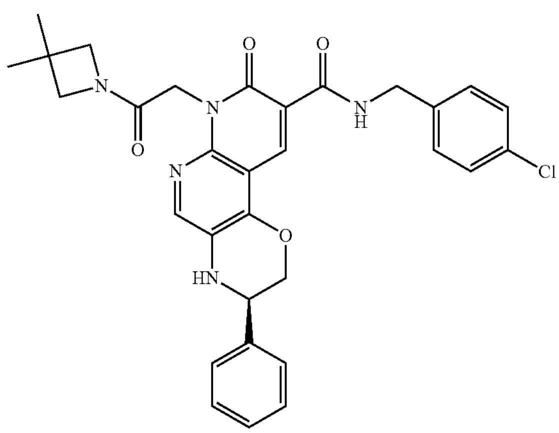 [SMILES: CC1(C)CN(C(=O)Cn2c(=O)c(C(=O)NCc3ccc(Cl)cc3)cc3c4c(cnc32)N[C@H](c2ccccc2)CO4)C1] | 1.7 | 572.1 574.1 | 8 |
| 5026 | 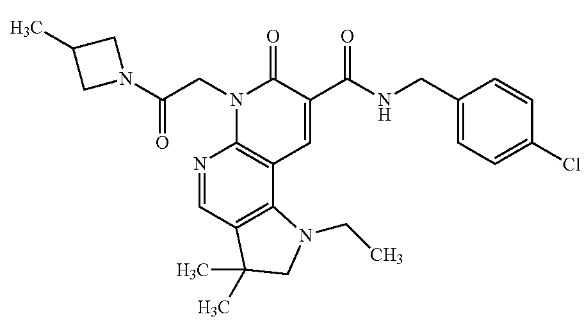 [SMILES: CCN1CC(C)(C)c2cnc3c(cc(C(=O)NCc4ccc(Cl)cc4)c(=O)n3CC(=O)N3CC(C)C3)c21] | 2.04 | 522.3 524.3 | 4 |

TABLE 5-continued
| Cmpd # | Structure | $t_R$ (min) | (M + H)+ | Ex. # |
|---|---|---|---|---|
| 5027 | 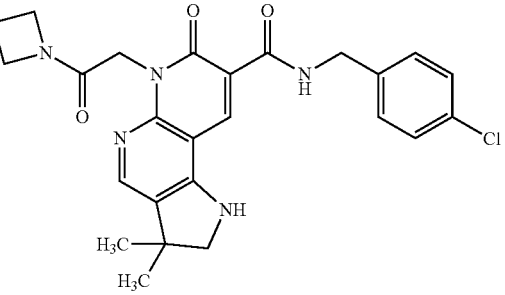 | 2 | 494.3 496.2 | 4 |
| 5028 | 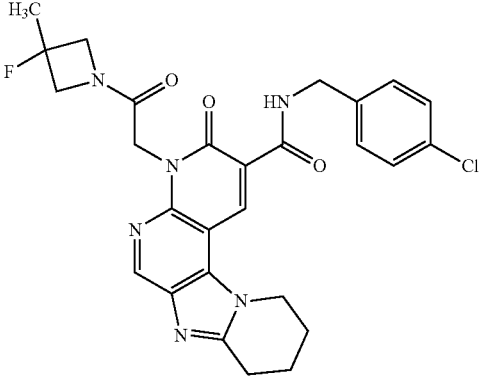 [SMILES: CC1(F)CN(C(=O)Cn2c(=O)c(C(=O)NCc3ccc(Cl)cc3)cc3c4c(cnc32)nc2n4CCCC2)C1] | 1.84 | 537 539 | 23 |
| 5029 | 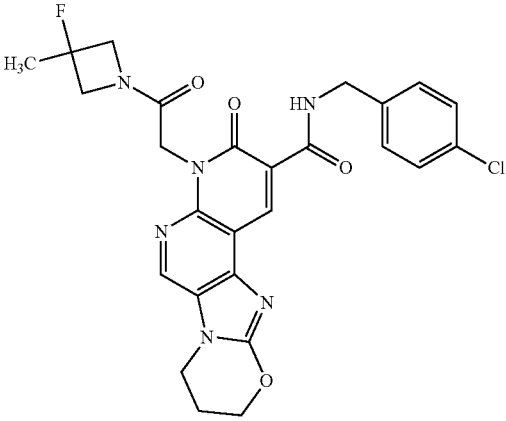 [SMILES: CC1(F)CN(C(=O)Cn2c(=O)c(C(=O)NCc3ccc(Cl)cc3)cc3c4nc5n(c4cnc32)CCCO5)C1] | 5.31 | 539.2 | 17 |
| 5030 | 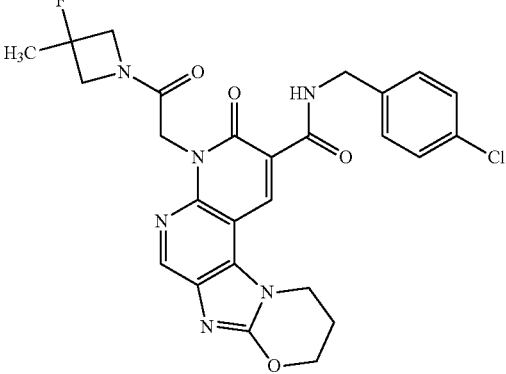 | 5.26 | 539.2 | 17 |

TABLE 5-continued

| Cmpd # | Structure | t<sub>R</sub> (min) | (M + H)+ | Ex. # |
|---|---|---|---|---|
| 5031 | 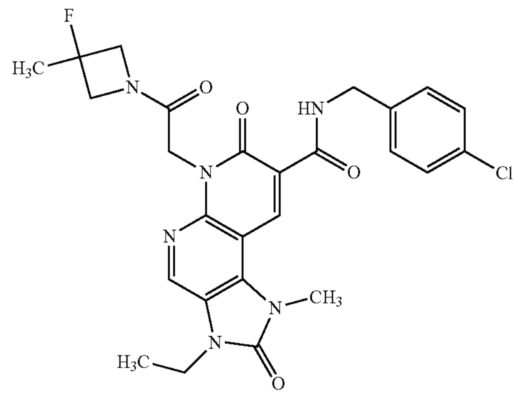 [SMILES: CCn1c(=O)n(C)c2c3cc(C(=O)NCc4ccc(Cl)cc4)c(=O)n(CC(=O)N4CC(C)(F)C4)c3ncc21] | 1.91 | 541.2 | 20 |
| 5032 | 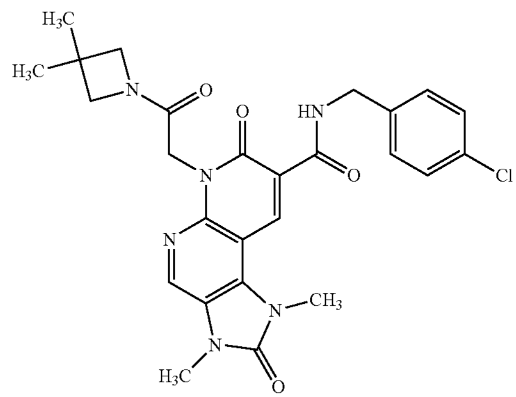 [SMILES: Cn1c(=O)n(C)c2c3cc(C(=O)NCc4ccc(Cl)cc4)c(=O)n(CC(=O)N4CC(C)(C)C4)c3ncc21] | 1.97 | 523.2 | 20 |
| 5033 | 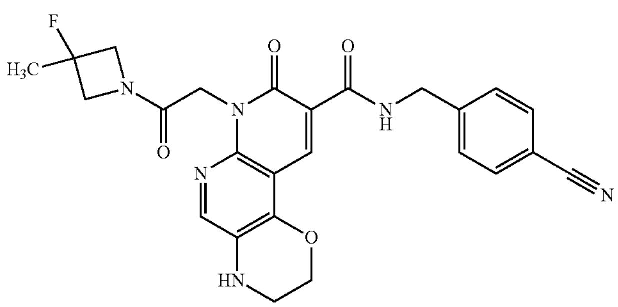 [SMILES: CC1(F)CN(C(=O)Cn2c(=O)c(C(=O)NCc3ccc(C#N)cc3)cc3c4c(cnc32)NCCO4)C1] | 1.1 | 489.1 | 7 |
| 5034 | 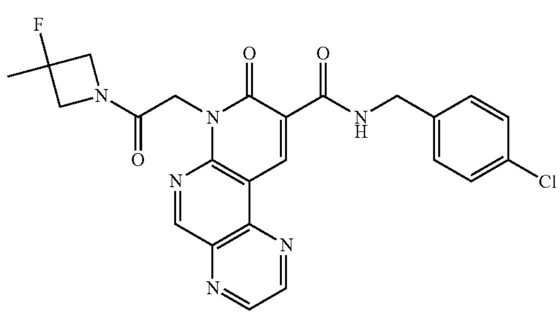 [SMILES: CC1(F)CN(C(=O)Cn2c(=O)c(C(=O)NCc3ccc(Cl)cc3)cc3c4nccnc4cnc32)C1] | 1.86 | 495 / 497 | 12 |

TABLE 5-continued

| Cmpd # | Structure | $t_R$ (min) | (M + H)+ | Ex. # |
|---|---|---|---|---|
| 5035 | 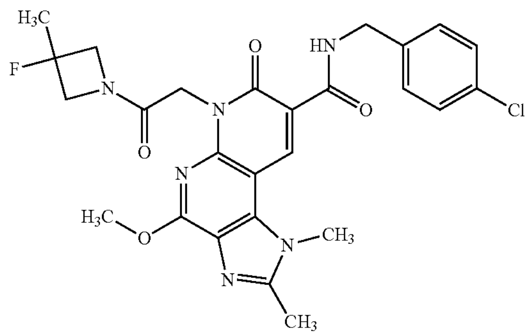 [SMILES: COc1nc2c(cc(C(=O)NCc3ccc(Cl)cc3)c(=O)n2CC(=O)N2CC(C)(F)C2)c2c1nc(C)n2C] | 1.12 | 541.0 543.0 | 24 |
| 5036 | 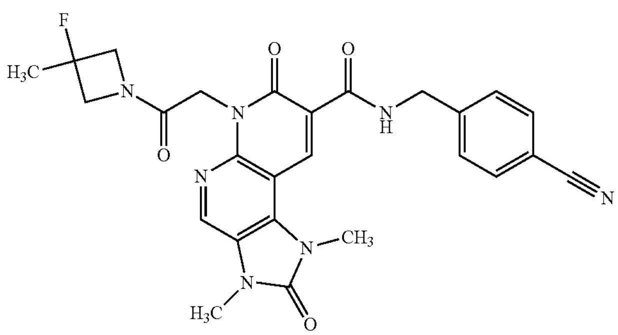 [SMILES: Cn1c(=O)n(C)c2c3cc(C(=O)NCc4ccc(C#N)cc4)c(=O)n(CC(=O)N4CC(C)(F)C4)c3ncc21] | 4.65 | 518.3 | 20 |
| 5037 | 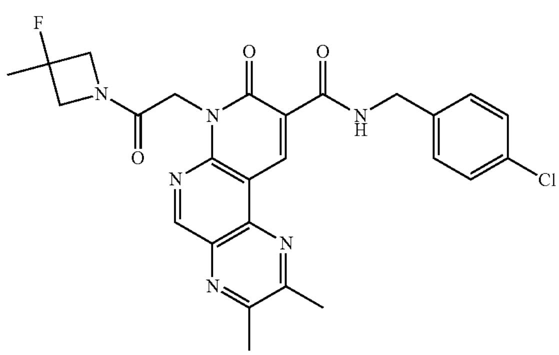 [SMILES: Cc1nc2cnc3c(cc(C(=O)NCc4ccc(Cl)cc4)c(=O)n3CC(=O)N3CC(C)(F)C3)c2nc1C] | 2.02 | 523 525 | 12 |
| 5038 | 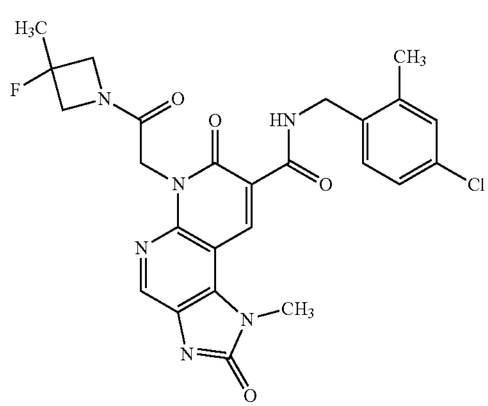 | 1.87 | 525 527 | 28 |

TABLE 5-continued

| Cmpd # | Structure | $t_R$ (min) | (M + H)+ | Ex. # |
|---|---|---|---|---|
| 5039 | 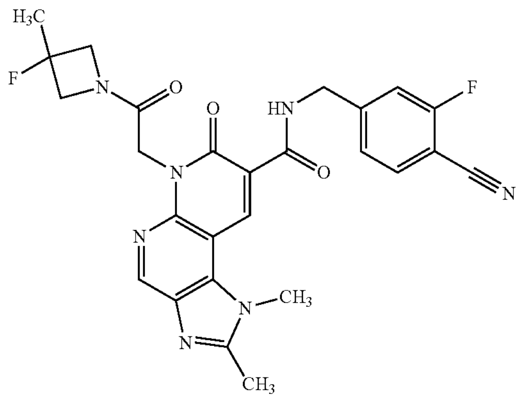 [SMILES: Cc1nc2cnc3c(cc(C(=O)NCc4ccc(C#N)c(F)c4)c(=O)n3CC(=O)N3CC(C)(F)C3)c2n1C] | 1.13 | 520 | 28 |
| 5040 | 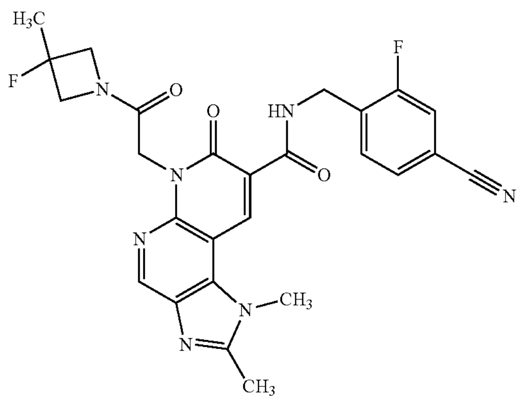 [SMILES: Cc1nc2cnc3c(cc(C(=O)NCc4ccc(C#N)cc4F)c(=O)n3CC(=O)N3CC(C)(F)C3)c2n1C] | 1.57 | 520 | 28 |
| 5041 | 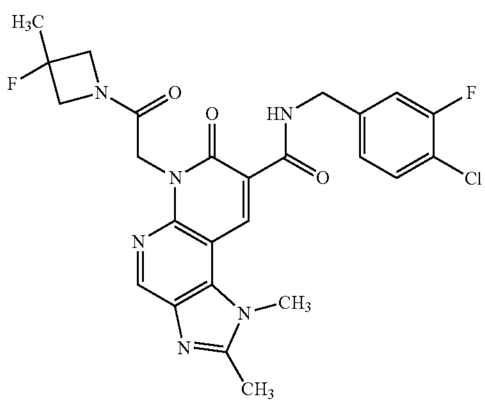 [SMILES: Cc1nc2cnc3c(cc(C(=O)NCc4ccc(Cl)c(F)c4)c(=O)n3CC(=O)N3CC(C)(F)C3)c2n1C] | 1.79 | 529 531 | 28 |
| 5042 | 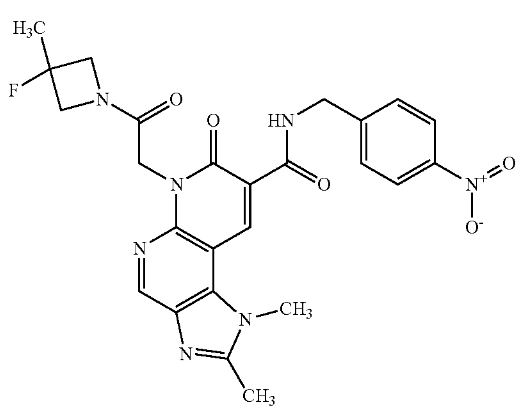 [SMILES: Cc1nc2cnc3c(cc(C(=O)NCc4ccc([N+](=O)[O-])cc4)c(=O)n3CC(=O)N3CC(C)(F)C3)c2n1C] | 1.6 | 522 | 28 |

TABLE 5-continued

| Cmpd # | Structure | $t_R$ (min) | (M + H)+ | Ex. # |
|---|---|---|---|---|
| 5043 | 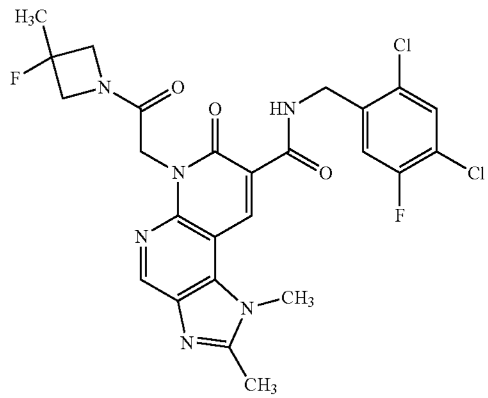 [SMILES: Cc1nc2cnc3c(cc(C(=O)NCc4cc(F)c(Cl)cc4Cl)c(=O)n3CC(=O)N3CC(C)(F)C3)c2n1C] | 1.92 | 563, 565 | 28 |
| 5044 | 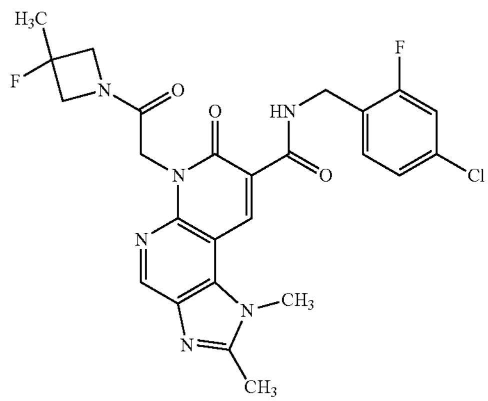 [SMILES: Cc1nc2cnc3c(cc(C(=O)NCc4ccc(Cl)cc4F)c(=O)n3CC(=O)N3CC(C)(F)C3)c2n1C] | 1.82 | 529, 531 | 28 |
| 5045 | 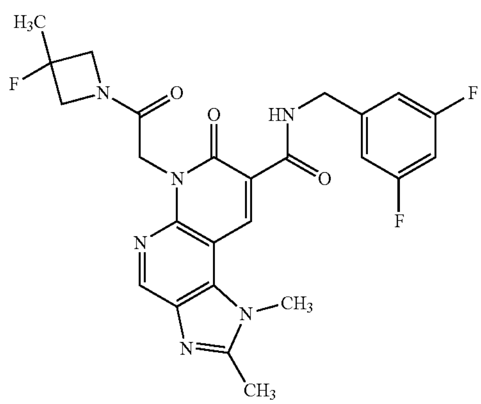 [SMILES: Cc1nc2cnc3c(cc(C(=O)NCc4cc(F)cc(F)c4)c(=O)n3CC(=O)N3CC(C)(F)C3)c2n1C] | 1.72 | 513 | 28 |
| 5046 | 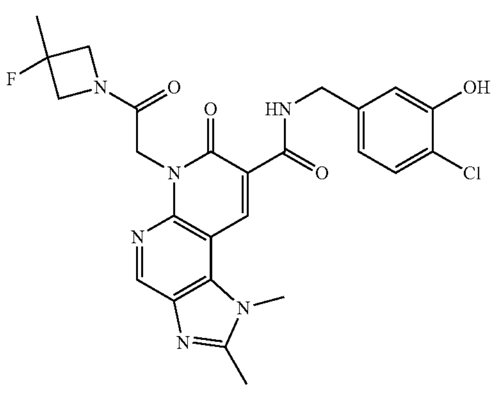 [SMILES: Cc1nc2cnc3c(cc(C(=O)NCc4ccc(Cl)c(O)c4)c(=O)n3CC(=O)N3CC(C)(F)C3)c2n1C] | 0.96 | 527, 529 | 28 |

TABLE 5-continued

| Cmpd # | Structure | $t_R$ (min) | (M + H)+ | Ex. # |
|---|---|---|---|---|
| 5047 | 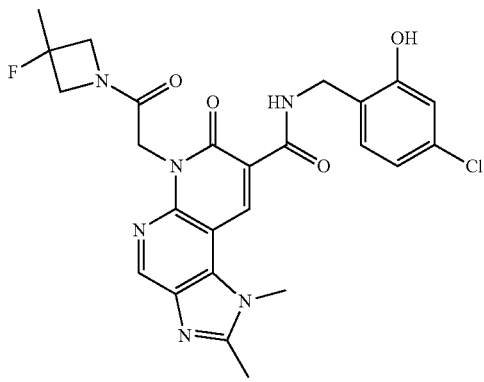 [SMILES: Cc1nc2cnc3c(cc(C(=O)NCc4ccc(Cl)cc4O)c(=O)n3CC(=O)N3CC(C)(F)C3)c2n1C] | 1.14 | 527 529 | 28 |
| 5048 | 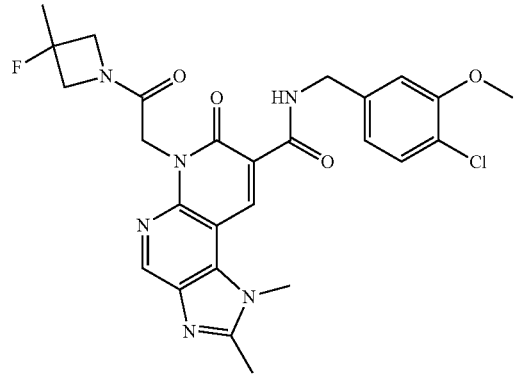 [SMILES: COc1cc(CNC(=O)c2cc3c4c(cnc3n(CC(=O)N3CC(C)(F)C3)c2=O)nc(C)n4C)ccc1Cl] | 1.21 | 541 543 | 28 |

Each reference, including all patents, patent applications, and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A compound of Formula (I):

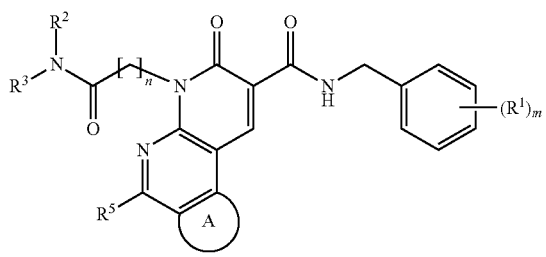

(I)

wherein, n is 1, 2 or 3;

m is 1, 2 or 3;

$R^1$ is halo, —CN, $(C_{1-6})$alkyl, OH, —O—$(C_{1-6})$alkyl, $(C_{1-6})$haloalkyl or nitro;

$R^2$ is H or $(C_{1-6})$alkyl optionally substituted with halo, —CN, —$(C_{3-7})$cycloalkyl, —O—$(C_{1-6})$alkyl, OH, —NH$_2$, —NH$(C_{1-6})$alkyl or —N$((C_{1-6})$alkyl$)_2$;

$R^3$ is H, $(C_{1-6})$alkyl, $(C_{3-7})$cycloalkyl, aryl, heterocyclyl, heteroaryl, —$(C_{1-6})$alkyl-$(C_{3-7})$cycloalkyl, —$(C_{1-6})$alkyl-aryl, —$(C_{1-6})$alkyl-heterocyclyl or —$(C_{1-6})$alkyl-heteroaryl, wherein each said alkyl, cycloalkyl, aryl, heterocyclyl and heteroaryl, either alone or in combination with another radical, is optionally mono-, di-, or tri-substituted with $R^{32}$;

or $R^2$ and $R^3$, together with the N to which they are attached, are linked to form a heterocyclyl or heteroaryl; wherein each said heterocyclyl and heteroaryl are optionally mono-, di-, or tri-substituted with $R^{32}$;

$R^{32}$ is each independently selected from the group consisting of $R^{33}$, halo, oxo, —CN, OH, SH, —COOH, —$(C_{1-6})$alkyl; —O—$(C_{1-6})$alkyl, —S—$(C_{1-6})$alkyl, $(C_{3-7})$cycloalkyl, $(C_{1-6})$haloalkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl$)_2$, —C(=O)—NH—SO$_2(C_{1-6})$alkyl, —SO$_2$—NH—C(=O)—$(C_{1-6})$alkyl, —NH$_2$, —NH$(C_{1-6})$alkyl, —N$((C_{1-6})$alkyl$)_2$, —NH$(C_{3-7})$cycloalkyl, —N$((C_{1-6})$alkyl$)(C_{3-7})$cycloalkyl, —NH—C(=O)$(C_{1-6})$alkyl, —NH—C(=O)O$(C_{1-6})$alkyl, heterocyclyl (optionally substituted with $(C_{1-6})$alkyl) and heteroaryl (optionally substituted with $(C_{1-6})$alkyl);

$R^{33}$ is $(C_{1-6})$alkyl optionally mono- or di-substituted with OH, —O—$(C_{1-6})$alkyl, —NH$_2$, —NH$(C_{1-6})$alkyl or —N$((C_{1-6})$alkyl$)_2$;

Ring A is an imidazole ring, optionally mono-, di-, or tri-substituted with $R^4$;

$R^4$ is each independently selected from the group consisting of halo, oxo, cyano, nitro, $(C_{1-6})$alkylidene, $R^{42}$, —C(=O)—$R^{42}$, —C(=O)O$R^{42}$, —O$R^{42}$, —S$R^{42}$, —SO$R^{42}$, —SO$_2R^{42}$, —N$(R^{43})R^{42}$, —$(C_{1-6})$alkyl-N$(R^{43})R^{42}$, —C(=O)—N$(R^{43})R^{42}$, —N$(R^{43})$—C(=O)$R^{42}$, —N$(R^{43})$—C(=O)O—$R^{42}$, —C(=O)—N(H)—SO$_2R^{42}$, —SO$_2$—N(H)—C(=O)$R^{42}$, —O—C(=O)—N$(R^{43})R^{42}$ and —SO$_2$—N$(R^{43})R^{42}$;

$R^{42}$ is each independently selected from the group consisting of H, $(C_{1-6})$alkyl, $(C_{2-6})$alkenyl, $(C_{2-6})$alkynyl, —$(C_{1-6})$alkyl-$(C_{3-7})$cycloalkyl, —$(C_{1-6})$alkyl-aryl, —$(C_{1-6})$alkyl-heterocyclyl, —$(C_{1-6})$alkyl-heteroaryl, $(C_{3-7})$cycloalkyl, aryl, heterocyclyl and heteroaryl, wherein each said alkyl, alkenyl, alkynyl, cycloalkyl, aryl, heterocyclyl and heteroaryl, either alone or in combination with another radical, is optionally substituted with 1 to 3 substituents each independently selected from the group consisting of: halo, cyano, OH, —COOH, —O—$(C_{1-6})$alkyl, —S—$(C_{1-6})$alkyl, $(C_{3-7})$cycloalkyl, —O—$(C_{3-7})$cycloalkyl, $(C_{1-6})$haloalkyl, —C(=O)—$(C_{1-6})$alkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl$)_2$, —C(=O)—N(H)—SO$_2(C_{1-6})$alkyl, —SO$_2$—N(H)—C(=O)$(C_{1-6})$alkyl, —NH$_2$, —NH$(C_{1-6})$alkyl, —N$((C_{1-6})$alkyl$)_2$, —NH—C(=O)$(C_{1-6})$alkyl, —NH—C(=O)—O$(C_{1-6})$alkyl and $(C_{1-6})$alkyl optionally mono- or di-substituted with OH, —O—$(C_{1-6})$alkyl, —S—$(C_{1-6})$alkyl, —SO$(C_{1-6})$alkyl, —SO$_2(C_{1-6})$alkyl, heterocyclyl or heteroaryl;

$R^{43}$ is H, $(C_{1-6})$haloalkyl or $(C_{1-6})$alkyl optionally mono- or di-substituted with OH, —O—$(C_{1-6})$alkyl or —O—$(C_{3-7})$cycloalkyl; and $R^5$ is H, halo, —CN, $(C_{1-6})$alkyl, $(C_{1-6})$haloalkyl, —O—$(C_{1-6})$alkyl, $(C_{3-7})$cycloalkyl, —NH$_2$, —NH$(C_{1-6})$alkyl or —N$((C_{1-6})$alkyl$)_2$;

or a salt thereof.

2. The compound according to claim 1, or a pharmaceutically acceptable salt thereof, wherein n is 1 or 2.

3. The compound according to claim 1, or a pharmaceutically acceptable salt thereof, wherein n is 1.

4. The compound according to claim 1, or a pharmaceutically acceptable salt thereof, wherein m is 1 or 2.

5. The compound according to claim 1, or a pharmaceutically acceptable salt thereof, wherein m is 1.

6. The compound according to claim 1, or a pharmaceutically acceptable salt thereof, wherein $R^1$ is F, Cl, Br, —CN, OH, O—$(C_{1-3})$alkyl, $(C_{1-3})$alkyl, $(C_{1-3})$haloalkyl or nitro.

7. The compound according to claim 1, or a pharmaceutically acceptable salt thereof, wherein $R^1$ is F, Cl, Br, —CN, OH or O—$(C_{1-3})$alkyl.

8. The compound according to claim 1, or a pharmaceutically acceptable salt thereof, wherein $R^2$ is H or $(C_{1-6})$alkyl; $R^3$ is $(C_{1-6})$alkyl, —$(C_{1-6})$alkyl-$(C_{3-7})$cycloalkyl, —$(C_{1-6})$alkyl-aryl, —$(C_{1-6})$alkyl-heterocyclyl or —$(C_{1-6})$alkyl-heteroaryl, wherein each said alkyl, cycloalkyl, aryl, heterocyclyl and heteroaryl, either alone or in combination with another radical, is optionally mono-, di-, or tri-substituted with $R^{32}$; or $R^2$ and $R^3$, together with the N to which they are attached, are linked to form a heterocyclyl; wherein said heterocyclyl is optionally mono-, di-, or tri-substituted with $R^{32}$;

$R^{32}$ is each independently selected from the group consisting of $R^{33}$, halo, oxo, —CN, OH, —COOH, —$(C_{1-6})$alkyl, —O—$(C_{1-6})$alkyl, $(C_{3-7})$cycloalkyl, $(C_{1-6})$haloalkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl)$_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl)$_2$, —C(=O)—NH—SO$_2(C_{1-6})$alkyl, —SO$_2$—NH—C(=O)—$(C_{1-6})$alkyl, heterocyclyl (optionally substituted with $(C_{1-6})$alkyl) and heteroaryl (optionally substituted with $(C_{1-6})$alkyl);

$R^{33}$ is $(C_{1-6})$alkyl optionally mono- or di-substituted with OH, —O—$(C_{1-6})$alkyl, —NH$_2$, —NH$(C_{1-6})$alkyl or —N$((C_{1-6})$alkyl)$_2$.

9. The compound according to claim 1, or a pharmaceutically acceptable salt thereof, wherein $R^2$ and $R^3$, together with the N to which they are attached, are linked to form a heterocyclyl; wherein said heterocyclyl is optionally mono- or di-substituted with $R^{32}$;

$R^{32}$ is each independently selected from the group consisting of $R^{33}$, halo, oxo, —CN, OH, —COOH, —$(C_{1-6})$alkyl, —O—$(C_{1-6})$alkyl, $(C_{3-7})$cycloalkyl, $(C_{1-6})$haloalkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl)$_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl)$_2$, —C(=O)—NH—SO$_2(C_{1-6})$alkyl, —SO$_2$—NH—C(=O)—$(C_{1-6})$alkyl, heterocyclyl (optionally substituted with $(C_{1-6})$alkyl) and heteroaryl (optionally substituted with $(C_{1-6})$alkyl);

$R^{33}$ is —$(C_{1-6})$alkyl optionally mono- or di-substituted with OH, —O—$(C_{1-6})$alkyl, —NH$_2$, —NH$(C_{1-6})$alkyl or —N$((C_{1-6})$alkyl)$_2$.

10. The compound according to claim 1, or a pharmaceutically acceptable salt thereof, wherein $R^2$ and $R^3$, together with the N to which they are attached, are linked to form a heterocyclyl, wherein said heterocyclyl is optionally mono- or di-substituted with $R^{32}$;

$R^{32}$ is each independently selected from the group consisting of $R^{33}$, —CN, $(C_{1-6})$haloalkyl, halo and —O$(C_{1-6})$alkyl;

$R^{33}$ is $(C_{1-6})$alkyl optionally mono- or di-substituted with OH.

11. The compound according to claim 1, or a pharmaceutically acceptable salt thereof, wherein;

$R^4$ is each independently selected from the group consisting of halo, oxo, cyano, $R^{42}$, —C(=O)OR$_{42}$, —OR$^{42}$, —N$(R^{43})R^{42}$ and —$(C_{1-6})$alkyl-N$(R^{43})R^{42}$;

$R^{42}$ is each independently selected from the group consisting of H, $C_{1-6}$alkyl, —$(C_{1-6})$alkyl-$(C_{3-7})$cycloalkyl, —$(C_{1-6})$alkyl-aryl, —$(C_{1-6})$alkyl-heterocyclyl, —$(C_{1-6})$alkyl-heteroaryl, $(C_{3-7})$cycloalkyl, aryl, heterocyclyl and heteroaryl, wherein each said alkyl, cycloalkyl, aryl, heterocyclyl and heteroaryl, either alone or in combination with another radical, is optionally substituted with 1 to 2 substituents each independently selected from the group consisting of: halo, oxo, cyano, OH, —COOH, —O—$(C_{1-6})$alkyl, —S—$(C_{1-6})$alkyl, $(C_{3-7})$cycloalkyl, $(C_{1-6})$haloalkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl)$_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl)$_2$, —NH$_2$, —NH$(C_{1-6})$alkyl, —N$((C_{1-6})$alkyl)$_2$, —NH—C(=O)$(C_{1-6})$alkyl and $(C_{1-6})$alkyl optionally mono- or di-substituted with OH or —O—$(C_{1-6})$alkyl;

$R^{43}$ is H, $(C_{1-3})$haloalkyl or $(C_{1-3})$alkyl optionally mono- or di-substituted with OH, —O—$(C_{1-3})$alkyl or —O—$(C_{3-5})$cycloalkyl.

12. The compound according to claim 1, or a pharmaceutically acceptable salt thereof, wherein the imidazole ring, A is optionally mono- or di-substituted with $R^4$;

$R^4$ is each independently selected from the group consisting of $R^{42}$, OR$^{42}$ and N$(R^{43})R^{42}$;

$R^{42}$ is each independently selected from the group consisting of $(C_{1-6})$alkyl, —$(C_{1-6})$alkyl-$(C_{3-7})$cycloalkyl, $(C_{3-7})$cycloalkyl, heterocyclyl and heteroaryl, wherein each said alkyl, cycloalkyl, heterocyclyl and heteroaryl, either alone or in combination with another radical, is optionally substituted with 1 to 2 substituents each independently selected from the group consisting of: halo, oxo, cyano, OH, —COOH, —O—$(C_{1-4})$alkyl, $(C_{3-7})$cycloalkyl, $(C_{1-4})$haloalkyl, —SO$_2$NH$_2$, —SO$_2$—NH$(C_{1-4})$alkyl, —SO$_2$—N$((C_{1-4})$alkyl)$_2$, —SO$(C_{1-4})$alkyl, —SO$_2(C_{1-4})$alkyl, —C(=O)—NH$_2$, —C(=O)—NH$(C_{1-4})$alkyl, —C(=O)—N$((C_{1-4})$alkyl)$_2$, —NH$_2$, —NH$(C_{1-4})$alkyl, —N$((C_{1-4})$alkyl)$_2$, —NH—C(=O)$(C_{1-4})$alkyl and $(C_{1-4})$alkyl optionally mono- or di-substituted with OH or —O—$(C_{1-4})$alkyl;

$R^{43}$ is H, $(C_{1-3})$haloalkyl or $(C_{1-3})$alkyl optionally mono- substituted with OH, —O—$(C_{1-3})$alkyl or —O—$(C_{3-5})$ cycloalkyl.

13. The compound according to claim 1, or a pharmaceutically acceptable salt thereof, wherein the imidazole ring, A is optionally mono- or di-substituted with $R^4$;

$R^4$ is each independently selected from the group consisting of $R^{42}$, OR$^{42}$ and N$(R^{43})R^{42}$;

$R^{42}$ is each independently selected from the group consisting of $(C_{1-6})$alkyl, —$(C_{1-6})$alkyl-$(C_{3-7})$cycloalkyl, $(C_{3-7})$cycloalkyl, heterocyclyl and heteroaryl, wherein each said alkyl, cycloalkyl, heterocyclyl and heteroaryl, either alone or in combination with another radical, is optionally substituted with 1 to 2 substituents each independently selected from the group consisting of: halo, oxo, cyano, OH, —COOH, $(C_{3-7})$cycloalkyl, $(C_{1-4})$haloalkyl, —SO$_2$NH$_2$, —SO$_2$—NH$(C_{1-4})$alkyl, —SO$_2$—N$((C_{1-4})$alkyl)$_2$, —SO$(C_{1-4})$alkyl, —SO$_2(C_{1-4})$alkyl, —C(=O)—NH$_2$, —C(=O)—NH$(C_{1-4})$alkyl, —C(=O)—N$((C_{1-4})$alkyl)$_2$, —NH$_2$, —NH$(C_{1-4})$alkyl, —N$((C_{1-4})$alkyl)$_2$, —NH—C(=O)$(C_{1-4})$alkyl and $(C_{1-4})$alkyl optionally mono- or di-substituted with OH or —O—$(C_{1-4})$alkyl;

$R^{43}$ is H or $(C_{1-3})$alkyl.

14. The compound according to claim 1, or a pharmaceutically acceptable salt thereof, wherein $R^5$ is H, —O—$(C_{1-4})$alkyl, —NH$_2$ or —NH$(C_{1-4})$alkyl.

15. The compound according to claim 1, or a pharmaceutically acceptable salt thereof, wherein $R^5$ is H or —O—$(C_{1-4})$alkyl.

16. The compound according to claim 1, or a pharmaceutically acceptable salt thereof, wherein $R^5$ is H.

17. A pharmaceutical composition comprising a compound of Formula (I) according to claim 1, or a pharmaceutically acceptable salt thereof, and a pharmaceutically acceptable carrier.

18. The pharmaceutical composition according to claim 17 further comprising a therapeutically effective amount of at least one other antiviral agent.

19. A compound of formula (1) according to claim 1, selected from a group consisting of:

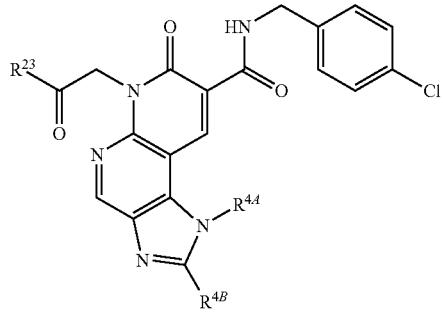

| Cmpd # | R^{4A} | R^{4B} | R^{23} | Ex. # |
|---|---|---|---|---|
| 1001 | *—CH₃ | *—CH₃ | oxetane-spiro-azetidinyl | 27 |
| 1002 | *—CH₃ | *—CH₃ | 3-fluoro-3-methylazetidinyl | 19 |
| 1003 | *—CH₃ | *—N(CH₃)S(O)₂CH₃ | 3-fluoro-3-methylazetidinyl | 31 |
| 1004 | *—CH₂CH₃ | H | 3-fluoro-3-methylazetidinyl | 22 |
| 1005 | *—CH₂CH₃ | *—CH₂CH₃ | 3-fluoro-3-methylazetidinyl | 22 |
| 1006 | *—CH₃ | *-cyclobutyl | 3-fluoro-3-methylazetidinyl | 25 |
| 1007 | *—CH₃ | *—CH₃ | 3-fluoro-3-(fluoromethyl)azetidinyl | 27 |
| 1008 | *—CH₃ | *—CH₃ | cyclopropane-spiro-azetidinyl | 27 |
| 1009 | *—CH₂CH₃ | *—CH₃ | 3-fluoro-3-methylazetidinyl | 21 |
| 1010 | *—CH₃ | *—CF₃ | 3-fluoro-3-methylazetidinyl | 26 |

-continued
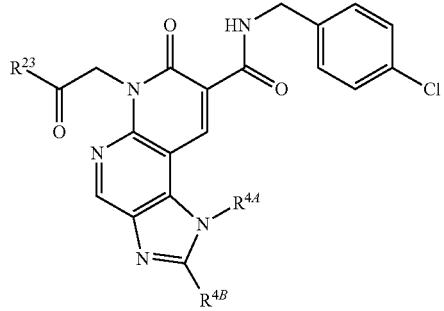
(1)
| Cmpd # | R4A | R4B | R23 | Ex. # |
|---|---|---|---|---|
| 1011 | —CH3 | —CH3 | pyrazol-1-yl-azetidinyl | 27 |
| 1012 | —CH3 | H | 3-fluoro-3-methyl-azetidinyl | 19 |
| 1013 | —CH3 | —CH2NHCH3 | 3-fluoro-3-methyl-azetidinyl | 24 |
| 1014 | —CH3 | —CH3 | N-methyl-N-cyclohexyl-amino | 27 |
| 1015 | —CH3 | —CH3 | 3-(fluoromethyl)-azetidinyl | 27 |
| 1016 | —CH3 | 1-methyl-pyrazol-4-yl | 3-fluoro-3-methyl-azetidinyl | 26 |
| 1017 | —CH3 | —CH3 | 2-(hydroxymethyl)-azetidinyl | 27 |
| 1018 | —CH3 | tetrahydrofuran-2-yl | 3-fluoro-3-methyl-azetidinyl | 26 |

-continued
(1)
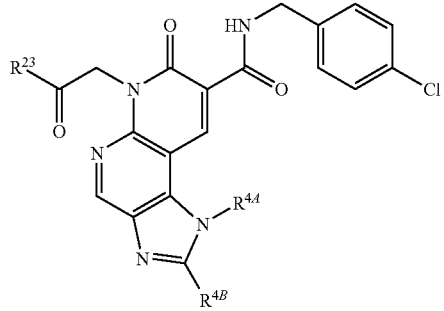
| Cmpd # | R4A | R4B | R23 | Ex. # |
|---|---|---|---|---|
| 1019 | *—CH3 | *—CH3 | methyl 3-methylazetidine-3-carboxylate-N-acetyl | 27 |
| 1020 | *—CH3 | *—CH3 | 3-cyanopyrrolidine-N-acetyl | 27 |
| 1021 | *—CH3 | 5-(2-(dimethylamino)pyrimidinyl)* | 3-fluoro-3-methylazetidine-N-acetyl | 26 |
| 1022 | *—CH3 | *—CH2C(O)OCH2CH3 | 3-fluoro-3-methylazetidine-N-acetyl | 19 |
| 1023 | *—CH3 | *—CH3 | 2-(azetidin-3-yl)-2-methylpropanenitrile-N-acetyl | 27 |
| 1024 | *—CH2CH2OH | H | 3-fluoro-3-methylazetidine-N-acetyl | 21 |
| 1025 | H | H | 3-fluoro-3-methylazetidine-N-acetyl | 13 |

-continued (1)

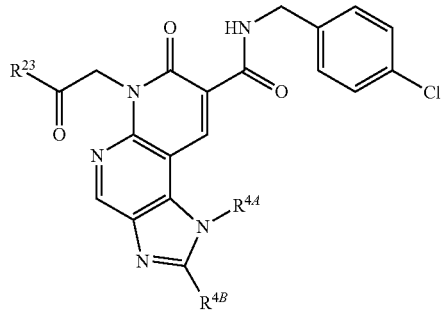

| Cmpd # | R^4A | R^4B | R^23 | Ex. # |
|---|---|---|---|---|
| 1026 | —CH₃ | 2-methyl-1H-imidazol-4-yl | 3-fluoro-3-methylazetidin-1-yl | 26 |
| 1027 | —CH₃ | N-methylamino | 3-fluoro-3-methylazetidin-1-yl | 31 |
| 1028 | —CH₃ | morpholin-4-ylmethyl | 3-fluoro-3-methylazetidin-1-yl | 24 |
| 1029 | —CH₃ | azetidin-1-ylmethyl | 3-fluoro-3-methylazetidin-1-yl | 24 |
| 1030 | —CH₃ | (3,3-difluoroazetidin-1-yl)methyl | 3-fluoro-3-methylazetidin-1-yl | 24 |
| 1031 | —CH₃ | methoxymethyl | 3-fluoro-3-methylazetidin-1-yl | 24 |
| 1032 | —CH₃ | cyclopropylmethyl | 3-fluoro-3-methylazetidin-1-yl | 25 |

-continued (1)

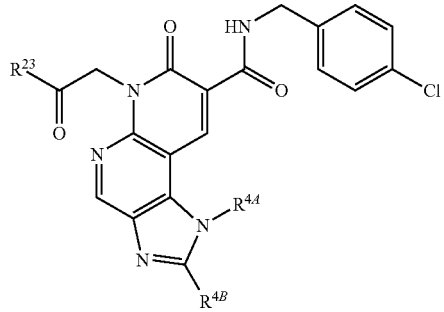

| Cmpd # | R<sup>4A</sup> | R<sup>4B</sup> | R<sup>23</sup> | Ex. # |
|---|---|---|---|---|
| 1033 | *—CH₃ | *—CH₂—S(O)₂—CH₃ | 3-fluoro-3-methylazetidin-1-yl | 24 |
| 1034 | *—CH₃ | *—S(O)₂—CH₃ | 3-fluoro-3-methylazetidin-1-yl | 31 |
| 1035 | *—CH₃ | *-tetrahydropyran-4-yl | 3-fluoro-3-methylazetidin-1-yl | 25 |
| 1036 | *—CH₃ | *—CH₂CH₂—S(O)—CH₃ | 3-fluoro-3-methylazetidin-1-yl | 25 |
| 1037 | *—CH₃ | *—CH₂CH₂—S(O)₂—CH₃ | 3-fluoro-3-methylazetidin-1-yl | 25 |
| 1038 | *—CH₃ | *-(2-oxopyrrolidin-1-yl) | 3-fluoro-3-methylazetidin-1-yl | 31 |
| 1039 | *—CH₃ | *—CH₂—N(CH₃)—CH₂CH₂—O—CH₃ | 3-fluoro-3-methylazetidin-1-yl | 24 |

-continued

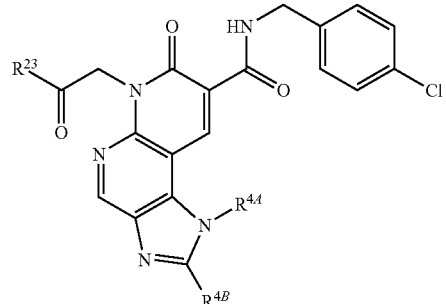
(1)

| Cmpd # | R4A | R4B | R23 | Ex. # |
|---|---|---|---|---|
| 1040 | *—CH₃ | *—S(=O)—CH₃ (methylsulfonyl) | 3-fluoro-3-methylazetidinyl | 31 |
| 1041 | *—CH₃ | *—CH₂CN | 3-fluoro-3-methylazetidinyl | 25 |
| 1042 | *—CH₃ | *—CH₂CH₂COOH | 3-fluoro-3-methylazetidinyl | 25 |
| 1043 | *—CH₃ | *—C(CH₃)₂CH₂OH | 3-fluoro-3-methylazetidinyl | 25 |
| 1044 | *—CH₃ | *—OCH₃ | 3-fluoro-3-methylazetidinyl | 19 |
| 1045 | *—CH₃ | *—N(CH₃)₂ | 3-fluoro-3-methylazetidinyl | 18 |
| 1046 | *—CH₃ | *—CH₂N(CH₃)CH₂CH₂F | 3-fluoro-3-methylazetidinyl | 24 |
| 1047 | *—CH₃ | *—CH₂N(CH₃)CH₂CN | 3-fluoro-3-methylazetidinyl | 24 |

-continued
(1)
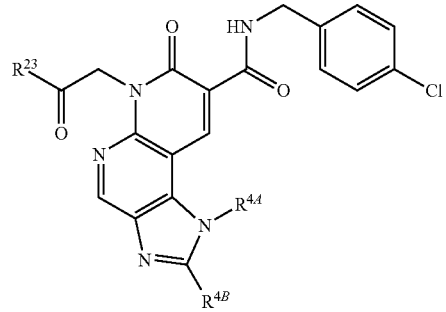
| Cmpd # | R4A | R4B | R23 | Ex. # |
|---|---|---|---|---|
| 1048 | *—CH3 | *—O—CH2CH3 | H3C, F, azetidine | 19 |
| 1049 | *—CH3 | *-(1-methylpyrrolidin-2-yl) | H3C, F, azetidine | 25 |
| 1050 | *—CH3 | *-pyrrolidin-1-yl | F, H3C, azetidine | 31 |
| 1051 | *—CH3 | *—NH—CH2CH2—NH—C(O)CH3 | F, H3C, azetidine | 31 |
| 1052 | *—CH3 | *—NH—S(O)2—N(CH3)2 | F, H3C, azetidine | 31 |
| 1053 | *—CH3 | *—CH3 | H3C, azetidine | 27 |
| 1054 | *—CH3 | *-(4-methylpiperazin-1-yl) | F, H3C, azetidine | 31 |
| 1055 | *—CH3 | *-cyclobutyl | H3C, azetidine | 25-26 |

-continued (1)

| Cmpd # | R4A | R4B | R23 | Ex. # |
|---|---|---|---|---|
| 1056 | *—CH₃ | *-N-morpholine | 3-fluoro-3-methylazetidin-1-yl | 31 |
| 1057 | *—CH₃ | *-tetrahydrofuran-3-yl | 3,3-dimethylazetidin-1-yl | 25-26 |
| 1058 | *—CH₃ | *-N-azetidine | 3-fluoro-3-methylazetidin-1-yl | 31 |
| 1059 | *—CH₃ | *-NH-S(O)₂-CH₃ | 3-fluoro-3-methylazetidin-1-yl | 31 |
| 1060 | *—CH₃ | *-O-CH₂-C(CH₃)(COOH)- | 3-fluoro-3-methylazetidin-1-yl | 31 |
| 1061 | *—CH₃ | *-N-imidazole | 3-fluoro-3-methylazetidin-1-yl | 31 |
| 1062 | *—CH₃ | *—CH₃ | 3-hydroxy-3-methylazetidin-1-yl | 27 |
| 1063 | *—CH₃ | *—CH₃ | 3-fluoroazetidin-1-yl | 27 |
| 1064 | *—CH₃ | *—CH₃ | 3,3-difluoroazetidin-1-yl | 27 |
| 1065 | *—CH₃ | *—CH₃ | 3-fluoro-3-(hydroxymethyl)azetidin-1-yl | 27 |

-continued
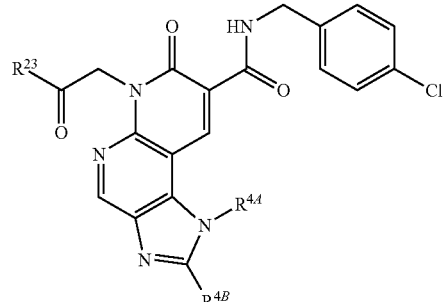
(1)
| Cmpd # | R4A | R4B | R23 | Ex. # |
|---|---|---|---|---|
| 1066 | *—CH3 | *—CH3 | 3-methoxyazetidin-1-yl | 27 |
| 1067 | *—CH3 | *—CH3 | 3-cyanoazetidin-1-yl | 27 |
| 1068 | *—CH3 | *—CH3 | 3-(methylsulfonyl)azetidin-1-yl | 27 |
| 1069 | *—CH3 | *—CH3 | 3-cyano-3-methylazetidin-1-yl | 27 |
| 1070 | *—CH3 | *—CH2—N(CH3)2 | 3,3-dimethylazetidin-1-yl | 24 |
| 1071 | *—CH3 | *—CH3 | 2,6-diazaspiro[3.3]heptan-2-yl | 27 |
| 1072 | *—CH3 | *—CH3 | 6,6-difluoro-2-azaspiro[3.3]heptan-2-yl | 27 |
| 1073 | *—CH3 | *—CH3 | 3-hydroxy-N,2,2-trimethylpropan-1-amine | 27 |
| 1074 | *—CH3 | *—O—CH3 | 3-cyano-3-methylazetidin-1-yl | 19 |
| 1075 | *—CH3 | *—O—CH3 | 3,3-dimethylazetidin-1-yl | 19 |

-continued
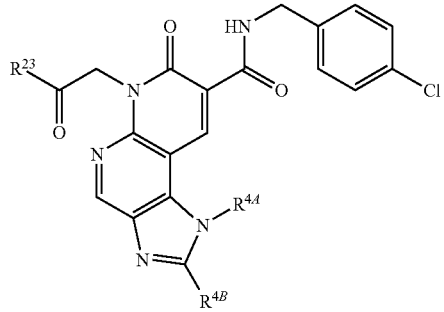
| Cmpd # | R⁴ᴬ | R⁴ᴮ | R²³ | Ex. # |
|---|---|---|---|---|
or a pharmaceutically acceptable salt thereof.
20. A compound of formula (1) according to claim 1, selected from a group consisting of:
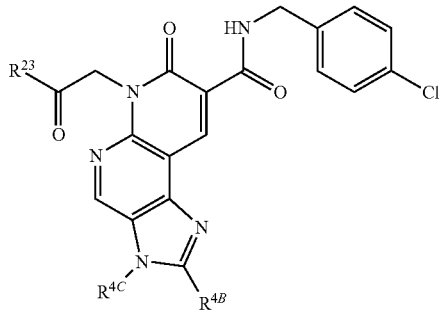
| Cmpd # | R²³ | R⁴ᶜ | R⁴ᴮ | Ex. # |
|---|---|---|---|---|
| 2001 | H₃C-, F-, azetidin-N-* | *—CH₃ | *—CH₃ | 13 |
| 2002 | H₃C-, F-, azetidin-N-* | *—CH₃ | H | 14 |
| 2003 | H₃C-, F-, azetidin-N-* | *—CH₃ | *—CH₂CH₃ | 14 |
| 2004 | H₃C-, F-, azetidin-N-* | *—CH₃ | *-cyclopropyl | 15 |
| 2005 | H₃C-, F-, azetidin-N-* | *—CH₂CH₃ | H | 14 |

-continued
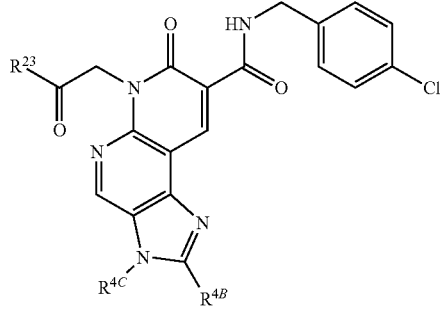
(1)
| Cmpd # | R23 | R4C | R4B | Ex. # |
|---|---|---|---|---|
| 2006 | H3C, F-azetidine-N-* | cyclopropyl-CH2-* | H | 14 |
| 2007 | H3C, F-azetidine-N-* | *—CH3 | *-CH(CH3)2 (isobutyl) | 15 |
| 2008 | H3C, F-azetidine-N-* | *-CH2CH3 | *—CH3 | 13 |
| 2009 | H3C, F-azetidine-N-* | H | *-CH2CH3 | 13 |
| 2010 | H3C, F-azetidine-N-* | H | *—CH3 | 13 |
| 2011 | H3C, F-azetidine-N-* | (CH3)2CH-* | H | 14 |
| 2012 | H3C, F-azetidine-N-* | H3C-O-CH2-* | H | 14 |
| 2013 | H3C, F-azetidine-N-* | H3C-O-CH2CH2-* | H | 14 |
| 2014 | H3C, F-azetidine-N-* | H3C-CH(OH)-CH2-* | H | 14 |
| 2015 | H3C, F-azetidine-N-* | HO-CH2CH2-* | *—CH3 | 13 |

-continued
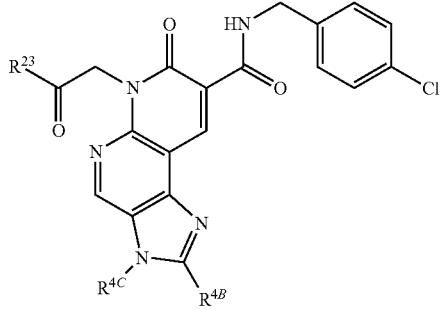
(1)
| Cmpd # | R²³ | R⁴ᶜ | R⁴ᴮ | Ex. # |
|---|---|---|---|---|
| 2016 | H₃C, F, azetidinyl | N≡C–CH₂–* | H | 14 |
| 2017 | H₃C, F, azetidinyl | *–CH₃ | *–N(CH₃)₂ | 18 |
| 2018 | H₃C, F, azetidinyl | *–CH₃ | *–cyclobutyl | 15 |
| 2019 | H₃C, azetidinyl | *–CH₃ | *–CH₃ | 29 |
| 2020 | H₃C, H₃C, azetidinyl | *–CH₃ | *–CH₃ | 29 |
| 2021 | H₃C, H₃C, azetidinyl | *–CH₃ | *–cyclopropyl | 15 |
| 2022 | H₃C, H₃C, azetidinyl | H₃C–CH₂–* | *–CH₃ | 29 |
| 2023 | H₃C, azetidinyl | *–CH₃ | *–cyclopropyl | 15 |
| 2024 | H₃C, azetidinyl | H₃C–CH₂–* | *–CH₃ | 29 |
| 2025 | H₃C, H₃C, azetidinyl | H | *–CH₃ | 14 |
or a pharmaceutically acceptable salt thereof.

21. A compound of formula (1) according to claim 1, selected from a group consisting of:

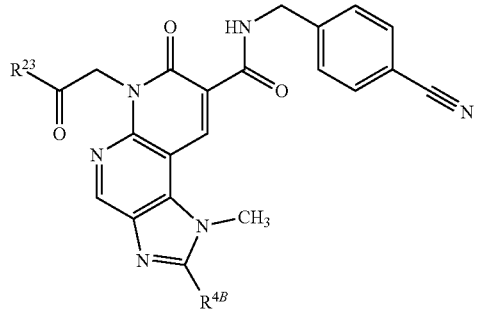
(1)

| Cmpd # | R²³ | R⁴ᴮ | Ex. # |
|---|---|---|---|
| 3001 | H₃C–[3-F-3-Me-azetidinyl]–* | *–CH₃ | 28 |
| 3002 | H₃C–[3,3-diMe-azetidinyl]–* | *–cyclopropyl | 26-27 |
| 3003 | H₃C–[3-F-3-Me-azetidinyl]–* | *–cyclopropyl | 26-27 |
| 3004 | H₃C–[3-F-3-Me-azetidinyl]–* | *–CH₂CH₃ | 30 |
| 3005 | H₃C–[3,3-diMe-azetidinyl]–* | *–CH₂CH₃ | 30 |
| 3006 | H₃C–[3-F-3-Me-azetidinyl]–* | *–OCH₃ (methoxymethyl) | 19 | or a pharmaceutically acceptable salt thereof.

22. A compound of formula (1) according to claim 1, selected from a group consisting of:

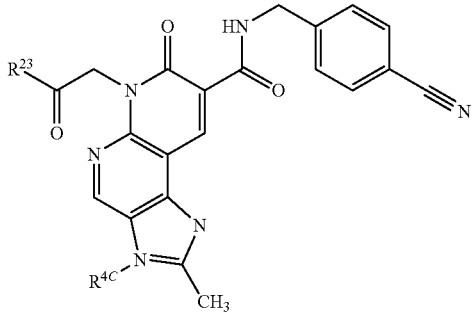
(I)

| Cmpd # | R²³ | R⁴ᶜ | tᴿ (min) | (M+H)+ | Ex. # |
|---|---|---|---|---|---|
| 4001 | H₃C–[3,3-diMe-azetidinyl]–* | *–CH₃ | 4.37 | 498.3 | 13 |
| 4002 | H₃C–[3-F-3-Me-azetidinyl]–* | *–CH₃ | 4.12 | 502.3 | 13 |
| 4003 | H₃C–[3-Me-azetidinyl]–* | *–CH₃ | 4.06 | 484.3 | 13 |
| 4004 | H₃C–[3,3-diMe-azetidinyl]–* | H₃C–CH₂–* | 4.56 | 512.3 | 13 |
| 4005 | H₃C–[3-Me-azetidinyl]–* | H₃C–CH₂–* | 4.07 | 498.3 | 13 |
| 4006 | H₃C–[3-F-3-Me-azetidinyl]–* | H₃C–CH₂–* | 4.32 | 516.3 | 13 | or a pharmaceutically acceptable salt thereof.

23. A compound selected from a group consisting of:

| Cmpd # | Structure | Ex. # |
|---|---|---|
| 5001 | (structure shown) | 23 |

| Cmpd # | Structure | Ex. # |
|---|---|---|
| 5002 | 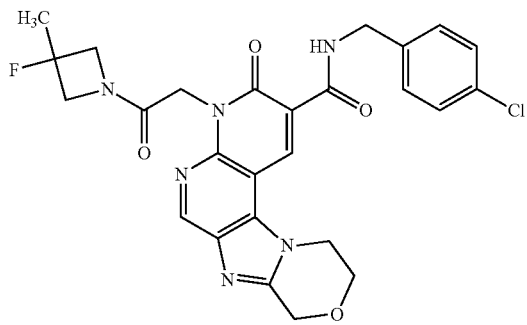 [SMILES: CC1(F)CN(C(=O)Cn2c(=O)c(C(=O)NCc3ccc(Cl)cc3)cc3c4c(cnc32)nc2n4CCOC2)C1] | 23 |
| 5003 | 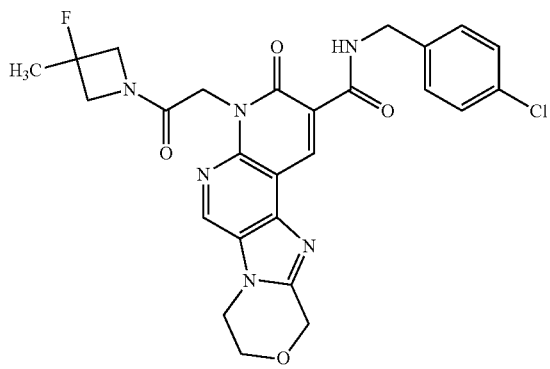 [SMILES: CC1(F)CN(C(=O)Cn2c(=O)c(C(=O)NCc3ccc(Cl)cc3)cc3c4nc5n(c4cnc32)CCOC5)C1] | 16 |
| 5004 | 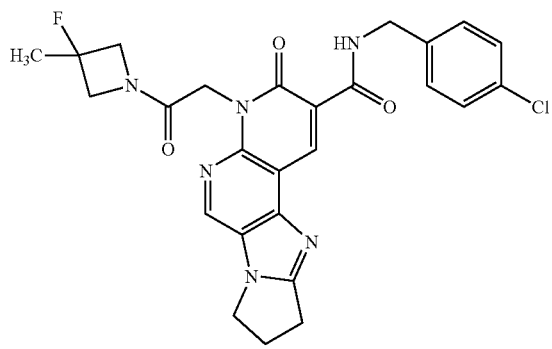 [SMILES: CC1(F)CN(C(=O)Cn2c(=O)c(C(=O)NCc3ccc(Cl)cc3)cc3c4nc5n(c4cnc32)CCC5)C1] | 16 |
| 5005 | 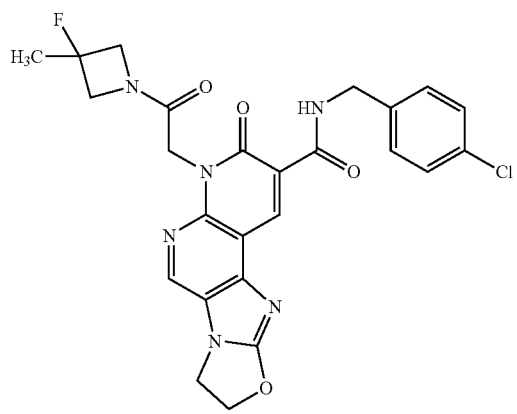 [SMILES: CC1(F)CN(C(=O)Cn2c(=O)c(C(=O)NCc3ccc(Cl)cc3)cc3c4nc5n(c4cnc32)CCO5)C1] | 17 |

-continued

| Cmpd # | Structure | Ex. # |
|---|---|---|
| 5006 | 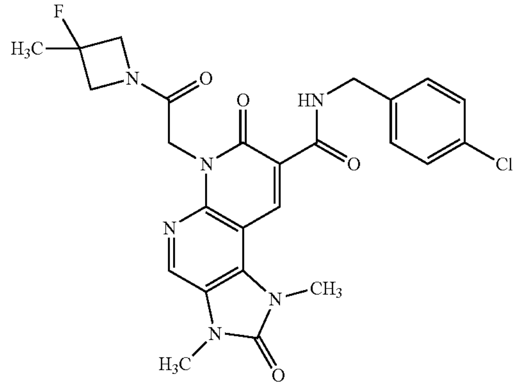 [SMILES: Cn1c(=O)n(C)c2c3cc(C(=O)NCc4ccc(Cl)cc4)c(=O)n(CC(=O)N4CC(C)(F)C4)c3ncc21] | 17 |
| 5007 | 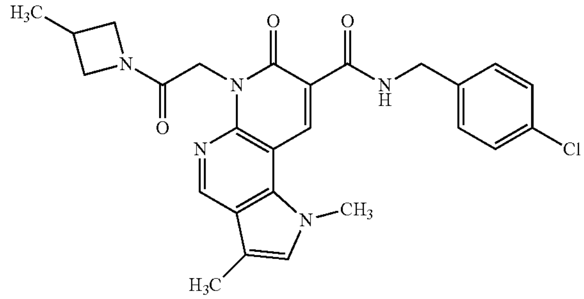 [SMILES: Cc1cn(C)c2c1cnc1c2cc(C(=O)NCc2ccc(Cl)cc2)c(=O)n1CC(=O)N1CC(C)C1] | 4 |
| 5008 | 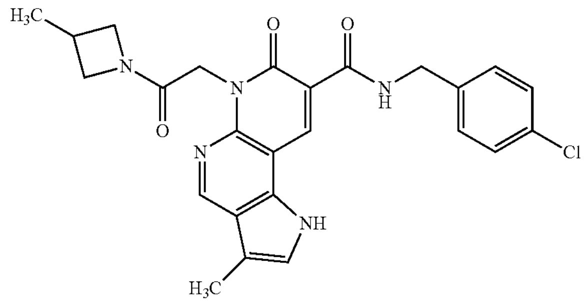 [SMILES: Cc1c[nH]c2c1cnc1c2cc(C(=O)NCc2ccc(Cl)cc2)c(=O)n1CC(=O)N1CC(C)C1] | 4 |
| 5009 | 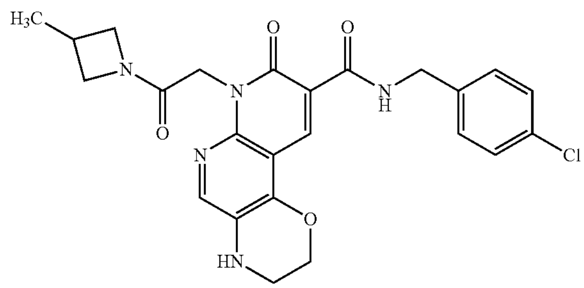 [SMILES: CC1CN(C(=O)Cn2c(=O)c(C(=O)NCc3ccc(Cl)cc3)cc3c4c(cnc32)NCCO4)C1] | 8 |
| 5010 | 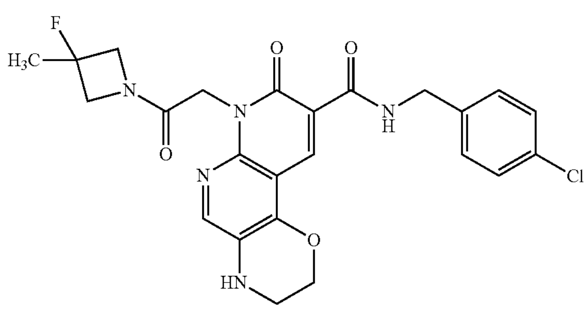 [SMILES: CC1(F)CN(C(=O)Cn2c(=O)c(C(=O)NCc3ccc(Cl)cc3)cc3c4c(cnc32)NCCO4)C1] | 7 |

| Cmpd # | Structure | Ex. # |
|---|---|---|
| 5011 | 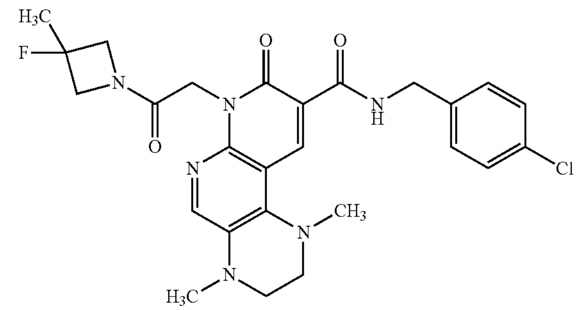 [SMILES: CN1CCN(C)c2c1cnc1c2cc(C(=O)NCc2ccc(Cl)cc2)c(=O)n1CC(=O)N1CC(C)(F)C1] | 5 |
| 5012 | 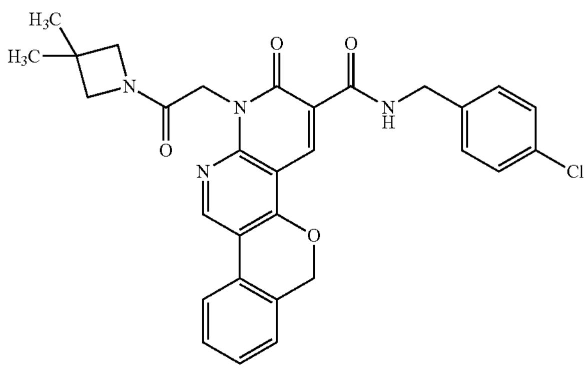 [SMILES: CC1(C)CN(C(=O)Cn2c(=O)c(C(=O)NCc3ccc(Cl)cc3)cc3c4c(cnc32)-c2ccccc2CO4)C1] | 6 |
| 5013 | 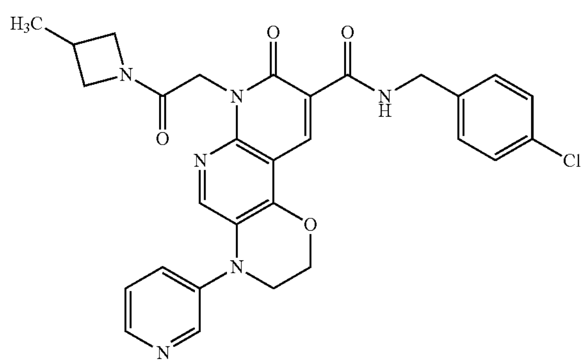 [SMILES: CC1CN(C(=O)Cn2c(=O)c(C(=O)NCc3ccc(Cl)cc3)cc3c4c(cnc32)N(c2cccnc2)CCO4)C1] | 9 |
| 5014 | 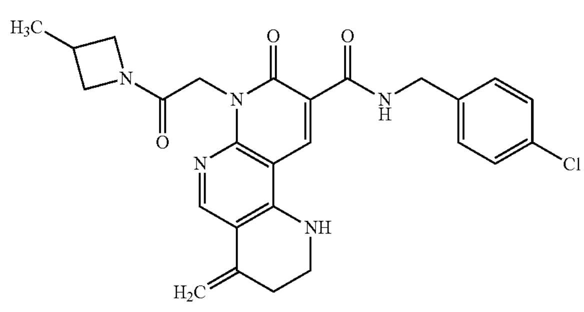 [SMILES: C=C1CCNc2c1cnc1c2cc(C(=O)NCc2ccc(Cl)cc2)c(=O)n1CC(=O)N1CC(C)C1] | 4 |

-continued

| Cmpd # | Structure | Ex. # |
|---|---|---|
| 5015 | 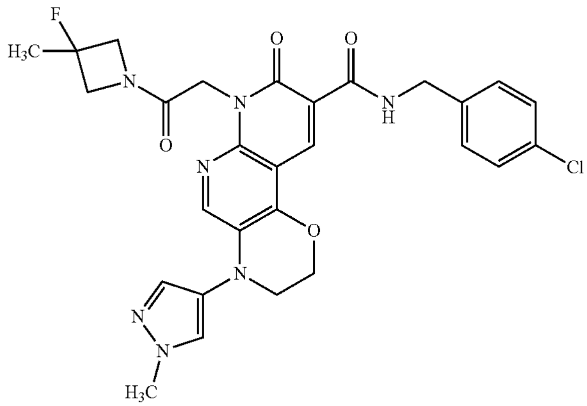 [SMILES: Cn1cc(N2CCOc3c2cnc2c3cc(C(=O)NCc3ccc(Cl)cc3)c(=O)n2CC(=O)N2CC(C)(F)C2)cn1] | 9 |
| 5016 | 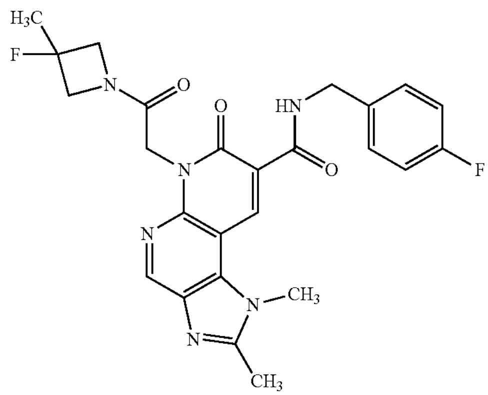 [SMILES: Cc1nc2cnc3c(cc(C(=O)NCc4ccc(F)cc4)c(=O)n3CC(=O)N3CC(C)(F)C3)c2n1C] | 28 |
| 5017 | 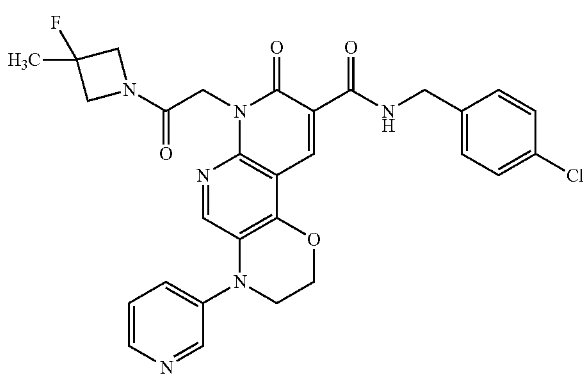 [SMILES: CC1(F)CN(C(=O)Cn2c(=O)c(C(=O)NCc3ccc(Cl)cc3)cc3c4c(cnc32)N(c2cccnc2)CCO4)C1] | 9 |
| 5018 | 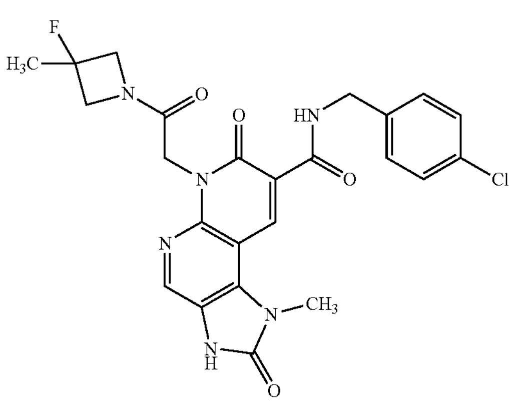 [SMILES: Cn1c(=O)[nH]c2cnc3c(cc(C(=O)NCc4ccc(Cl)cc4)c(=O)n3CC(=O)N3CC(C)(F)C3)c21] | 20 |

-continued

| Cmpd # | Structure | Ex. # |
|---|---|---|
| 5019 | 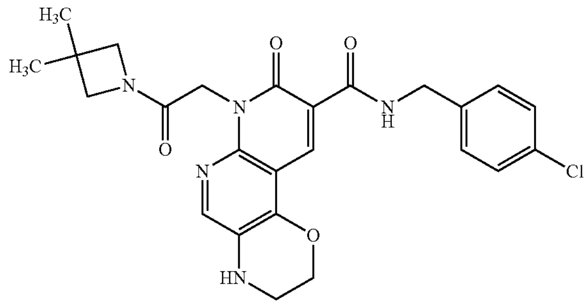 [SMILES: CC1(C)CN(C(=O)Cn2c(=O)c(C(=O)NCc3ccc(Cl)cc3)cc3c4c(cnc32)NCCO4)C1] | 8 |
| 5020 | 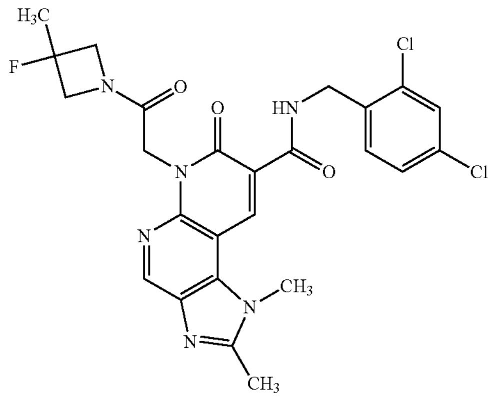 [SMILES: Cc1nc2cnc3c(cc(C(=O)NCc4ccc(Cl)cc4Cl)c(=O)n3CC(=O)N3CC(C)(F)C3)c2n1C] | 28 |
| 5021 | 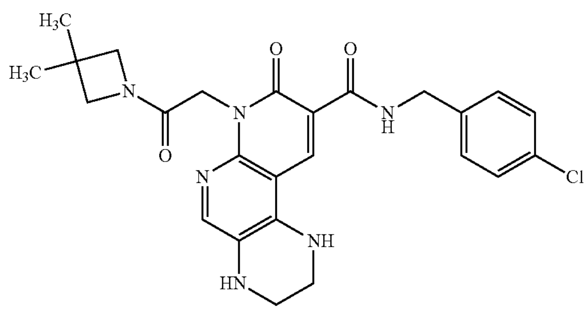 [SMILES: CC1(C)CN(C(=O)Cn2c(=O)c(C(=O)NCc3ccc(Cl)cc3)cc3c4c(cnc32)NCCN4)C1] | 5 |
| 5022 | 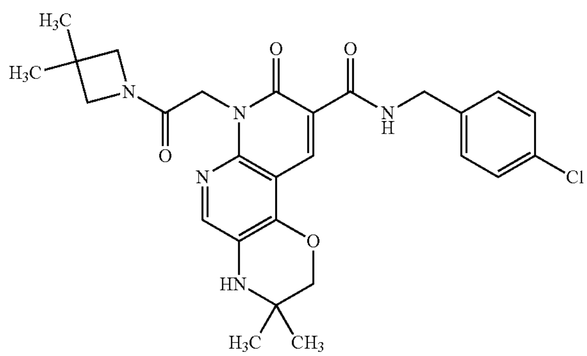 [SMILES: CC1(C)CN(C(=O)Cn2c(=O)c(C(=O)NCc3ccc(Cl)cc3)cc3c4c(cnc32)NC(C)(C)CO4)C1] | 8 |

| Cmpd # | Structure | Ex. # |
|---|---|---|
| 5023 | 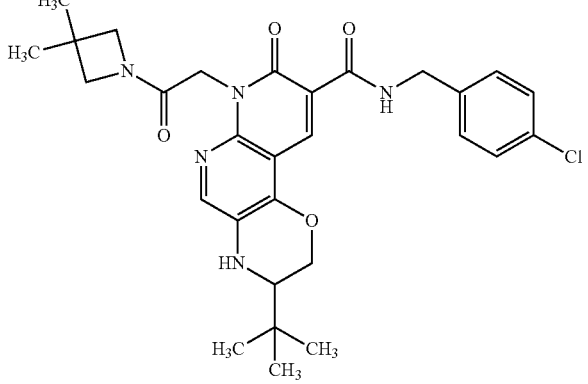 | 8 |
| 5024 | 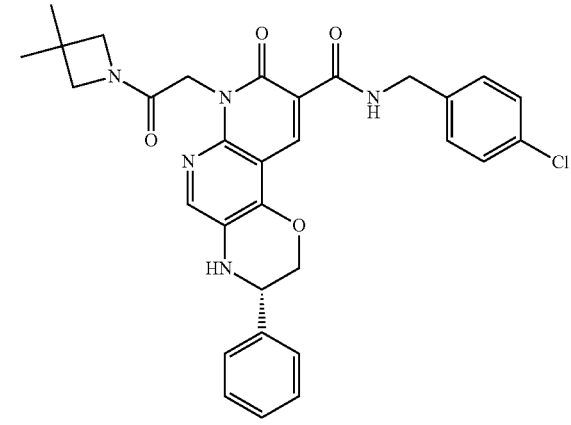 [SMILES: CC1(C)CN(C(=O)Cn2c(=O)c(C(=O)NCc3ccc(Cl)cc3)cc3c4c(cnc32)N[C@@H](c2ccccc2)CO4)C1] | 8 |
| 5025 | 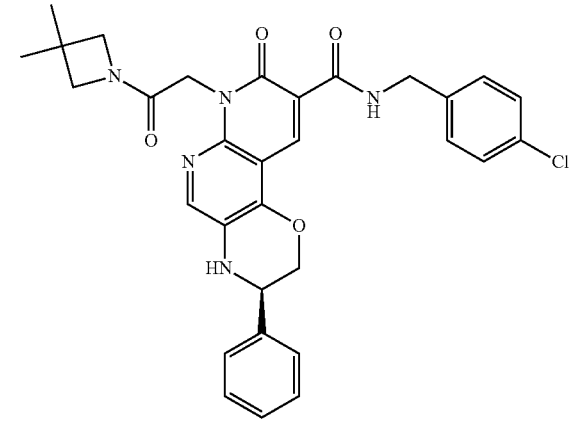 [SMILES: CC1(C)CN(C(=O)Cn2c(=O)c(C(=O)NCc3ccc(Cl)cc3)cc3c4c(cnc32)N[C@H](c2ccccc2)CO4)C1] | 8 |
| 5026 | 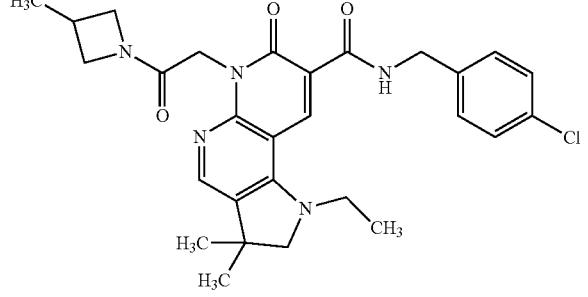 | 4 |

| Cmpd # | Structure | Ex. # |
|---|---|---|
| 5027 | 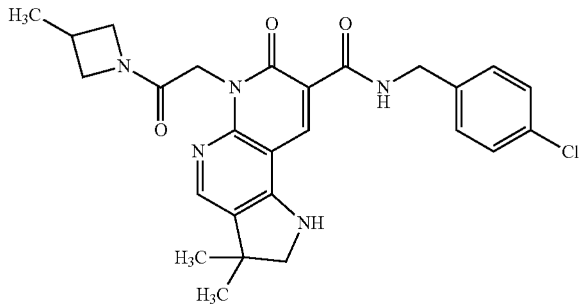 [SMILES: CC1CN(C(=O)Cn2c(=O)c(C(=O)NCc3ccc(Cl)cc3)cc3c4c(cnc32)C(C)(C)CN4)C1] | 4 |
| 5028 | 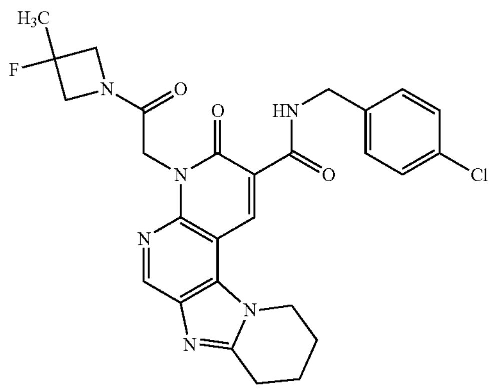 [SMILES: CC1(F)CN(C(=O)Cn2c(=O)c(C(=O)NCc3ccc(Cl)cc3)cc3c4c(cnc32)nc2n4CCCC2)C1] | 23 |
| 5029 | 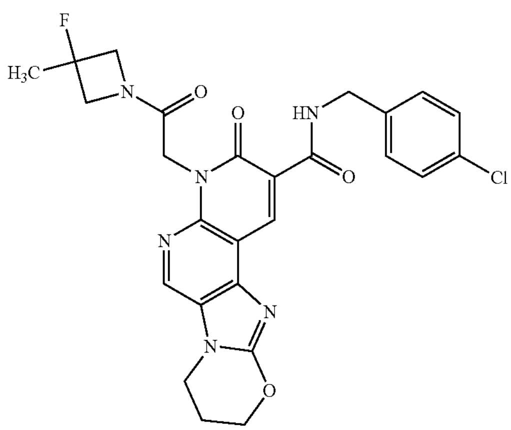 [SMILES: CC1(F)CN(C(=O)Cn2c(=O)c(C(=O)NCc3ccc(Cl)cc3)cc3c4nc5n(c4cnc32)CCCO5)C1] | 17 |
| 5030 | 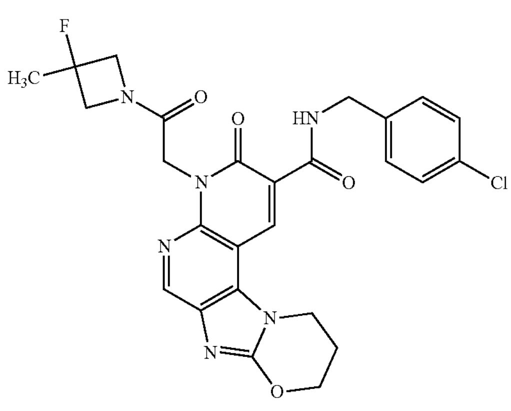 [SMILES: CC1(F)CN(C(=O)Cn2c(=O)c(C(=O)NCc3ccc(Cl)cc3)cc3c4c(cnc32)nc2n4CCCO2)C1] | 17 |

| Cmpd # | Structure | Ex. # |
|---|---|---|
| 5031 | 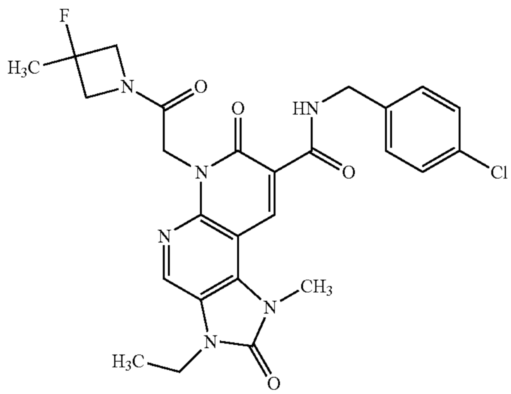 [SMILES: CCn1c(=O)n(C)c2c3cc(C(=O)NCc4ccc(Cl)cc4)c(=O)n(CC(=O)N4CC(C)(F)C4)c3ncc21] | 20 |
| 5032 | 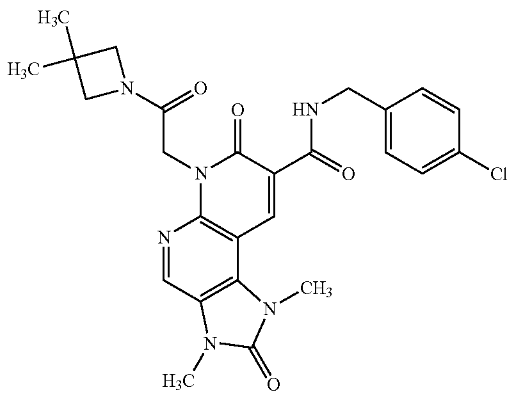 [SMILES: Cn1c(=O)n(C)c2c3cc(C(=O)NCc4ccc(Cl)cc4)c(=O)n(CC(=O)N4CC(C)(C)C4)c3ncc21] | 20 |
| 5033 | 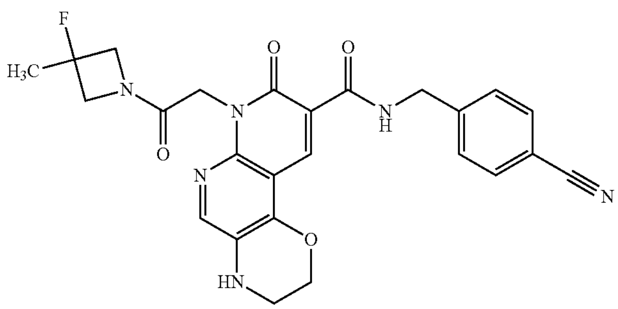 [SMILES: CC1(F)CN(C(=O)Cn2c(=O)c(C(=O)NCc3ccc(C#N)cc3)cc3c4c(cnc32)NCCO4)C1] | 7 |
| 5034 | 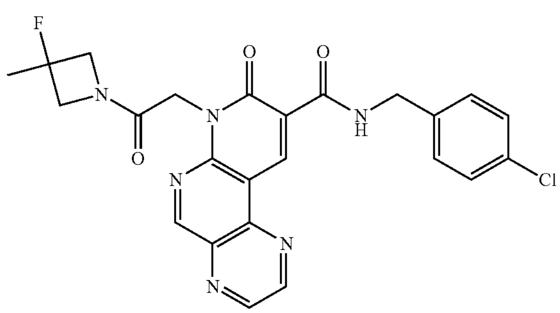 [SMILES: CC1(F)CN(C(=O)Cn2c(=O)c(C(=O)NCc3ccc(Cl)cc3)cc3c4nccnc4cnc32)C1] | 12 |

-continued
| Cmpd # | Structure | Ex. # |
|---|---|---|
| 5035 | 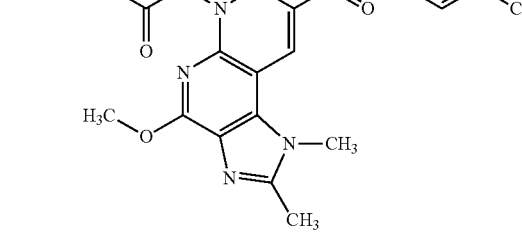 | 24 |
| 5036 | 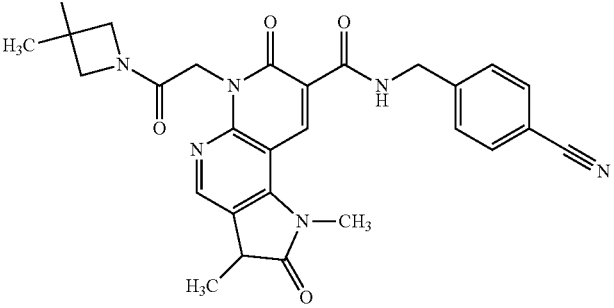 | 20 |
| 5037 | 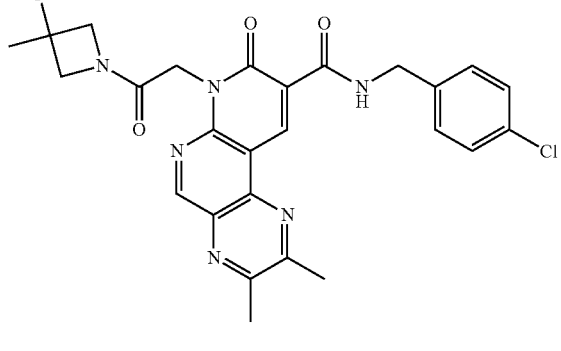 | 12 |
| 5038 | 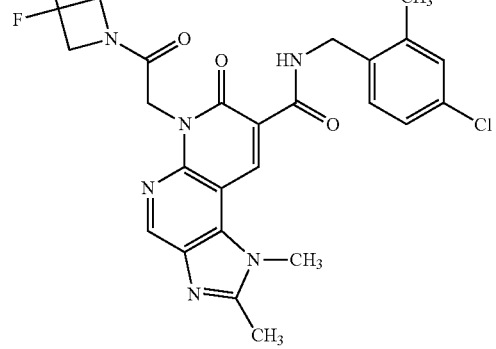 | 28 |

-continued

| Cmpd # | Structure | Ex. # |
|---|---|---|
| 5039 | 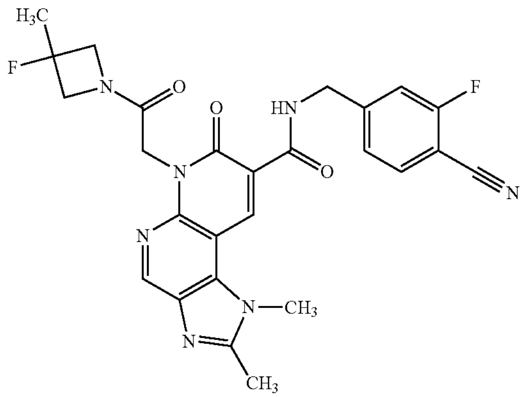 [SMILES: Cc1nc2cnc3c(cc(C(=O)NCc4ccc(C#N)c(F)c4)c(=O)n3CC(=O)N3CC(C)(F)C3)c2n1C] | 28 |
| 5040 | 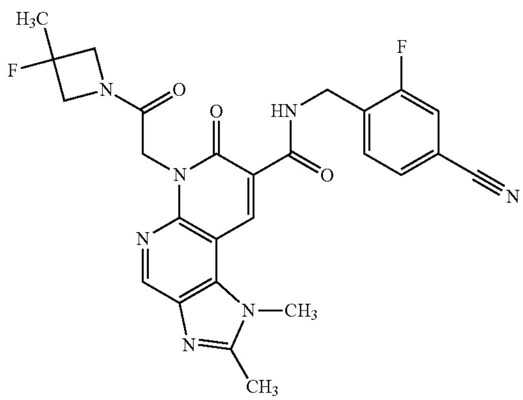 [SMILES: Cc1nc2cnc3c(cc(C(=O)NCc4ccc(C#N)cc4F)c(=O)n3CC(=O)N3CC(C)(F)C3)c2n1C] | 28 |
| 5041 | 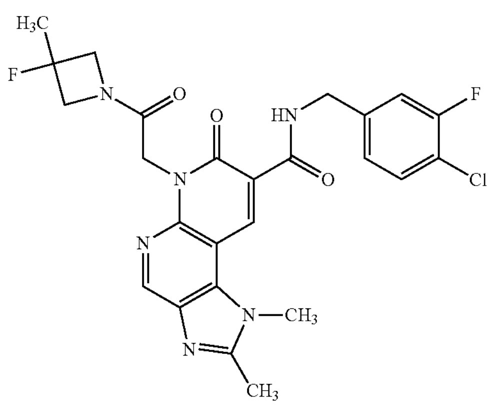 [SMILES: Cc1nc2cnc3c(cc(C(=O)NCc4ccc(Cl)c(F)c4)c(=O)n3CC(=O)N3CC(C)(F)C3)c2n1C] | 28 |
| 5042 | 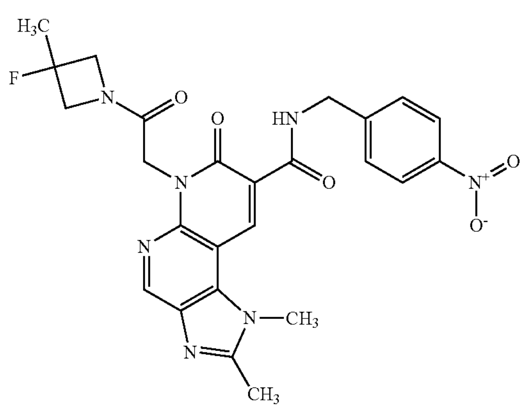 [SMILES: Cc1nc2cnc3c(cc(C(=O)NCc4ccc([N+](=O)[O-])cc4)c(=O)n3CC(=O)N3CC(C)(F)C3)c2n1C] | 28 |

-continued

| Cmpd # | Structure | Ex. # |
|---|---|---|
| 5043 | 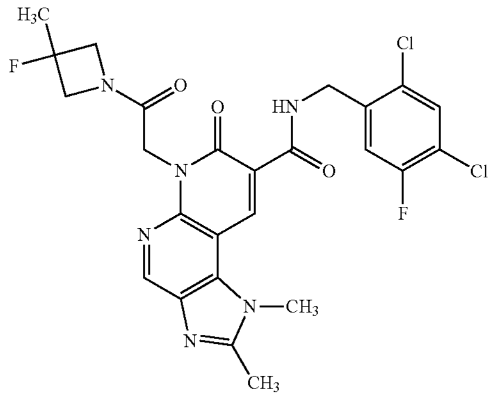 [SMILES: Cc1nc2cnc3c(cc(C(=O)NCc4cc(F)c(Cl)cc4Cl)c(=O)n3CC(=O)N3CC(C)(F)C3)c2n1C] | 28 |
| 5044 | 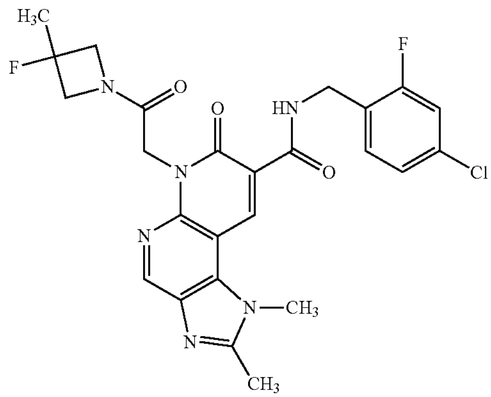 [SMILES: Cc1nc2cnc3c(cc(C(=O)NCc4ccc(Cl)cc4F)c(=O)n3CC(=O)N3CC(C)(F)C3)c2n1C] | 28 |
| 5045 | 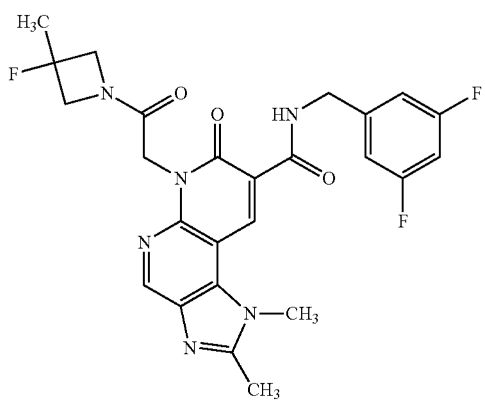 [SMILES: Cc1nc2cnc3c(cc(C(=O)NCc4cc(F)cc(F)c4)c(=O)n3CC(=O)N3CC(C)(F)C3)c2n1C] | 28 |
| 5046 | 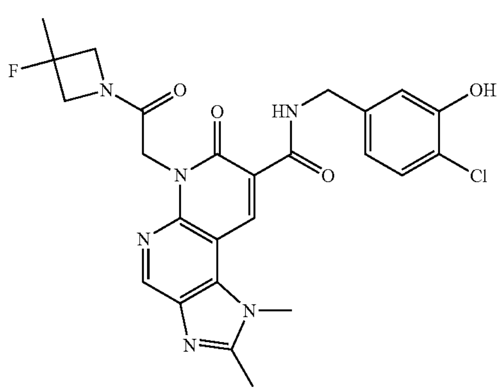 [SMILES: Cc1nc2cnc3c(cc(C(=O)NCc4ccc(Cl)c(O)c4)c(=O)n3CC(=O)N3CC(C)(F)C3)c2n1C] | 28 |

| Cmpd # | Structure | Ex. # |
|---|---|---|
| 5047 | 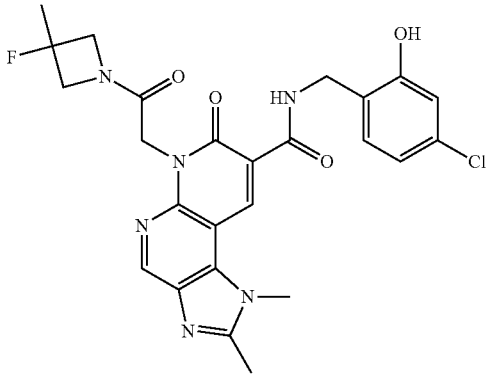 [SMILES: Cc1nc2cnc3c(cc(C(=O)NCc4ccc(Cl)cc4O)c(=O)n3CC(=O)N3CC(C)(F)C3)c2n1C] | 28 |
| 5048 | 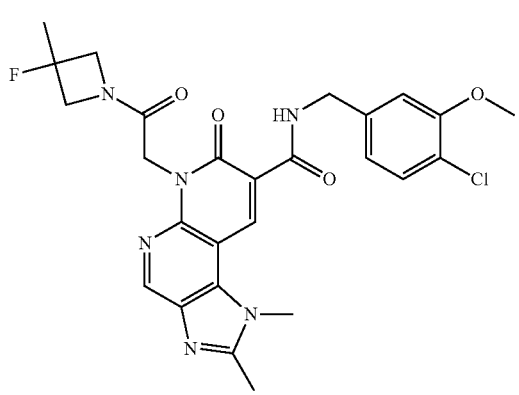 [SMILES: COc1cc(CNC(=O)c2cc3c4c(cnc3n(CC(=O)N3CC(C)(F)C3)c2=O)nc(C)n4C)ccc1Cl] | 28 |
or a pharmaceutically acceptable salt thereof.